(12) United States Patent
Mantell et al.

(10) Patent No.: US 6,624,158 B2
(45) Date of Patent: Sep. 23, 2003

(54) PURINE DERIVATIVES

(75) Inventors: Simon John Mantell, County of Kent (GB); Peter Thomas Stephenson, County of Kent (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/933,421

(22) Filed: Aug. 20, 2001

(65) Prior Publication Data

US 2002/0072597 A1 Jun. 13, 2002

Related U.S. Application Data

(60) Provisional application No. 60/239,644, filed on Oct. 12, 2000.

(30) Foreign Application Priority Data

Sep. 15, 2000 (GB) .............................................. 0022695

(51) Int. Cl.$^7$ ...................... C07D 473/34; A61K 31/52; A61P 11/06; A61P 11/00; A61P 11/08
(52) U.S. Cl. .............................. 514/217.06; 514/234.2; 514/263.2; 544/118; 544/277; 540/575
(58) Field of Search .............................. 514/266, 234.2, 514/217.06; 544/118, 277; 540/575

(56) References Cited

FOREIGN PATENT DOCUMENTS

| WO | WO 8803147 | 5/1988 | ......... C07H/19/167 |
|----|------------|--------|------------------|
| WO | 9111172 | 8/1991 | |
| WO | 9402518 | 2/1994 | |
| WO | WO 9407905 | 4/1994 | ......... C07H/19/167 |
| WO | 9801459 | 1/1998 | ........... C07H/19/16 |
| WO | 9828319 | 7/1998 | ......... C07H/19/167 |
| WO | 9855148 | 12/1998 | |
| WO | WO 9924451 | 5/1999 | ........... C07H/19/00 |
| WO | WO 9934804 | 7/1999 | ........... A61K/31/52 |
| WO | 9938877 | 8/1999 | ........... C07H/19/00 |
| WO | 9941267 | 8/1999 | ........... C07H/19/16 |
| WO | 9967263 | 12/1999 | ........... C07H/19/16 |
| WO | 9967264 | 12/1999 | ......... C07H/19/167 |
| WO | 9967265 | 12/1999 | |
| WO | 9967266 | 12/1999 | ......... C07H/19/167 |
| WO | 0023457 | 4/2000 | ......... C07H/19/167 |
| WO | 0077018 | 12/2000 | ........... C07H/19/00 |
| WO | 0127130 | 4/2001 | ......... C07H/19/167 |
| WO | 0127131 | 4/2001 | ......... C07H/19/167 |
| WO | 0160835 | 8/2001 | ......... C07H/19/167 |

OTHER PUBLICATIONS

Opal et al Infectious Disease Clinics of North America 13(2), pp. 285–297, Jun. 1999.*
Chaby Drug Discovery Today 4(5) 209–221, May 1999.*
Berge, et al., *J. Pharm. Sci.*, 66, pp. 1–19 (1977); and.
Tronchet et al. Helv. Chim. Acta. 1980, 63(5), pp 1181.
Baraldi et al., J. Med Chem., vol. 41, No. 17, pp. 3174–3185, 1998.

* cited by examiner

Primary Examiner—Mark L. Berch
(74) Attorney, Agent, or Firm—Peter C. Richardson; Gregg C. Benson; Robert T. Ronau

(57) ABSTRACT

The present invention relates to compounds of the formula (I)

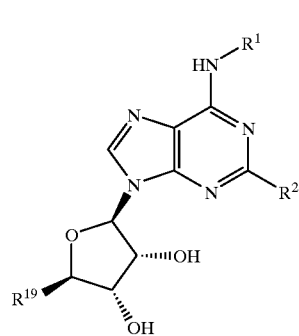

and pharmaceutically acceptable salts and solvates thereof, wherein $R^2$ is —$CH_2NHSO_2$—A—$R^3$, —$CONR^{10}$—$A^1$—$R^{11}$, —X—$NR^{12a}$—Y—$NR^{13}R^{14}$ or —CO—$NR^{18}$—$X^1$—$NR^{12}$—Y—$NR^{13}R^{14}$; $R^{19}$, where $R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$ and $R^1$, A, $R^3$, $R^{10}$, $R^{11}$, X, $R^{12a}$, Y, $R^{13}$, $R^{14}$, $R^{18}$, $X^1$, $R^{21}$ and $R^{22}$ are as defined in the specification. The invention also relates to processes for the preparation of, intermediates used in the preparation of, and compositions containing such compounds and the uses of such compounds as adenosine A2a receptor agonists. The invention is particularly related to methods of treating respiratory diseases such as adult respiratory distress syndrome, bronchitis, chronic bronchitis, chronic obstructive pulmonary disease, cystic fibrosis, asthma, emphysema bronchiectasis, chronic sinusitis and rhinitis.

54 Claims, No Drawings

PURINE DERIVATIVES

CROSS REFERENCE TO RELATED APPLICATIONS

This application claims the benefit of priority under 37 C.F.R. §1.78(a)(3) of U.S. Provisional Patent Application No. 60/239,644, filed Oct. 12, 2000.

This invention relates to purine derivatives. More particularly, this invention relates to 9-(5-heteroaryltetrahydrofuranyl)purine derivatives and to processes for the preparation of, intermediates used in the preparation of, compositions containing and the uses of, such derivatives.

These derivatives are selective, functional agonists of the human adenosine A2a receptor and may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Adenosine receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, for example, superoxide anion radicals ($O_2^-$), and granule products, for example, human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemo-attractant that recruits additional neutrophils to the inflammatory focus, whereas released $O_2^-$ and HNE adversely affect the pulmonary extracellular matrix. The A2 receptor subtype mediating many of these responses ($O_2^-$ and $LTB_4$/HNE release and cell adhesion) is established as A2a. The A2 subtype (A2a or A2b) mediating the other effects remains to be established.

Selective agonist activity at the A2a receptor is considered to offer greater therapeutic benefit than the use of non-selective adenosine receptor agonists because interaction with other subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with respiratory disease will be co-prescribed $\beta_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over the A2b receptor is also advantageous.

We have now surprisingly found the present purine derivatives inhibit neutrophil function and are selective agonists of the adenosine A2a receptor. They may also have antagonist activity at the adenosine A3 receptor. The present compounds may be used to treat any disease for which an adenosine A2a receptor agonist is indicated. They can be used to treat a disease where leukocyte (e.g. neutrophil, eosinophil, basophil, lymphocyte, macrophage)-induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastro-intestinal tract or a psychotic disorder, or for wound healing.

Accordingly, the present invention provides a compound of the formula

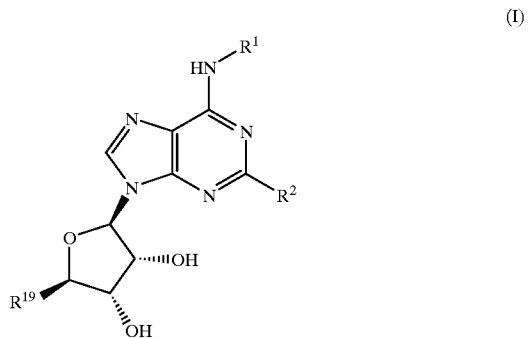

(I)

or a pharmaceutically acceptable salt or solvate thereof, wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^2$ is either
  (a) —$CH_2NHSO_2$—A—$R^3$ wherein
  A is a bond or $C_1$–$C_3$ alkylene; and
  $R^3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^3$ is not H when A is a bond, or (ii) when A is $C_2$–$C_3$ alkylene, —$NR^8R^9$, —$OR^4$, —$COOR^4$, —$OCOR^5$, —$SO_2R^5$, —CN, —$SO_2NR^4R^4$, —$NR^4COR^5$ or —$CONR^4R^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^6$, —$S(O)_m R^7$, —$SO_2NR^6R^6$ or —$CONR^6R^6$; or (b) —CONR$^{10}$—A$^1$—R$^{11}$ wherein A$^1$ is a bond or C$_1$–C$_6$ alkylene;

R$^{10}$ is H or C$_1$–C$_6$ alkyl; and

R$^{11}$ is (i) H, C$_1$–C$_6$ alkyl, C$_3$–C$_8$ cycloalkyl, phenyl or naphthyl, said C$_3$–C$_8$ cycloalkyl, phenyl and naphthyl being optionally substituted by C$_1$–C$_6$ alkyl, phenyl, C$_1$–C$_6$ alkoxy-(C$_1$–C$_6$)-alkyl, R$^4$R$^4$N—(C$_1$–C$_6$)-alkyl, halo-(C$_1$–C$_6$)-alkyl, fluoro-(C$_1$–C$_6$)-alkoxy, C$_2$–C$_5$ alkanoyl, halo, —OR$^4$, cyano, —COOR$^4$, C$_3$–C$_8$ cycloalkyl, —S(O)$_m$R$^5$, —NR$^4$R$^4$, —SO$_2$NR$^4$R$^4$, —CONR$^4$R$^4$, —NR$^4$COR$^5$ or —NR$^4$SO$_2$R$^5$, with the proviso that R$^{11}$ is not H when A$^1$ is a bond, or (ii) when A$^1$ is C$_2$–C$_6$ alkylene, —NR$^4$R$^4$, —OR$^4$, —OCOR$^5$, —SO$_2$R$^5$, —SO$_2$NR$^4$R$^4$, —NR$^4$SO$_2$R$^5$ or —NR$^4$COR$^5$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, C$_1$–C$_6$ alkoxy-(C$_1$–C$_6$)-alkyl, R$^6$R$^6$N—(C$_1$–C$_6$)-alkyl, halo-(C$_1$–C$_6$)-alkyl, fluoro-(C$_1$–C$_6$)-alkoxy, fluoro-(C$_2$–C$_5$)-alkanoyl, halo, cyano, —OR$^6$, R$^7$, —COR$^6$, —NR$^6$R$^6$, —COOR$^6$, —S(O)$_m$R$^7$, —SO$_2$NR$^6$R$^6$, —CONR$^6$R$^6$, —NR$^6$SO$_2$R$^7$ or —NR$^6$COR$^7$ and optionally N-substituted by C$_1$–C$_6$ alkoxy-(C$_1$–C$_6$)-alkyl, R$^6$R$^6$N—(C$_2$–C$_6$)-alkyl, halo-(C$_1$–C$_6$)-alkyl, fluoro-(C$_2$–C$_5$)-alkanoyl, R$^7$, —COR$^6$, —COOR$^7$, —SO$_2$R$^7$, —SO$_2$NR$^6$R$^6$ or —CONR$^6$R$^6$, or (iv) when A$^1$ is C$_2$–C$_6$ alkylene, N-linked azetidinyl, pyrrolidinyl, piperidinyl, morpholinyl, piperazinyl, homopiperazinyl, homopiperidinyl or tetrahydroquinolinyl, each being optionally C-substituted by C$_1$–C$_6$ alkyl, phenyl, C$_1$–C$_6$ alkoxy-(C$_1$–C$_6$)-alkyl, R$^4$R$^4$N—(C$_1$–C$_6$)-alkyl, halo-(C$_1$–C$_6$)-alkyl, fluoro-(C$_1$–C$_6$)-alkoxy, C$_2$–C$_5$ alkanoyl, halo, —OR$^4$, cyano, —COOR$^4$, C$_3$–C$_8$ cycloalkyl, —S(O)$_m$R$^5$, —NR$^4$R$^4$, —SO$_2$NR$^4$R$^4$, —CONR$^4$R$^4$, —NR$^4$COR$^5$ or —NR$^4$SO$_2$R$^5$ and said piperazinyl and homopiperazinyl being optionally substituted on the nitrogen not attached to A$^1$ by C$_1$–C$_6$ alkyl, phenyl, C$_1$–C$_6$ alkoxy-(C$_2$–C$_6$)-alkyl, R$^4$R$^4$N—(C$_2$–C$_6$)-alkyl, halo-(C$_1$–C$_6$)-alkyl, C$_2$–C$_5$ alkanoyl, —COOR$^5$, C$_3$–C$_8$ cycloalkyl, —SO$_2$R$^5$, —SO$_2$NR$^4$R$^4$ or —CONR$^4$R$^4$, or (v) when A$^1$ is C$_1$–C$_6$ alkylene, —COOR$^4$, —CN or —CONR$^4$R$^4$; or (c) —X—NR$^{12a}$—Y—NR$^{13}$R$^{14}$ wherein X is —CH$_2$— or —CH$_2$CH$_2$—; and R$^{12a}$ is H or C$_1$–C$_6$ alkyl; or (d) —CO—NR$^{18}$—X$^1$—NR$^{12}$—Y—NR$^{13}$R$^{14}$ wherein (i) X$^1$ is (1) unbranched C$_2$–C$_3$ alkylene optionally substituted by C$_1$–C$_6$ alkyl or C$_3$–C$_8$ cycloalkyl or (2) a group of the formula —(CH$_2$)$_n$—W—(CH$_2$)$_p$— wherein W is C$_5$–C$_7$ cycloalkylene, n is 0 or 1 and p is 0 or 1;

R$^{18}$ is H or C$_1$–C$_6$ alkyl; and

R$^{12}$ is H or C$_1$–C$_6$ alkyl; or (ii) X$^1$ and R$^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by C$_1$–C$_6$ alkyl; and R$^{18}$ is H or C$_1$–C$_6$ alkyl; or (iii) X$^1$ and R$^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by C$_1$–C$_6$ alkyl; and R$^{12}$ is H or C$_1$–C$_6$ alkyl;

Y is CO, CS, SO$_2$ or C=N(CN);

R$^4$ is H, C$_1$–C$_6$ alkyl, C$_3$–C$_8$ cycloalkyl or phenyl;

R$^5$ is C$_1$–C$_6$ alkyl, C$_3$–C$_8$ cycloalkyl or phenyl;

R$^6$ is H, C$_1$–C$_6$ alkyl, C$_3$–C$_8$ cycloalkyl, phenyl, naphthyl or het;

R$^7$ is C$_1$–C$_6$ alkyl, C$_3$–C$_8$ cycloalkyl, phenyl, naphthyl or het;

either, R$^8$ and R$^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by C$_1$–C$_6$ alkyl, C$_3$–C$_8$ cycloalkyl, phenyl, C$_1$–C$_6$ alkoxy-(C$_1$–C$_6$)-alkyl, R$^4$R$^4$N—(C$_1$–C$_6$)-alkyl, fluoro-(C$_1$–C$_6$)-alkyl, —CONR$^4$R$^4$, —COOR$^4$ or C$_2$–C$_5$ alkanoyl, and optionally substituted on a ring carbon atom not adjacent to a ring nitrogen atom by fluoro-(C$_1$–C$_6$)-alkoxy, halo, —OR$^4$, cyano, —S(O)$_m$R$^5$, —NR$^4$R$^4$, —SO$_2$NR$^4$R$^4$, —NR$^4$COR$^5$ or —NR$^4$SO$_2$R$^5$, and said piperazin-1-yl and homopiperazin-1-yl being optionally substituted on the ring nitrogen atom not attached to A or the C$_2$–C$_6$ alkylene group, as the case may be, by C$_1$–C$_6$ alkyl, phenyl, C$_1$–C$_6$ alkoxy-(C$_2$–C$_6$)-alkyl, R$^4$R$^4$N—(C$_2$–C$_6$)-alkyl, fluoro-(C$_1$–C$_6$)-alkyl, C$_2$–C$_5$ alkanoyl, —COOR$^5$, C$_3$–C$_8$ cycloalkyl, —SO$_2$R$^5$, —SO$_2$NR$^4$R$^4$ or —CONR$^4$R$^4$, or, R$^8$ is H, C$_1$–C$_6$ alkyl, C$_3$–C$_8$ cycloalkyl, phenyl or benzyl and R$^9$ is H, C$_1$–C$_6$ alkyl, C$_3$–C$_8$ cycloalkyl, phenyl, benzyl, fluoro-(C$_1$–C$_6$)-alkyl, —CONR$^4$R$^4$, —COOR$^5$, —COR$^5$, —SO$_2$R$^5$ or —SO$_2$NR$^4$R$^4$, said C$_1$–C$_6$ alkyl being optionally substituted by phenyl;

either, R$^{13}$ and R$^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by C$_1$–C$_6$ alkyl or C$_3$–C$_8$ cycloalkyl and optionally substituted on a ring carbon atom not adjacent to a ring nitrogen atom by —NR$^{15}$R$^{16}$ or —OR$^4$, or, R$^{13}$ is H, C$_1$–C$_6$ alkyl, C$_3$–C$_8$ cycloalkyl or benzyl, said C$_1$–C$_6$ alkyl being optionally substituted by C$_3$–C$_8$ cycloalkyl, and R$^{14}$ is (1) azetidin-3-yl, pyrrolidin-3-yl, piperidin-3-yl, piperidin-4-yl, homopiperidin-3-yl or homopiperidin-4-yl, each being optionally substituted by C$_1$–C$_6$ alkyl, C$_3$–C$_8$ cycloalkyl, phenyl, benzyl or het$^1$, or (2) —(C$_2$–C$_6$ alkylene)-NR$^8$R$^9$, or (3) —(C$_1$–C$_6$ alkylene)-R$^{17}$, or (4) C$_1$–C$_6$ alkyl or C$_3$–C$_8$ cycloalkyl;

R$^{15}$ and R$^{16}$ are either each independently H or C$_1$–C$_6$ alkyl or, taken together with the nitrogen atom to which they are attached, represent azetidinyl, pyrrolidinyl or piperidinyl, said azetidinyl, pyrrolidinyl and piperidinyl being optionally substituted by C$_1$–C$_6$ alkyl;

R$^{17}$ is (i) phenyl, pyridin-2-yl, pyridin-3-yl or pyridin-4-yl, each being optionally substituted by C$_1$–C$_6$ alkyl, C$_1$–C$_6$ alkoxy, —(C$_1$–C$_3$ alkylene)-(C$_1$–C$_6$ alkoxy), halo, cyano, —(C$_1$–C$_3$ alkylene)-CN, —CO$_2$H, —(C$_1$–C$_3$ alkylene)-CO$_2$H, —CO$_2$(C$_1$–C$_6$ alkyl), —($C_1$–$C_3$ alkylene)-$CO_2$($C_1$–$C_6$ alkyl), —($C_1$–$C_3$ alkylene)-$NR^{24}R^{24}$, —$CONR^{24}R^{24}$ or —($C_1$–$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or $het^1$;

m is 0, 1 or 2;

het, used in the definitions of $R^6$ and $R^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

$het^1$, used in the definition of $R^{14}$ and $R^{17}$, is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$;

$R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and $R_{24}$ is H or $C_1$–$C_6$ alkyl optionally substituted by cyclopropyl. In the above definitions, halo means fluoro, chloro, bromo or iodo and alkyl, alkylene, alkanoyl and alkoxy groups containing the requisite number of carbon atoms can be unbranched or branched chain. The heterocycle, as defined in $R^2$, parts (a)(iii) and (b)(iii), above may be aromatic or fully or partially saturated. The expressions 'C-linked' and 'N-linked' used in the definition of $R^2$, het and $het^1$ mean that the group is linked to the adjacent atom by a ring carbon or nitrogen atom, respectively. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,3-propylene and 1,2-propylene. Examples of alkanoyl include acetyl and propanoyl. Examples of cycloalkylene include cyclopentylene, cyclohexylene and cycloheptalyene. Examples of cycloalkyl include cyclopropyl, cyclobutyl, cyclopentyl, cyclohexyl and cycloheptyl. Examples of cycloalkoxy include cyclopropyloxy, cyclobutyloxy, cyclopentyloxy, cyclohexyloxy and cycloheptyloxy. Examples of $het^1$ include pyrrolyl, imidazolyl, triazolyl, thienyl, furyl, thiazolyl, oxazolyl, thiadiazolyl, oxadiazolyl, pyridinyl, pyrimidinyl, pyridazinyl and pyrazinyl.

The pharmaceutically acceptable salts of the compounds of the formula (i) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, malate, fumarate, lactate, tartrate, citrate, gluconate, succinate, saccharate, benzoate, methanesulphonate, ethanesulphonate, benzenesulphonate, p-toluenesulphonate, pamoate, adipate and xinafoate (1-hydroxy-2-naphthoate) salts.

Suitable base salts are formed from bases which form non-toxic salts and examples are the sodium, potassium, aluminium, calcium, magnesium, zinc and diethanolamine salts.

For a review on suitable salts see Berge et al, *J. Pharm. Sci.*, 1977, 66, 1–19.

The pharmaceutically acceptable solvates of the compounds of the formula (I) and salts thereof include the hydrates thereof.

Also included within the present scope of the compounds of the formula (I) and salts thereof are polymorphs and radiolabelled derivatives thereof.

A compound of the formula (I) may contain one or more additional asymmetric carbon atoms and therefore exist in two or more stereoisomeric forms. The present invention includes the individual stereoisomers of the compounds of the formula (I) and, where appropriate, the individual tautomers thereof, together with mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferably, $R^1$ is $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano.

Preferably, $R^1$ is $C_1$–$C_6$ alkyl substituted by 1 or 2 phenyl groups, said phenyl, groups being optionally substituted by $C_1$–$C_6$ alkyl, $C_1$–$C_6$ alkoxy, halo or cyano.

Preferably, $R^1$ is $C_1$–$C_6$ alkyl substituted by 1 or 2 phenyl groups.

Preferably, $R^1$ is $C_1$–$C_4$ alkyl substituted by 1 or 2 phenyl groups.

Preferably, $R^1$ is $C_1$–$C_2$ alkyl substituted by 1 or 2 phenyl groups.

Preferably, $R^1$ is diphenylethyl.

Preferably, $R^1$ is 2,2-diphenylethyl.

Preferably, $R^2$ is —$CH_2NHSO_2$—A—$R^3$, —$CONR^{10}$—$A^1$—$R^{11}$ or —X—$NR^{12a}$—Y—$NR^{13}R^{14}$.

Preferably, $R^2$ is —$CH_2NHSO_2CH_2CH(CH_3)_2$, —$CONHCH_2CH_2Ph$, —$CH_2NHCONHCH_2CH_2N[CH(CH_3)_2][cyclopentyl]$, —$CH_2NHCONHCH_2CH_2$(piperidin-1-yl) or —$CONHCH_2CH_2$(piperidin-1-yl).

Preferably, $R^2$ is —$CH_2NHSO_2CH_2CH(CH_3)_2$, —$CH_2NHCONHCH_2CH_2N[CH(CH_3)_2][cyclopentyl]$, or —$CH_2NHCONHCH_2CH_2$(piperidin-1-yl).

Preferably, $R^{19}$ is C-linked tetrazolyl, oxadiazolyl, oxazolyl or triazolyl each optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$.

Preferably, $R^{19}$ is C-linked tetrazolyl, oxadiazolyl, oxazolyl or triazolyl each optionally substituted by $C_1$–$C_6$ alkyl.

Preferably, $R^{19}$ is 1,2,3,4-tetrazol-5-yl, 1,2,4-oxadiazol-5-yl, 1,2,4-oxadiazol-3-yl, 1,2-oxazol-5-yl, 1,2,4-triazol-3-yl or 1,2,3-triazol-4-yl each optionally substituted by $C_1$–$C_6$ alkyl.

Preferably, $R^{19}$ is 1,2,3,4-tetrazol-5-yl, 1,2,4-oxadiazol-5-yl, 1,2,4-oxadiazol-3-yl, 1,2-oxazol-5-yl, 1,2,4-triazol-3-yl or 1,2,3-triazol-4-yl each optionally substituted by ethyl.

Preferably, $R^{19}$ is 2-ethyl-1,2,3,4-tetrazol-5-yl, 3-ethyl-1,2,4-oxadiazol-5-yl, 5-ethyl-1,2,4-oxadiazol-3-yl, 3-ethyl-1,2-oxazol-5-yl, 1-ethyl-1,2,4-triazol-3-yl or 1-ethyl-1,2,3-triazol-4-yl.

Preferably, $R^{19}$ is 3-ethyl-1,2,3,4-tetrazol-5-yl or 1-ethyl-1,2,3-triazol-4-yl.

Preferably, A is a bond, methylene or 1,2-propylene.
Preferably, $R^3$ is $C_1$–$C_6$ alkyl.
Preferably, $R^3$ is $C_1$–$C_4$ alkyl.
Preferably, $R^3$ is methyl, propyl or butyl.
Preferably, $R^3$ is methyl, prop-2-yl or 2-methylprop-1-yl.
Preferably, —A—$R^3$ is $C_1$–$C_6$ alkyl.
Preferably, —A—$R^3$ is $C_1$–$C_4$ alkyl.
Preferably, —A—$R^3$ is butyl.
Preferably, —A—$R^3$ is 2-methylprop-1-yl.
Preferably, $R^{10}$ is H.
Preferably, $A^1$ is $C_1$–$C_6$ alkylene.
Preferably, $A^1$ is $C_2$–$C_6$ alkylene.
Preferably, $A^1$ is $C_1$–$C_4$ alkylene.
Preferably, $A^1$ is $C_2$–$C_4$ alkylene.
Preferably, $A^1$ is $C_1$–$C_2$ alkylene.
Preferably, $A^1$ is ethylene.
Preferably, $A^1$ is 1,2-ethylene.
Preferably, $R^{11}$ is (i) phenyl optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$ or (ii) piperidin-1-yl optionally C-substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$.

Preferably, $R^{11}$ is phenyl or piperidin-1-yl.
Preferably, X is —$CH_2$—.
Preferably, $R^{12a}$ is H.
Preferably, Y is CO.
Preferably, $R^{13}$ is H.
Preferably, $R^{14}$ is —($C_2$–$C_6$ alkylene)-$NR^8R^9$.
Preferably, $R^{14}$ is —($C_2$–$C_4$ alkylene)-$NR^8R^9$.
Preferably, $R^{14}$ is -(ethylene)-$NR^8R^9$.
Preferably, $R^{14}$ is —$CH_2CH_2NR^8R^9$.
Preferably, either (i) $R^8$ and $R^9$, taken together with the nitrogen atom to which they are attached, represent piperidinyl, said piperidinyl being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or (ii) $R^8$ is $C_1$–$C_6$ alkyl and $R^9$ is $C_3$–$C_8$ cycloalkyl.

Preferably, either $R^8$ and $R^9$, taken together with the nitrogen atom to which they are attached, represent piperidinyl, or $R^8$ is $C_1$–$C_3$ alkyl and $R^9$ is $C_3$–$C_5$ cycloalkyl.

Preferably, either $R^8$ and $R^9$, taken together with the nitrogen atom to which they are attached, represent piperidinyl, or $R^8$ is propyl and $R^9$ is cyclopentyl.

Preferably, either $R^8$ and $R^9$, taken together with the nitrogen atom to which they are attached, represent piperidinyl, or $R^8$ is prop-2-yl and $R^9$ is cyclopentyl.

Preferred examples of compounds of the formula (I) include those of the Examples section hereafter, especially Examples 9, 10 and 11, and the pharmaceutically acceptable salts and solvates thereof.

The compounds of the formula (I) can be prepared by conventional routes such as by the procedures described in the general methods presented below or by the specific methods described in the Examples section, or by similar methods thereto. The present invention also encompasses these processes for preparing the compounds of formula (I), in addition to any novel intermediates used therein. In the general methods described, $R^1$, $R^2$ and $R^{19}$ are as previously defined unless otherwise stated.

1. All the compounds of formula (I) may be prepared by the deprotection of a compound of formula

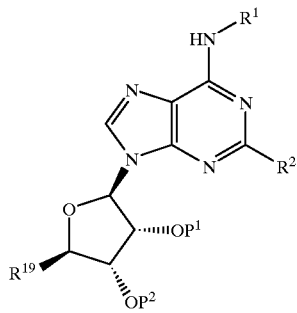

(II)

wherein $P^1$ and $P^2$ represent suitable protecting groups which may be the same or different or $P^1$ and $P^2$, when taken together, represent a suitable protecting group. Examples of suitable protecting groups will be apparent to the skilled person [see for instance 'Protecting Groups in Organic Synthesis (Second Edition)', Theodora W. Green and Peter G. M. Wuts, John Wiley and Sons, 1991]. Preferred individual protecting groups are silyl (substituted with three groups independently selected from aryl and alkyl), alkanoyl and aroyl. A preferred protecting group where $P^1$ and $P^2$ form part of the same protecting group is where $P^1$ and $P^2$ taken together are $C_1$–$C_6$ alkylene. Particularly preferred individual protecting groups are acetyl and benzoyl. A particularly preferred protecting group where $P^1$ and $P^2$ form part of the same protecting group is where $P^1$ and $P^2$ taken together are 1,1-dimethylmethylene. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ an $P^2$ are each acetyl, the protecting groups may be removed by treating a solution of the compound of formula (II) in a suitable solvent, such as a mixture of water and methanol, with a base such as sodium carbonate, typically at room temperature.

The protecting groups $P^1$ and $P^2$ may be removed together in a single step or sequentially, in either order.

Compounds of the formula (II) may be prepared by the reaction of a derivatised form of a compound of the formula

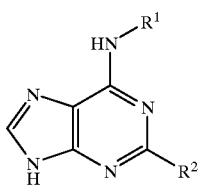
(III)

with a compound of the formula

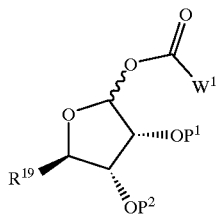
(IV)

wherein $W^1$ is methyl or phenyl and $P^1$ and $P^2$ are as defined above. In a typical procedure, the compound of the formula (III) is heated with N,O-bis(trimethylacetamide) in an inert solvent such as 1,1,1-trichloroethane, the solvent is removed and a solution of the residue, in a suitable solvent such as toluene, is heated, preferably under reflux, with the compound of the formula (IV) and trimethylsilyltriflate.

Compounds of the formula (III) may be prepared by the deprotection of a compound of the formula

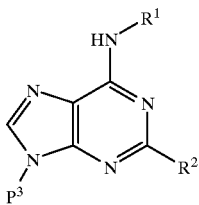
(V)

in which $P^3$ is a suitable protecting group. Examples of suitable protecting groups will be apparent to the skilled person [see for instance 'Protecting Groups in Organic Synthesis (Second Edition)', Theodora W. Green and Peter G. M. Wuts, John Wiley and Sons, 1991]. A preferred protecting group is that in which $P^3$ represents tetrahydropyran-2-yl. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^3$ is tetrahydropyran-2-yl, the protecting group may be removed by treating a solution of the compound of the formula (V) in a suitable solvent, such as ethanol, with an acid such as hydrochloric acid.

Compounds of the formula (V) may be prepared by the routes shown in Schemes 1 to 5 in which $L^x$ is a suitable leaving group, preferably chloro, $A^2$ is an activating group, as defined below, $P^3$ is a suitable protecting group, as defined above, and E is $C_1-C_6$ alkyl.

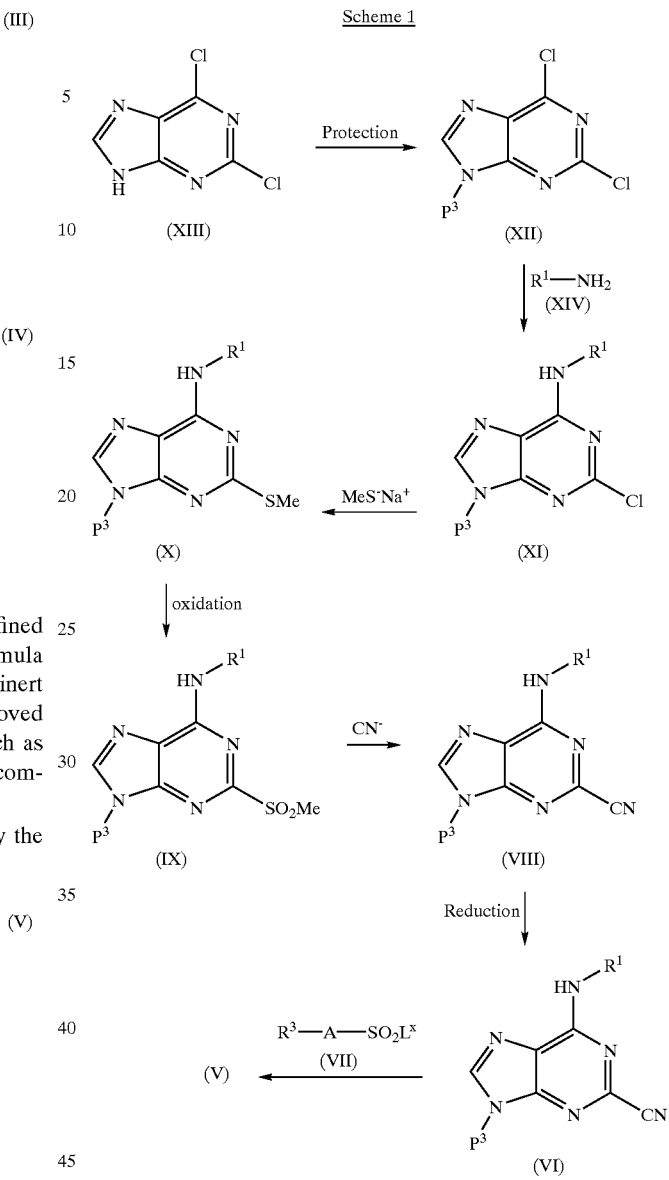

Scheme 1

As shown in Scheme 1, compounds of the formula (V) in which $R^2$ is —$CH_2NHSO_2$—A—$R^3$ may be prepared by the reaction of a compound of the formula (VI) with a compound of the formula (VII). In a typical procedure, a solution of the compound of the formula (VI) in a suitable inert solvent such as dichloromethane is treated with the compound of the formula (VII). An acid acceptor such as triethylamine may optionally be added. Compounds of the formula (VI) may be prepared by the reduction of a compound of the formula (VIII). The reduction may be carried out with any suitable hydride reducing agent or by hydrogenation. In a typical procedure, a solution of the compound of the formula (VIII) in a suitable solvent such as ethanol is saturated with ammonia gas, treated with an appropriate hydrogenation catalyst such as Pearlman's catalyst and pressurised with hydrogen, preferably to about 414 kPa (60 psi). Compounds of the formula (VIII) may be prepared by reacting a compound of the formula (IX) with a source of cyanide anion such as potassium cyanide. The reaction is typically carried out in a solvent such as N,N-dimethylformamide at an elevated temperature. Compounds of the formula (IX) may be prepared by the oxidation of a compound of the formula (X). In a typical procedure, an aqueous solution of potassium peroxymonosulphate is added to a solution of the compound of the formula (X) and sodium hydrogencarbonate in a suitable solvent, such as a mixture of water and acetone. Compounds of the formula (X) may be prepared by the displacement of chloride in a compound of the formula (XI) with thiomethoxide. Typically, the reaction is carried out in a polar solvent such as N,N-dimethylformamide, at elevated temperatures and under an atmosphere of nitrogen. Thiomethoxide is used as an alkali metal salt such as sodium thiomethoxide. Compounds of the formula (XI) may be prepared by the reaction of a compound of the formula (XII) with a compound of the formula (XIV). Typically, a solution of the dichloropurine (XII) in a suitable solvent such as isopropyl alcohol is treated with the compound of the formula (XIV) and heated under reflux. An additional acid acceptor such as N,N-diphenyl-N-ethylamine may optionally be added. Compound (XII) may be prepared by the protection of 2,6-dichloro-9H-purine (XIII). Suitable conditions for the protection are well known in the art [see for instance 'Protecting Groups in Organic Synthesis (Second Edition)', Theodora W. Green and Peter G. M. Wuts, John Wiley and Sons, 1991]. In a typical procedure, where $P^3$ is tetrahydropyran-2-yl, a solution of 2,6-dichloro-9H-purine (XIII) in a suitable solvent such as ethyl acetate is treated with dihydropyran and an acid catalyst such as 4-toluenesulphonic acid, usually at an elevated temperature.

Scheme 2

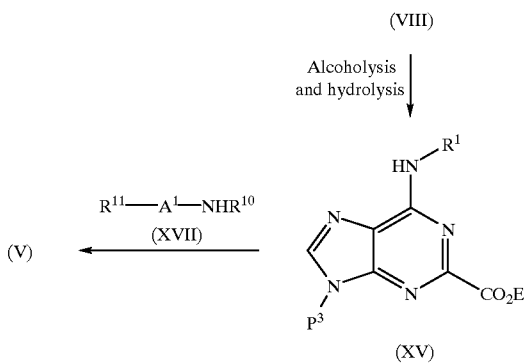

As shown in Scheme 2, compounds of the formula (V) in which $R^2$ is —$CONR^{10}$—$A^1$—$R^{11}$ may be prepared by the reaction of a compound of the formula (XV) with a compound of the formula (XVII), preferably at an elevated temperature, most preferably at from 100 to 150° C. In a typical procedure, the compound of the formula (XV) and the compound of the formula (XVII) are heated together at 130° C. Compounds of the formula (XV) may be prepared by the sequential alcoholysis and hydrolysis of a compound of the formula (VIII). In a typical procedure, a solution of the compound of the formula (VIII) in an alcoholic solvent EOH (wherein E is as defined above) is treated with the sodium alkoxide of the formula EONa (wherein E is as defined above) and heated under reflux. The resulting mixture is cooled and evaporated and the resulting residue is dissolved in a suitable solvent such as a mixture of tetrahydrofuran and water (e.g. a 3:1 mixture thereof) and treated with an acid such as acetic acid. The resulting mixture is heated at an elevated temperature, preferably under reflux, to give the compound of the formula (XV).

Scheme 3

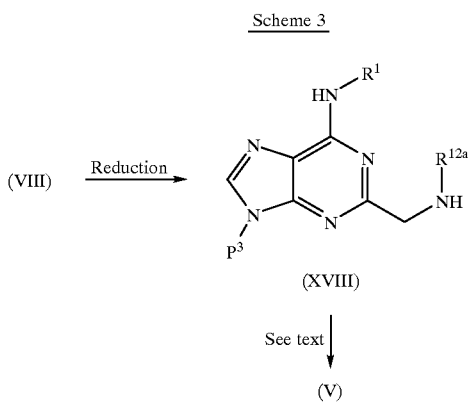

See text (V)

As shown in Scheme 3, compounds of the formula (V) in which $R^2$ is —$CH_2$—$NR^{12a}$—Y—$NR^{13}R^{14}$ may be prepared the reaction of a compound of the formula (XVIII) with an appropriate reagent, as described below.

Compounds of the formula (V) in which $R^2$ is —$CH_2$—$NR^{12a}$—CO—$NR^{13}R^{14}$ may be prepared by the reaction of a compound of the formula (XIX)

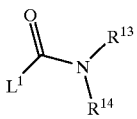

in which $L^1$ is a suitable leaving group, with a compound of the formula (XVIII) in a suitable solvent, such as a mixture of toluene and isopropanol, optionally at an elevated temperature, e.g. under reflux. The leaving group $L^1$ is preferably halo (e.g. chloro) or imidazol-1-yl, most preferably imidazol-1-yl. Compounds of the formula (XIX) wherein $L^1$ is imidazol-1-yl may be prepared by the reaction of a compound of the formula $R^{13}R^{14}NH$ (XX)

with 1,1'-carbonyldiimidazole. In a typical reaction a compound of the formula (XX) is added to a solution of 1,1'-carbonyldiimidazole in a suitable solvent such as dichloromethane. Compounds of the formula (XX) are either commercially available or may be prepared by standard techniques well known to persons skilled in the art.

Compounds of the formula (V) in which $R^2$ is —$CH_2$—$NR^{12a}$—CS—$NR^{13}R^{14}$ may be prepared by the reaction of a compound of the formula $L^2L^3C$=S (XXI)

in which $L^2$ and $L^3$ are suitable leaving groups, with a compound of the formula (XVIII) followed by the addition of a compound of the formula (XX). The leaving groups $L^2$ and $L^3$ may be the same or different and are typically each either —$S(C_1-C_6$ alkyl) or imidazol-1-yl. Preferably, $L^2$ and $L^3$ are each methylthio or imidazol-1-yl. In a typical procedure, a solution of the compound of the formula (XVIII) in a suitable solvent, such as ethanol, is treated with the compound of the formula (XXI), preferably at an elevated temperature, most preferably under reflux. When analysis by thin layer chromatography shows that a substantially complete reaction has occurred, a compound of the formula (XX) is added and the reaction mixture is preferably heated, most preferably under reflux Compounds of the formula (V) in which $R^2$ is —$CH_2$—$NR^{12a}$—$SO_2$—$NR^{13}R^{14}$ may be prepared by the reaction of a compound of the formula $$R^{13}R^{14}NSO_2L^4 \quad (XXII)$$

in which $L^4$ is a suitable leaving group, typically halo, with a compound of the formula (XVIII), optionally in the presence of an acid acceptor. Preferably, $L^4$ is chloro. In a typical example, a solution of the compound of the formula (XVIII) in a suitable solvent, such as pyridine, is treated with the compound of the formula (XXII) and preferably heated, most preferably at about 90° C. Compounds of the formula (XXII) may be prepared by treating a compound of the formula $$R^{13}R^{14}NSO_3H \quad (XXIII)$$

with an activating agent. In a typical example, where $L^4$ is chloro, a solution of a compound of the formula (XXIII), in a suitable solvent such as toluene, is treated with $PCl_5$ and heated, preferably under reflux. Compounds of the formula (XXIII) may be prepared by treating a compound of the formula (XX) with chlorosulphonic acid. In a typical procedure, a solution of the compound of the formula (XX) in a suitable solvent, such as dichloromethane, is treated with chlorosulphonic acid, optionally in the presence of a proton acceptor such as triethylamine.

Compounds of the formula (V) in which $R^2$ is —$CH_2$—$NR^{12a}$—C=N(CN)—$NR^{13}R^{14}$ may be prepared by the reaction of a compound of the formula $$L^5L^6C=N(CN) \quad (XXIV)$$

in which $L^5$ and $L^6$ are suitable leaving groups, with a compound of the formula (XVIII), followed by the addition of a compound of the formula (XX). The leaving groups $L^5$ and $L^6$ may be the same or different and are typically each selected from halo and —S($C_1$–$C_6$ alkyl). Preferably, $L^5$ and $L^6$ are each methythio. In a typical procedure, where $L^5$ and $L^6$ are each methylthio, a solution of the compound of the formula (XVIII) in a suitable solvent, such as ethanol, is treated with dimethylcyanothioimidocarbamate, preferably at room temperature. When a substantially complete reaction is indicated by thin layer chromatography (TLC), a compound of the formula (XX) is added and the reaction mixture is preferably heated, most preferably under reflux.

Compounds of the formula (XVIII) may be prepared by the reduction of a compound of the formula (VIII) with a suitable reducing agent, preferably a palladium catalyst and hydrogen gas, in the presence of a compound of the formula $$R^{12a}NH_2 \quad (XXV).$$

In a typical procedure, where $R^{12a}$ is H, a compound of the formula (VIII) is dissolved in a suitable solvent, such as ethanol, which has been saturated with ammonia gas, a palladium catalyst such as 10% w/w palladium on carbon is added and the reaction mixture is stirred under an atmosphere of hydrogen gas, typically at a pressure of 414 kPa (60 psi). Compounds of the formula (XXV) are either commercially available or easily prepared by methods well known in the art.

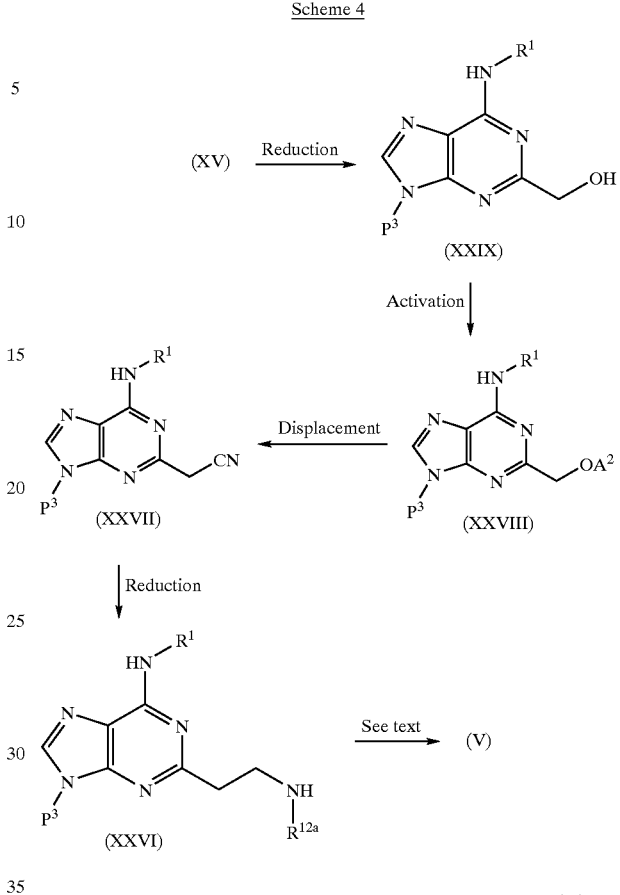

As shown in Scheme 4, compounds of the formula (V) in which $R^2$ is —$CH_2CH_2$—$NR^{12a}$—Y—$NR^{13}R^{14}$ may be prepared the reaction of a compound of the formula (XXVI) with an appropriate reagent. The methods and reagents used are the same as those used to prepare compounds of the formula (V) from a compound of the formula (XVIII). Compounds of the formula (XXVI) may be prepared by the reduction of a compound of the formula (XXVII) with a suitable reducing agent in the presence of a compound of the formula (XXV). A preferred reducing agent is Raney nickel, optionally in the presence of hydrogen gas. In a typical procedure, where $R^{12a}$ is H, the compound of the formula (XXVII) is dissolved in a suitable solvent, such as ethanol, which has been saturated with ammonia gas, Raney nickel is added and the reaction mixture is shaken, preferably at room temperature. Compounds of the formula (XXVII) may be prepared by the displacement of a leaving group 'OA²', in which $A^2$ is an activating group, from a compound of the formula (XXVIII) with cyanide anion. In a typical example, a solution of the compound of the formula (XXVIII) in a suitable solvent, such as N,N-dimethylformamide, is treated with a source of cyanide ion, such as potassium cyanide to give the compound of the formula (XXVII). Examples of suitable choices for $A^2$ will be apparent to the skilled man [see for example 'Advanced Organic Chemistry (Third Edition)', Jerry March, Wiley-Interscience, 1985]. Preferably, $A^2$ is ($C_1$–$C_6$)alkylsulphonyl, phenylsulphonyl or ($C_1$–$C_6$)alkylphenylsulphonyl. Most preferably, $A^2$ is methylsulphonyl. Compounds of the formula (XXVIII) may be prepared by the activation of the free hydroxyl in a compound of the formula (XXIX). In a typical procedure, where $A^2$ is methylsulphonyl, a solution of the compound of the formula (XXIX) in a suitable solvent, such as dichloromethane, is treated with methanesulphonyl chloride in the presence of a proton acceptor such as triethylamine. Compounds of the formula (XXIX) may be prepared by the reduction of an ester of the formula (XV) with a suitable reducing agent, such as lithium borohydride, in a suitable solvent, such as tetrahydrofuran.

Scheme 5

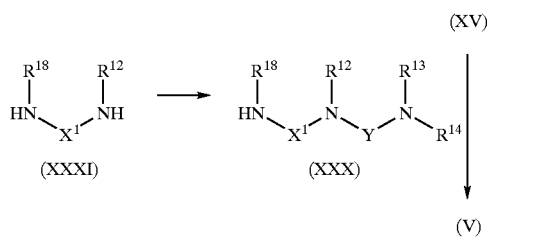

As shown in Scheme 5, compounds of the formula (V) in which $R^2$ is —CO—$NR^{18}$—$X^1$—$NR^{12}$—Y—$NR^{13}R^{14}$ may be prepared by the reaction of a compound of the formula (XV) with a compound of the formula (XXX), optionally at an elevated temperature, optionally in an inert solvent such as 1,2-dimethoxyethane or 2-methoxyethyl ether and optionally under pressure. Preferably the reaction is carried out in the absence of solvent at a temperature of from 100–120° C. Compounds of the formula (XXX) may be prepared by the reaction of a compound of the formula (XXXI) with an appropriate reagent and under suitable conditions in the same way that a compound of the formula (V) may be prepared from a compound of the formula (XVIII). The skilled person will appreciate that in order to achieve the desired degree of regioselectivity, a suitable protecting group (e.g. trifluoroacetyl) may optionally be used for this reaction located on a chosen N atom of a compound of the formula (XXXI). Compounds of the formula (XXXI) may be prepared by conventional procedures.

2. Compounds of the formula (I) in which in which $R^2$ is —$CH_2NHSO_2$—A—$R^3$ may be prepared by the reaction of a compound of the formula

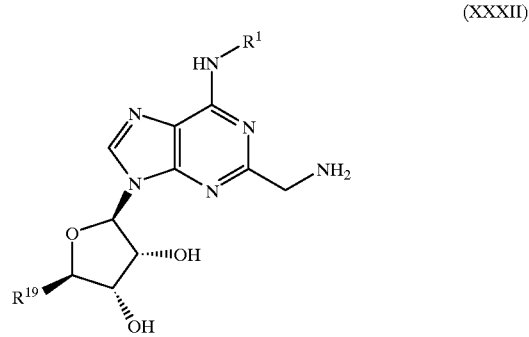

with a compound of the formula (VII) in which $L^x$ is as defined above. In a typical procedure, a solution of the compound of the formula (XXXII) in a suitable inert solvent such as dichloromethane is treated with the compound of the formula (VII). An acid acceptor such as triethylamine may optionally be added.

Compounds of the formula (XXXII) may be prepared by the route shown in Scheme 6 in which $P^1$ and $P^2$ are as defined above.

Scheme 6

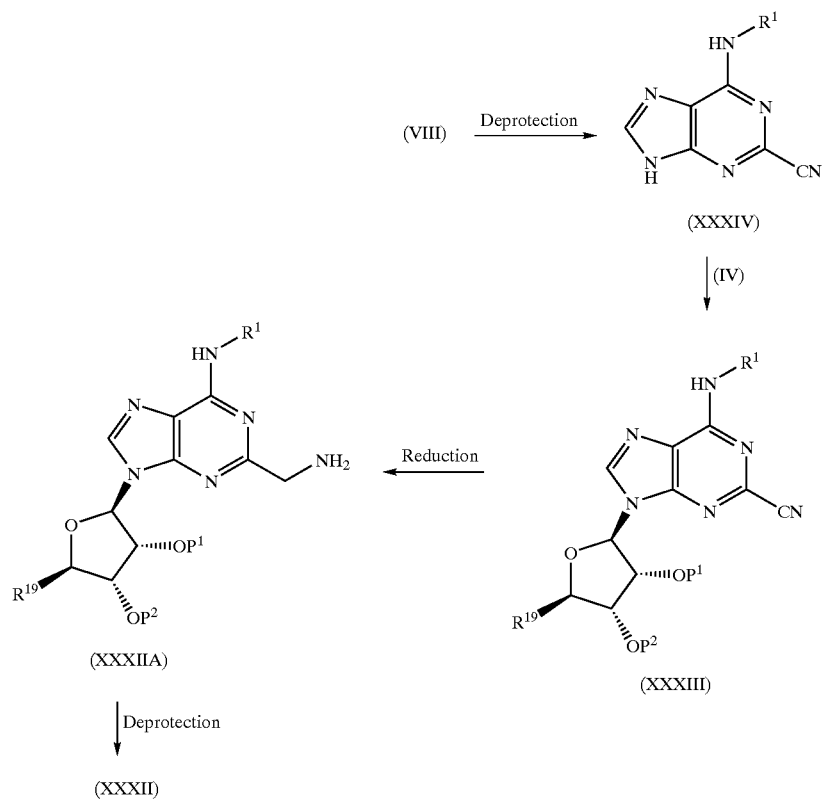

In Scheme 6, compounds of the formula (XXXII) may be prepared by the deprotection of a compound of the formula (XXXIIA). Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$ are each acetyl, the protecting groups may be removed by treating a solution of the compound of formula (XXXIIA) in a suitable solvent, such as a mixture of water and methanol, with a base such as sodium carbonate, typically at room temperature. Compounds of the formula (XXXIIA) may be prepared by the reduction of a compound of the formula (XXXIII). The reduction may be carried out with any suitable hydride reducing agent or by hydrogenation. In a typical procedure, a solution of the compound of the formula (XXXIII) in a suitable solvent such as ethanol is saturated with ammonia gas, treated with an appropriate hydrogenation catalyst such as Pearlman's catalyst and pressurised with hydrogen, preferably to about 414 kPa (60 psi). In certain cases, protecting groups $P^1$ and $P^2$ will be removed by the conditions employed in the reduction of a compound of the formula (XXXIII) and a compound of the formula (XXXII) will be obtained directly. Compounds of the formula (XXXIII) may be prepared by the reaction of a derivatised form of a compound of the formula (XXXIV) with a compound of the formula (IV), in which $W^1$ is as defined above. In a typical procedure, the compound of the formula (XXXIV) is heated with N,O-bis(trimethylacetamide) in an inert solvent such as 1,1,1-trichloroethane, the solvent is removed and a solution of the residue, in a suitable solvent such as toluene, is heated, preferably under reflux, with the compound of the formula (IV) and trimethylsilyltriflate. Compounds of the formula (XXXIV) may be prepared by the deprotection of a compound of the formula (VIII), in which $P^3$ is as defined above. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^3$ is tetrahydropyran-2-yl, the protecting group may be removed by treating a solution of the compound of the formula (VIII) in a suitable solvent, such as ethanol, with an acid such as hydrochloric acid.

3. Compounds of the formula (I) in which in which $R^2$ is —$CH_2$—$NR^{12a}$—Y—$NR^{13}R^{14}$ may be prepared by the reaction of a compound of the formula

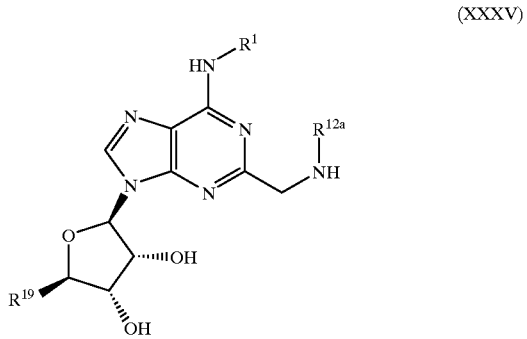

(XXXV)

with an appropriate reagent and under appropriate conditions in the same way that a compound of the formula (V) may be prepared from a compound of the formula (XVIII). It will be appreciated by the skilled man that in the case where Y is —CS— or —C=N(CN)—, the final intermediates will be compounds of the formula (XXXVI) and (XXXVII), respectively, in which $L^7$ represents either of $L^2$ or $L^3$ and $L^8$ represents either of $L^5$ or $L^6$.

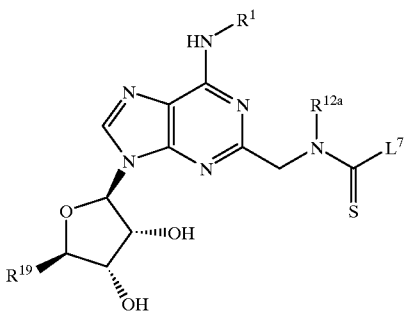

(XXXVI)

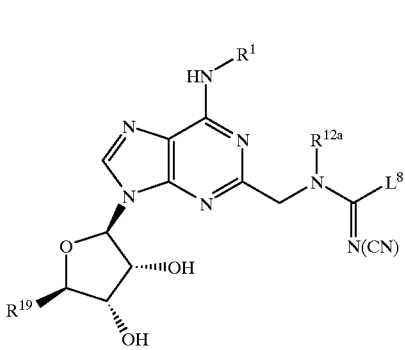

(XXXVII)

Compounds of the formula (XXXV) may be prepared by the reduction of a compound of the formula (XXXIII) with a suitable reducing agent, preferably a palladium catalyst and hydrogen gas, in the presence of a compound of the formula (XXV), and subsequent deprotection of the product so obtained in cases where the protecting groups $P^1$ and $P^2$ are not removed by the conditions employed for the reduction. In a typical procedure, where $R^{12a}$ is H, a compound of the formula (XXXIII) is dissolved in a suitable solvent, such as ethanol, which has been saturated with ammonia gas, a palladium catalyst such as 10% w/w palladium on carbon is added and the reaction mixture is stirred under an atmosphere of hydrogen gas, typically at a pressure of 414 kPa (60 psi).

4. Compounds of the formula (I) in which $R^2$ is —$CH_2$—$NR^{12a}$—CO—$NR^{13}R^{14}$ may be prepared by the reaction of a compound of the formula (XXXV) with a compound of the formula $L^9COL^{10}$ (XXXVIII)

in which $L^9$ and $L^{10}$ are suitable leaving groups to form an intermediate of the formula

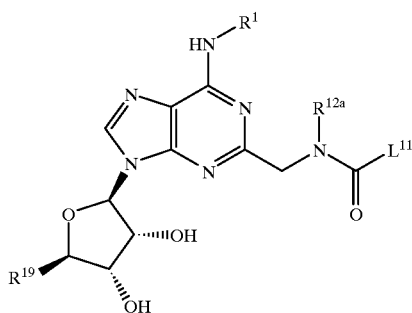

(XXXIX)

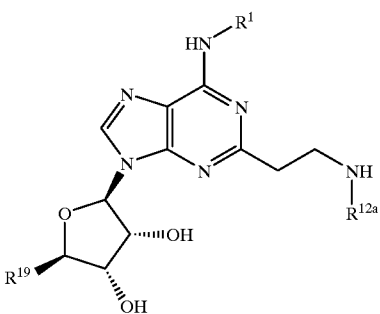

(XXXXII)

in which L$^{11}$ represents either of the leaving groups L$^9$ or L$^{10}$ and the subsequent reaction of this intermediate with a compound of the formula (XX). Preferably, L$^9$ and L$^{10}$ are each either halo or imidazol-1-yl. Most preferably L$^9$ and L$^{10}$ are each imidazol-1-yl. In a typical example, where L$^9$ and L$^{10}$ are each imidazol-1-yl, a solution of the compound of the formula (XXXV) in a suitable solvent, such as dichloromethane, is treated with 1,1'-carbonyldiimidazole. The reaction mixture is stirred, preferably at room temperature, until thin layer chromatography (TLC) indicates that a substantially complete reaction has occurred and then a compound of the formula (XX) is added to give the compound of the formula (I).

5. Compounds of the formula (I) in which R$^2$ is —CH$_2$—NR$^{12a}$—CS—NR$^{13}$R$^{14}$ may be prepared by the reaction of a compound of the formula (XXXV) with a compound of the formula

  (XXXX)

in which L$^{12}$ is a suitable leaving group, preferably methylthio or imidazol-1-yl. The reaction is preferably carried out in a suitable solvent, such as ethanol, and at an elevated temperature, most preferably under reflux. Compounds of the formula (XXXX) are readily prepared from a compound of the formula (XX) by methods known to the skilled man.

6. Compounds of the formula (I) in which R$^2$ is —CH$_2$—NR$^{12a}$—C=N(CN)—NR$^{13}$R$^{14}$ may be prepared by the reaction of a compound of the formula (XXXV) with a compound of the formula

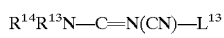  (XXXXI)

in which L$^{13}$ is a suitable leaving group, preferably methylthio. The reaction is preferably carried out in a suitable solvent, such as ethanol, and at an elevated temperature, most preferably under reflux. Compounds of the formula (XXXXI) are readily prepared from a compound of the formula (XX) by methods known to the skilled man.

7. Compounds of the formula (I) in which in which R$^2$ is —CH$_2$CH$_2$—NR$^{12a}$—Y—NR$^{13}$R$^{14}$ may be prepared by the reaction of a compound of the formula with an appropriate reagent and under appropriate conditions in the same way that a compound of the formula (V) may be prepared from a compound of the formula (XVIII). It will be appreciated by the skilled man that in the case where Y is —CS— or —C=N(CN)—, the final intermediates will be compounds of the formula (XXXXIII) and (XXXXIV), respectively, in which L$^{14}$ represents either of L$^2$ or L$^3$ and L$^{15}$ represents either of L$^5$ or L$^6$.

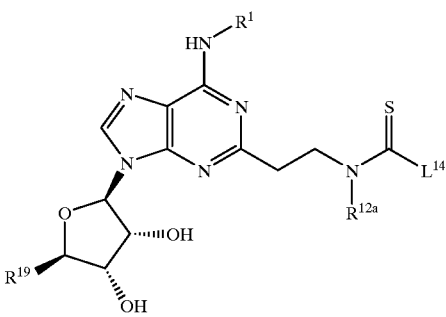

(XXXXIII)

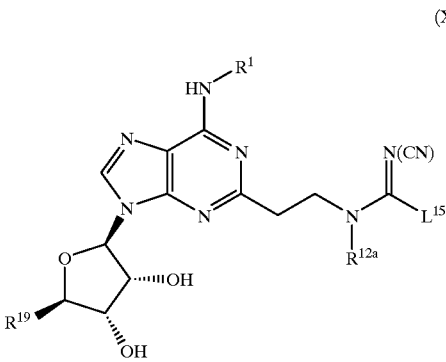

(XXXXIV)

Compounds of the formula (XXXXII) may be prepared as shown in Scheme 7, in which P$^1$ and P$^2$ are as defined above.

Scheme 7

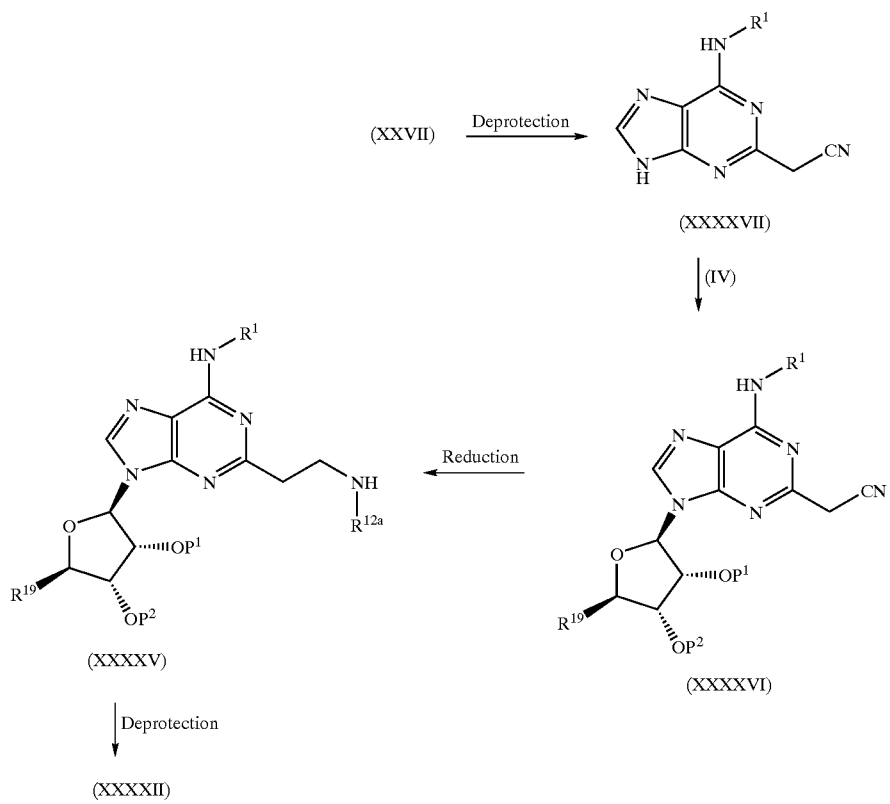

In Scheme 7, compounds of the formula (XXXXII) may be prepared by the deprotection of a compound of the formula (XXXXV). Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$ are each acetyl, the protecting groups may be removed by treating a solution of the compound of formula (XXXXV) in a suitable solvent, such as a mixture of water and methanol, with a base such as sodium carbonate, typically at room temperature. Compounds of the formula (XXXXV) may be prepared by the reduction of a compound of the formula (XXXXVI) with a suitable reducing agent, preferably a palladium catalyst and hydrogen gas, in the presence of a compound of the formula (XXV). In a typical procedure, where $R^{12a}$ is H, a compound of the formula (XXXXVI) is dissolved in a suitable solvent, such as ethanol, which has been saturated with ammonia gas, a palladium catalyst such as 10% w/w palladium on carbon is added and the reaction mixture is stirred under an atmosphere of hydrogen gas, typically at a pressure of 414 kPa (60 psi). Compounds of the formula (XXXXVI) may be prepared by the reaction of a derivatised form of a compound of the formula (XXXXVII) with a compound of the formula (IV), in which $W^1$ is as defined above. In a typical procedure, the compound of the formula (XXXXVII) is heated with N,O-bis(trimethylacetamide) in an inert solvent such as 1,1,1-trichloroethane, the solvent is removed and a solution of the residue, in a suitable solvent such as toluene, is heated, preferably under reflux, with the compound of the formula (IV) and trimethylsilyltriflate. Compounds of the formula (XXXXVII) may be prepared by the deprotection of a compound of the formula (XXVII), in which $P^3$ is as defined above. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^3$ is tetrahydropyran-2-yl, the protecting group may be removed by treating a solution of the compound of the formula (XXVII) in a suitable solvent, such as ethanol, with an acid such as hydrochloric acid.

8. Compounds of the formula (I) in which $R^2$ is —$CH_2CH_2$—$NR^{12a}$—CO—$NR^{13}R^{14}$ may be prepared by the reaction of a compound of the formula (XXXXII) with a compound of the formula (XXXVIII) in which $L^9$ and $L^{10}$ are as defined above to form an intermediate of the formula (XXXXVIII)

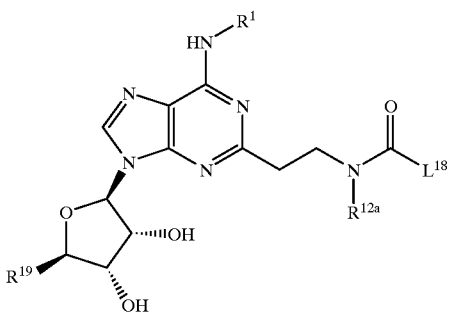

in which $L^{18}$ represents either of the leaving groups $L^9$ or $L^{10}$ and the subsequent reaction of this intermediate with a compound of the formula (XX). In a typical example, where $L^9$ and $L^{10}$ are each imidazol-1-yl, a solution of the compound of the formula (XXXXII) in a suitable solvent, such as dichloromethane, is treated with 1,1'-carbonyldiimidazole. The reaction mixture is stirred, preferably at room temperature, until thin layer chromatography (TLC) indicates that a substantially complete reaction has occurred and then a compound of the formula (XX) is added to give the compound of the formula (I).

9. Compounds of the formula (I) in which $R^2$ is —$CH_2CH_2$—$NR^{12a}$—CS—$NR^{13}R^{14}$ may be prepared by the reaction of a compound of the formula (XXXXII) with a compound of the formula (XXXX) in which $L^{12}$ is as defined above. The reaction is preferably carried out in a suitable solvent, such as ethanol, and at an elevated temperature, most preferably under reflux.

10. Compounds of the formula (I) in which $R^2$ is —$CH_2CH_2$—$NR^{12a}$—C=N(CN)—$NR^{13}R^{14}$ may be prepared by the reaction of a compound of the formula (XXXXII) with a compound of the formula (XXXXI) in which $L^{13}$ is as defined above. The reaction is preferably carried out in a suitable solvent, such as ethanol, and at an elevated temperature, most preferably under reflux.

11. Compounds of the formula (I) in which in which $R^2$ is —$CONR^{10}$—$A^1$—$R^{11}$ may be prepared by the reaction of a compound of the formula

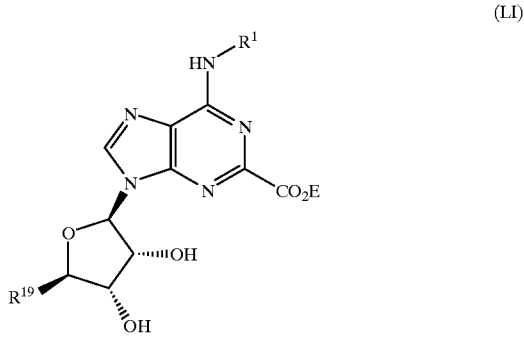

(LI)

in which E is as defined above, with a compound of the formula (XVII). The reaction is preferably carried out at an elevated temperature, most preferably at from 100 to 150° C., and optionally in the presence of a suitable solvent, such as ethanol. In a typical procedure, the compound of the formula (LI) and the compound of the formula (XVII) are heated together at about 120° C. Compounds of the formula (LI) may be prepared as shown in Scheme 8, in which $P^1$, $P^2$ and E are as defined above.

Scheme 8

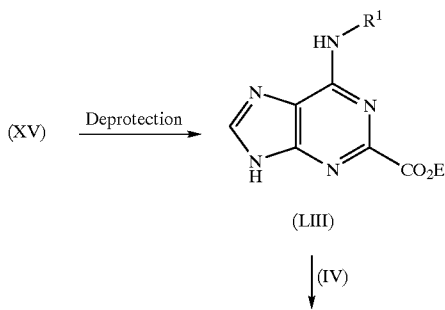

(XV) →Deprotection→ (LIII)

↓(IV)

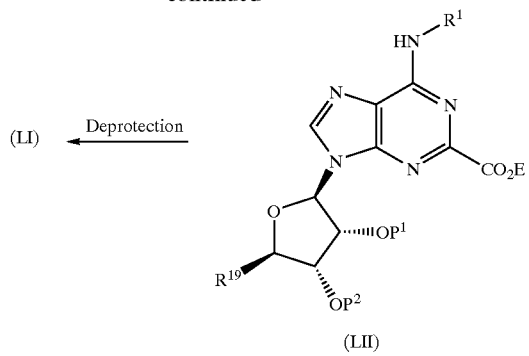

(LII) →Deprotection→ (LI)

In Scheme 8, compounds of the formula (LI) may be prepared by the deprotection of a compound of the formula (LII). Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$ are each acetyl, the protecting groups may be removed by treating a solution of the compound of formula (LII) in a suitable solvent, such as a mixture of water and methanol, with a base such as sodium carbonate, typically at room temperature. Compounds of the formula (LII) may be prepared by the reaction of a derivatised form of a compound of the formula (LIII) with a compound of the formula (IV), in which $W^1$ is as defined above. In a typical procedure, the compound of the formula (LII) is heated with N,O-bis(trimethylacetamide) in an inert solvent such as 1,1,1-trichloroethane, the solvent is removed and a solution of the residue, in a suitable solvent such as toluene, is heated, preferably under reflux, with the compound of the formula (IV) and trimethylsilyltriflate. Compounds of the formula (LIII) may be prepared by the deprotection of a compound of the formula (XV), in which $P^3$ is as defined above. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^3$ is tetrahydropyran-2-yl, the protecting group may be removed by treating a solution of the compound of the formula (XV) in a suitable solvent, such as ethanol, with an acid such as hydrochloric acid.

In certain cases, compounds of the formula (I) in which $R^2$ is —$CONR^{10}$—$A^1$—$R^{11}$ may be prepared by the reaction of a compound of the formula (LII) with a compound of the formula (XVII). In such cases, the protecting groups $P^1$ and $P^2$ are removed by the reaction conditions employed. For example, when $P^1$ and $P^2$ are each acetyl, the reaction of a compound of the formula (LII) with a compound of the formula (XVII) at 130° C. and in the absence of solvent gives a compound of the formula (I).

12. Compounds of the formula (I) in which $R^2$ is —$CONR^{10}$—$A^1$—$R^{11}$ may be prepared by the reaction of a compound of the formula

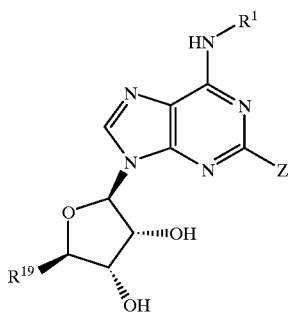

(LIV)

in which Z is a suitable leaving group such as bromo, iodo, trialkylstannyl or trifluoromethylsulphonyl, preferably iodo, with a compound of the formula (XVII) in the presence of carbon monoxide and a suitable catalyst. Preferably the catalyst is a palladium (II) catalyst. More preferably, the catalyst is 1,1'-bis(diphenylphosphino) ferrocenedichloropalladium (II) (optionally as a 1:1 complex with dichloromethane). Alternatively, palladium (II) acetate may be used in the presence of a suitable ligand such as 1,1'-bis(diphenylphosphino)ferrocene, triphenylphosphine, tri(o-tolyl)phosphine or (R)—, (S)— or racemic 2,2'-bis(diphenylphosphino)-1-1'-binaphthyl. In a typical procedure, the reaction is carried out in a sealed vessel in the presence of carbon monoxide (e.g. about 345 kPa, 50 psi) at an elevated temperature (e.g. about 60° C.) and in a suitable solvent (e.g. tetrahydrofuran, methanol or ethanol). A suitable organic base such as a tertiary amine (e.g. triethylamine, N-ethyldiisopropylamine or 4-methylmorpholine) may optionally be added.

Compounds of the formula (LIV) may be prepared as shown in Scheme 9, in which $P^1$, $P^2$ and Z are as defined above.

Scheme 9

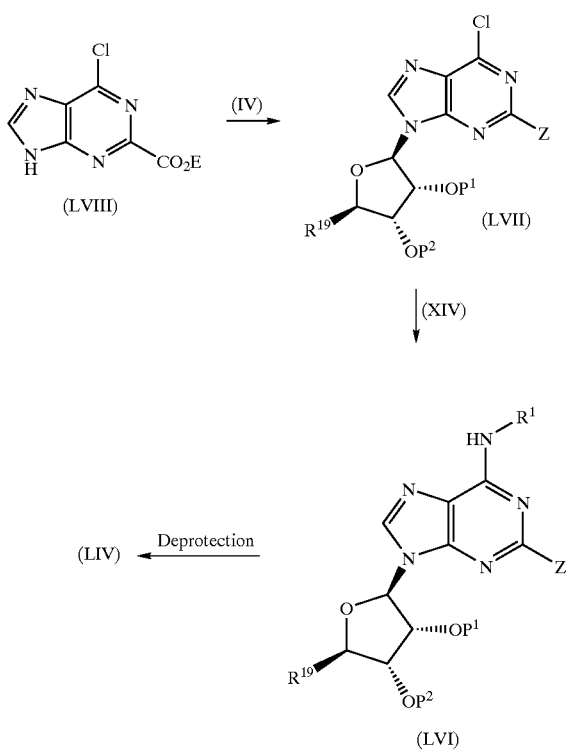

In Scheme 9, compounds of the formula (LIV) may be prepared by the deprotection of a compound of the formula (LVI). Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$ are each acetyl, the protecting groups may be removed by treating a solution of the compound of the formula (LVI) in a suitable solvent, such as a mixture of water and methanol, with a base such as sodium carbonate, typically at room temperature. Compounds of the formula (LVI) may be prepared by the reaction of a compound of the formula (LVII) with a compound of the formula (XIV). Typically, a solution of the compound of the formula (LVII) in a solvent such as isopropyl alcohol is treated with the compound of the formula (XIV) and heated under reflux. An additional acid acceptor such as N,N-diphenylethylamine may optionally be added. In certain cases, the protecting groups $P^1$ and $P^2$ may be removed by these conditions to give a compound of the formula (LIV) directly from a compound of the formula (LVII). Compounds of the formula (LVII) may be prepared by the reaction of a derivatised form of a compound of the formula (LVIII) with a compound of the formula (IV), in which $W^1$ is as defined above. In a typical procedure, the compound of the formula (LVIII) is heated with N,O-bis (trimethylacetamide) in an inert solvent such as 1,1,1-trichloroethane, the solvent is removed and a solution of the residue, in a suitable solvent such as toluene, is heated, preferably under reflux, with the compound of the formula (IV) and trimethylsilyltriflate. Compounds of the formula (LVIII) are either known or easily prepared by methods well known to the skilled man.

13. Compounds of the formula (I) in which $R^2$ is —CO—$NR^{18}$—$X^1$—$NR^{12}$—Y—$NR^{13}R^{14}$ may be prepared by the reaction of a compound of the formula

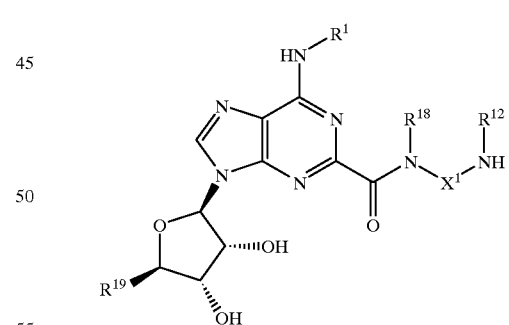

(LIX)

with an appropriate reagent and under appropriate conditions in the same way that a compound of the formula (V) may be prepared from a compound of the formula (XVIII). It will be appreciated by the skilled man that in the case where Y is —CS— or —C=N(CN)—, the final intermediates will be compounds of the formula (LX) and (LXI), respectively, in which $L^{21}$ represents either of $L^2$ or $L^3$ and $L^{22}$ represents either of $L^5$ or $L^6$.

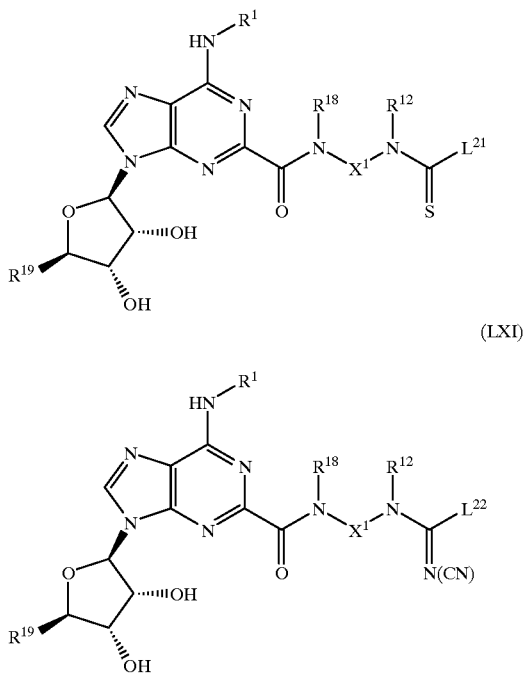

(LX)

(LXI)

Compounds of the formula (LIX) may be prepared by the reaction of a compound of the formula (LI) with a compound of the formula (XXXI), optionally at an elevated temperature, optionally in an inert solvent (e.g. 1,2-dimethoxyethane or 2-methoxyethyl ether) and optionally under pressure. Preferably, the reaction is carried out in the absence of solvent at a temperature of from 100–120° C. The skilled person will appreciate that to achieve the desired regioselectivity, a suitable protecting group (e.g. trifluoroacetyl) may optionally be used for this reaction, located on a chosen N atom of a compound of the formula (XXXI).

14. Compounds of the formula (I) in which $R^2$ is —$CONR^{18}$—$X^1$—$NR^{12}$—CO—$NR^{13}R^{14}$ may be prepared by the reaction of a compound of the formula (LIX) with a compound of the formula (XXXVIII) in which $L^9$ and $L^{10}$ are as defined above to form an intermediate of the formula

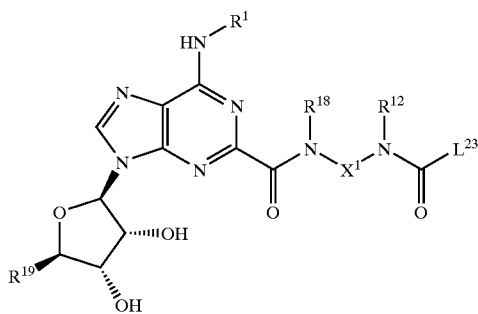

(LXII)

in which $L^{23}$ represents either of the leaving groups $L^9$ or $L^{10}$ and the subsequent reaction of this intermediate with a compound of the formula (XX). In a typical example, where $L^9$ and $L^{10}$ are each imidazol-1-yl, a solution of the compound of the formula (LIX) in a suitable solvent, such as dichloromethane, is treated with 1,1'-carbonyldiimidazole.

The reaction mixture is stirred, preferably at room temperature, until thin layer chromatography (TLC) indicates that a substantially complete reaction has occurred and then a compound of the formula (XX) is added to give the compound of the formula (I).

15. Compounds of the formula (I) in which $R^2$ is —$CONR^{18}$—$X^1$—$NR^{12}$—CS—$NR^{13}R^{14}$ may be prepared by the reaction of a compound of the formula (LIX) with a compound of the formula (XXXX) in which $L^{12}$ is as defined above. The reaction is preferably carried out in a suitable solvent, such as ethanol, and at an elevated temperature, most preferably under reflux.

16. Compounds of the formula (I) in which $R^2$ is —$CONR^{18}$—$X^1$—$NR^{12}$—C=N(CN)—$NR^{13}R^{14}$ may be prepared by the reaction of a compound of the formula (LIX) with a compound of the formula (XXXXI) in which $L^{13}$ is as defined above. The reaction is preferably carried out in a suitable solvent, such as ethanol, and at an elevated temperature, most preferably under reflux.

17. Compounds of the formula (I) in which $R^2$ is —$CONR^{18}$—$X^1$—$NR^{12}$—Y—$NR^{13}R^{14}$ may be prepared by the reaction of a compound of the formula (LIV) in which Z is a suitable leaving group such as bromo, iodo, trialkylstannyl or trifluoromethylsulphonyl, preferably iodo, with a compound of the formula $$R^{18}NH—X^1—NR^{12}—Y—NR^{13}R^{14} \quad \text{(LXIII)}$$

in the presence of carbon monoxide and a suitable catalyst. Preferably the catalyst is a palladium (II) catalyst. More preferably, the catalyst is 1,1'-bis(diphenylphosphino)ferrocenedichloropalladium (II) (optionally as a 1:1 complex with dichloromethane). Alternatively, palladium (II) acetate may be used in the presence of a suitable ligand such as 1,1'-bis(diphenylphosphino)ferrocene, triphenylphosphine, tri(o-tolyl)phosphine or (R)—, (S)— or racemic 2,2'-bis(diphenylphosphino)-1-1'-binaphthyl. In a typical procedure, the reaction is carried out in a sealed vessel in the presence of carbon monoxide at an elevated pressure (e.g. about 345 kPa, 50 psi) at an elevated temperature (e.g. about 60° C.) and in a suitable solvent (e.g. tetrahydrofuran, methanol or ethanol). A suitable organic base such as a tertiary amine (e.g. triethylamine, N-ethyldiisopropylamine or 4-methylmorpholine) may optionally be added.

18. Compounds of the formula (I) in which $R^2$ is —$CONR^{18}$—$X^1$—$NR^{12}$—Y—$NR^{13}R^{14}$ may be prepared by the reaction of a compound of the formula (LI) with a compound of the formula (LXIII), optionally at an elevated temperature, optionally in an inert solvent (e.g. 1,2-dimethoxyethane or 2-methoxyethyl ether) and optionally under pressure. Preferably, the reaction is carried out in the absence of solvent at a temperature of from 100–120° C.

19. Compounds of the formula (IV) in which $R^{19}$ is 1,2,4-oxadiazol-5-yl optionally substituted at the 3 position may be prepared as shown in Scheme 10 in which $P^1$ and $P^2$ are as defined above and $R^{22}$ is H or $C_1$–$C_6$ alkyl, said $C_1$–$C_6$ alkyl being optionally substituted by phenyl, —OH, $C_1$–$C_6$ alkoxy or —$NR^{20}R^{21}$, $R^{20}$ and $R^{21}$ being as defined above.

Scheme 10

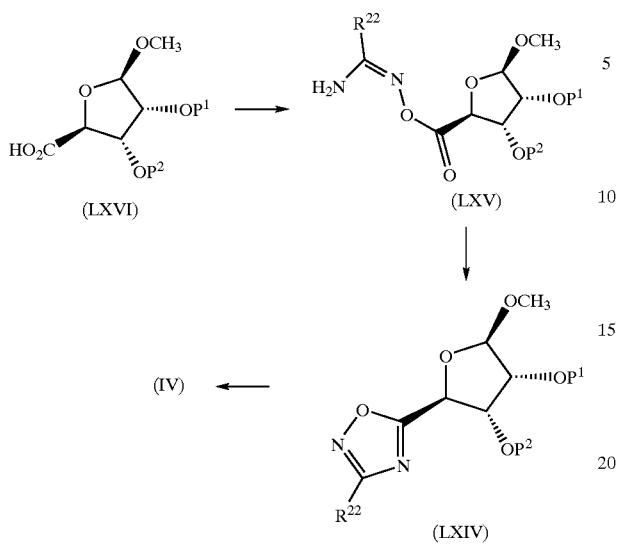

Scheme 11

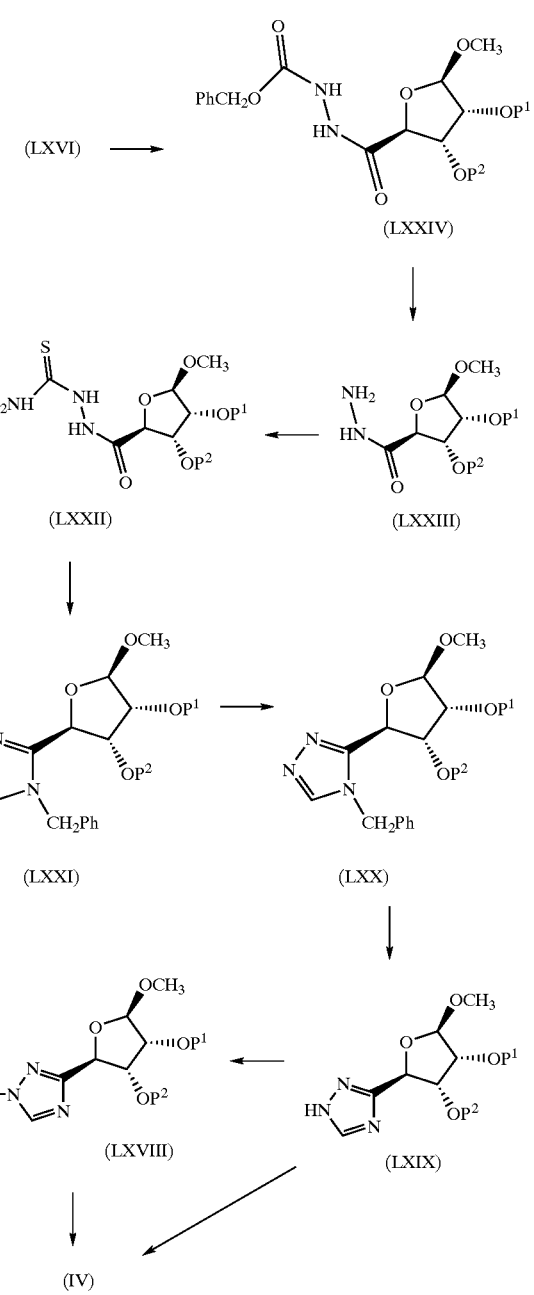

In Scheme 10, compounds of the formula (IV) may be prepared by first treating a compound of the formula (LXIV) with an aqueous solution of an acid such as trifluoroacetic acid or hydrochloric acid, optionally at an elevated temperature, and then treating a solution of the intermediate so obtained, in a suitable solvent (e.g. pyridine), with an acylating agent (e.g. acetic anhydride or acetyl chloride when $W^1$ is methyl or benzoyl chloride when $W^1$ is phenyl). Where the protecting groups $P^1$ and $P^2$ in the compound of the formula (LXIV) are removed under acidic conditions, they will be replaced, as a result of this procedure, by new protecting groups $P^1$ and $P^2$ in the compound of the formula (IV) which are either both acetyl or benzoyl. Compounds of the formula (LXIV) may be prepared by heating a solution of a compound of the formula (LXV) in a suitable solvent (e.g. 2-methoxyethyl ether), preferably to 120° C. Compounds of the formula (LXV) may be prepared from a compound of the formula (LXVI) by activation of the compound of the formula (LXVI) as, for example, an acid chloride and treatment of this activated intermediate with a compound of the formula

In a typical procedure, a compound of formula (LXVI) is dissolved in a suitable inert solvent (e.g. dichloromethane) and treated with oxalyl chloride and, optionally, a catalytic amount of N,N-dimethylformamide. After removal of excess solvent and reagent by evaporation under reduced pressure, the residue is dissolved in a suitable solvent (e.g. ethyl acetate) and treated with the compound of the formula (LXVII). Compounds of the formula (LXVI) are either known or easily prepared by methods well known in the art.

Compounds of the formula (IV) in which $R^{19}$ is 1,2,4-triazol-3-yl optionally substituted at the 1 position may be prepared as shown in Scheme 11 in which $P^1$ and $P^2$ are as defined above and $R^{23}$ is $C_1$–$C_6$ alkyl, said $C_1$–$C_6$ alkyl being optionally substituted by phenyl, —OH, $C_1$–$C_6$ alkoxy or —$NR^{20}R^{21}$, $R^{20}$ and $R^{21}$ being as defined above.

In Scheme 11, compounds of the formula (IV) may be prepared by first treating a compound of the formula (LXVIII) or a compound of the formula (LXIX) with an aqueous solution of an acid such as trifluoroacetic acid or hydrochloric acid, optionally at an elevated temperature, and then treating a solution of the intermediate so obtained, in a suitable solvent (e.g. pyridine), with an acylating agent (e.g. acetic anhydride or acetyl chloride when $W^1$ is methyl or benzoyl chloride when $W^1$ is phenyl). Where the protecting groups $P^1$ and $P^2$ in the compound of the formula (LXVIII) or (LXIX) are removed under acidic conditions, they will be replaced, as a result of this procedure, by new protecting groups $P^1$ and $P^2$ in the compound of the formula (IV) which are either both acetyl or benzoyl. The skilled man will appreciate that in certain cases, this procedure will derivatise the triazole in a compound of the formula (LXIX) with an acetyl or benzoyl group which will be removed in a subsequent deprotection step. Compounds of the formula (LXVIII) may be prepared by treating a solution of a compound of the formula (LXIX) in a suitable solvent (e.g. acetone) with an alkylating agent of the formula $$R^{23}\text{---}L^{24} \qquad (LXXV)$$

in which $L^{24}$ is a suitable leaving group such as bromo or iodo, preferably iodo and $R^{23}$ is as defined above. A base such as potassium carbonate may optionally be added and the reaction is preferably carried out at an elevated temperature, most preferably under reflux. Compounds of the formula (LXIX) may be prepared by the hydrogenation of a compound of the formula (LXX). In a typical procedure, a solution of a compound of the formula (LXX) in a suitable solvent, such as ethyl acetate, ethanol or a mixture thereof, is treated with a suitable catalyst, such as palladium black, and pressurised with hydrogen, preferably to 2758 kPa (400 psi). Compounds of the formula (LXX) may be prepared by treating a solution of a compound of the formula (LXXI) in a suitable solvent, such as acetic acid, with sodium nitrite. Compounds of the formula (LXXI) may be prepared by treating a solution of a compound of the formula (LXXII) in a suitable solvent, such as water, with a base, such as sodium hydroxide, and heating the solution, preferably under reflux. Compounds of the formula (LXXII) may be prepared by treating a solution of a compound of the formula (LXXIII) in a suitable solvent, such as dichloromethane, with benzyl isothiocyanate. Compounds of the formula (LXXIII) may be prepared by the hydrogenation of a compound of the formula (LXXIV). In a typical procedure, a solution of the compound of the formula (LXXIV) in a suitable solvent, such as ethanol, is treated with a suitable catalyst, such as 10% w/w palladium on carbon, and pressurised with hydrogen, preferably to 414 kPa (60 psi). Compounds of the formula (LXXIV) may be prepared from a compound of the formula (LXVI) by activation of the compound of the formula (LXVI) as, for example, an acid chloride and treatment of this activated intermediate with benzyl carbazate. In a typical procedure, the compound of formula (LXVI) is dissolved in a suitable inert solvent (e.g. dichloromethane) and treated with oxalyl chloride and, optionally, a catalytic amount of N,N-dimethylformamide. After removal of excess solvent and reagent by evaporation under reduced pressure, the residue is dissolved in a suitable solvent (e.g. dichloromethane) and treated with benzyl carbazate.

Compounds of the formula (IV) in which $R^{19}$ is 1,2,4-oxadiazol-3-yl optionally substituted at the 5 position, $P^1$ and $P^2$ are each acetyl and $W^1$ is methyl may be prepared as shown in Scheme 12 in which $R^{22}$ is as defined above and $P^1$ and $P^2$, in formulas (LXXVII), (LXXVIII) and (LXXIX) are suitable protecting groups as previously defined.

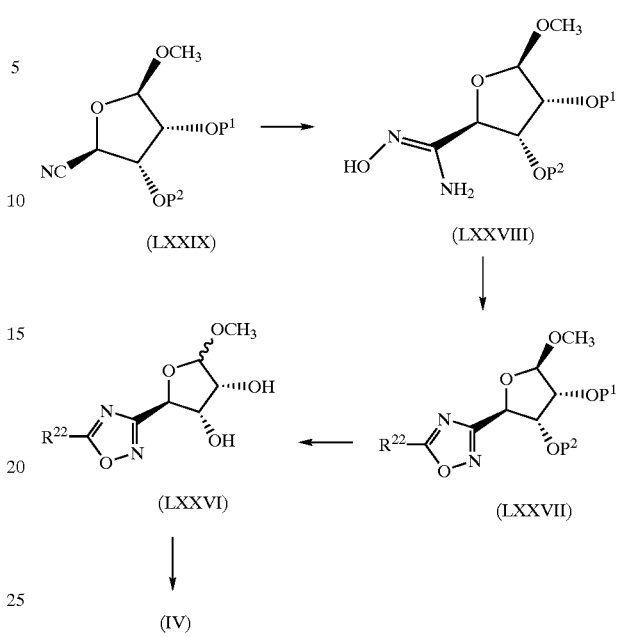

In Scheme 12, compounds of the formula (IV) may be prepared by the reaction of a compound of the formula (LXXVI) with acetic acid, acetic anhydride and concentrated sulphuric acid. The reaction is carried out in a suitable solvent, such as dichloromethane, and at an elevated temperature, preferably under reflux. Compounds of the formula (LXXVI) may be prepared by the deprotection of a compound of the formula (LXXVII). Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$, taken together, represent dimethylmethylene, a solution of the compound of the formula (LXXVII) in aqueous hydrochloric acid is stirred at room temperature. Under such acid conditions, epimerisation of the methoxy substituent may occur. Compounds of the formula (LXXVII) may be prepared by the reaction of a compound of the formula (LXXVIII) with a compound of the formula $$R^{22}CO_2H \qquad (LXXX).$$

In a typical procedure, a solution of the compound of the formula (LXXVIII) and the compound of the formula (LXXX) in a suitable solvent, such as diethylene glycol dimethyl ether, is treated with a suitable acid activating reagent, such as a carbodiimide (preferably 1-(3-dimethylpropyl)-3-ethylcarbodiimide hydrochloride) and heated, preferably at about 110° C. Compounds of the formula (LXXVIII) may be prepared by the reaction of a compound of the formula (LXXIX) with hydroxylamine hydrochloride. The reaction is performed in a suitable solvent, such as methanol, preferably under reflux. Compounds of the formula (LXXIX) are either known (see, for example, WO-A-9967265) or are easily prepared by methods well known in the art.

Compounds of the formula (IV) in which $R^{19}$ is 1,2,3-triazol-4-yl optionally substituted at the 1 position, may be prepared as shown in Scheme 13 in which $P^1$, $P^2$ and $R^{23}$ are as defined above.

Scheme 13

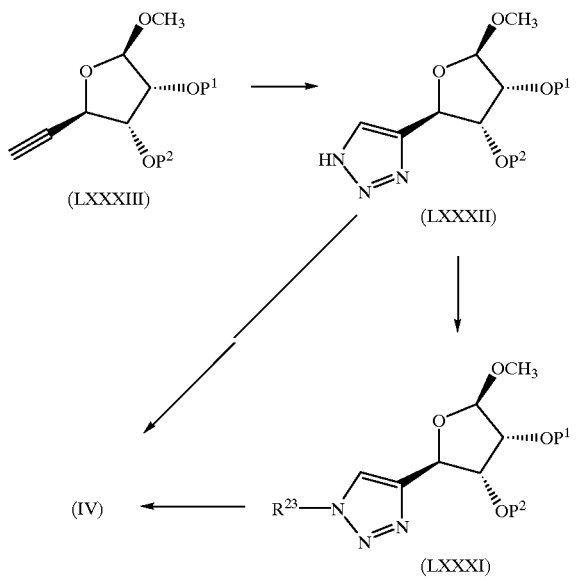

In Scheme 13, compounds of the formula (IV) may be prepared by first treating a compound of the formula (LXXXI) or a compound of the formula (LXXXII) with an aqueous solution of an acid such as trifluoroacetic acid or hydrochloric acid, optionally at an elevated temperature, and then treating a solution of the intermediate so obtained, in a suitable solvent (e.g. pyridine), with an acylating agent (e.g. acetic anhydride or acetyl chloride when $W^1$ is methyl or benzoyl chloride when $W^1$ is phenyl). Where the protecting groups $P^1$ and $P^2$ in the compound of the formula (LXXXI) or the compound of the formula (LXXXII) are removed under acidic conditions, they will be replaced, as a result of this procedure, by new protecting groups $P^1$ and $P^2$ in the compound of the formula (IV) which are either both acetyl or benzoyl. The skilled man will appreciate that in certain cases, this procedure will derivatise the triazole in a compound of the formula (LXXXII) with an acetyl or benzoyl group which will be removed in a subsequent deprotection step. Compounds of the formula (LXXXI) may be prepared by treating a solution of a compound of the formula (LXXXII) in a suitable solvent (e.g. acetone) with an alkylating agent of the formula (LXXV) in which $L^{24}$ and $R^{23}$ are as defined above. A base such as potassium carbonate may optionally be added and the reaction may optionally be carried out at an elevated temperature. Compounds of the formula (LXXXII) may be prepared by the reaction of a compound of the formula (LXXXIII) with trimethylsilylazide. In a typical procedure, a mixture of the compound of the formula (LXXXIII) and trimethylsilylazide are heated together in a teflon lined bomb, preferably at 120° C. Compounds of the formula (LXXXIII) are either known (see, for example, *Helv. Chim. Acta,* 1980, 63, 1181) or are easily prepared by methods well known in the art.

Other compounds of the formula (IV) are either known (see, for example, WO-A-9967265) or are easily prepared by methods well known in the art.

20. Compounds of the formula (I) in which $R^2$ is —X—$NR^{12a}$—Y—$NR^{13}R^{14}$ or —CO—$NR^{18}$—$X^1$—$NR^{12}$—Y—$NR^{13}R^{14}$ and $R^{14}$ is —($C_2$-$C_6$ alkylene)-$NR^8R^a$, wherein $R^a$ is —$CONR^4R^4$, —$COOR^5$, —$COR^5$, —$SO_2R^5$ or —$SO_2NR^4R^4$, may be prepared by the derivatisation of an amine of the formula

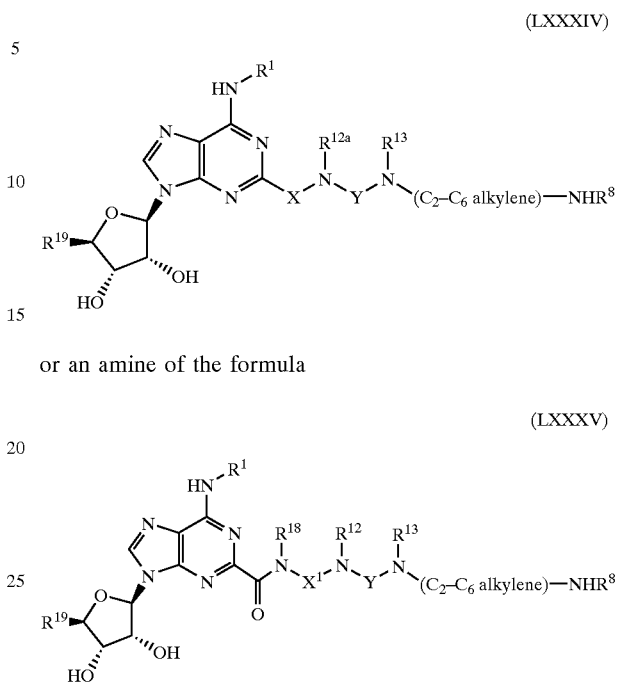

(LXXXIV)

or an amine of the formula (LXXXV)

respectively, with a suitable acylating or sulphonylating agent. For example, compounds of the formula (I) in which $R^2$ is —X—$NR^{12a}$—Y—$NR^{13}R^{14}$ or —CO—$NR^{18}$—$X^1$—$NR^{12}$—Y—$NR^{13}R^{14}$ and $R^{14}$ is —($C_2$-$C_6$ alkylene)-$NR^8COR^5$ may be prepared by the reaction of a compound of the formula (LXXXIV) or (LXXXV), respectively, with an acid chloride of the formula

$R^5COCl$            (LXXXVI).

In a typical procedure, a solution of the compound of the formula (LXXXIV) or (LXXXV) in a suitable solvent, such as a mixture of ethyl acetate and N-methylpyrrolidinone, is treated with a suitable base, preferably a trialkylamine base such as triethylamine, and the compound of the formula (LXXXVI). As a further example, compounds of the formula (I) in which $R^2$ is —X—$NR^{12a}$—Y—$NR^{13}R^{14}$ or —CO—$NR^{18}$—$X^1$—$NR^{12}$—Y—$NR^{13}R^{14}$ and $R^{14}$ is —($C_2$-$C_6$ alkylene)-$NR^8SO_2R^5$ may be prepared by the reaction of a compound of the formula (LXXXIV) or (LXXXV) with a compound of the formula

$R^5SO_2Cl$            (LXXXVII).

In a typical procedure, a solution of the compound of the formula (LXXXIV) or (LXXXV) in a suitable solvent, such as a mixture of ethyl acetate and N-methylpyrrolidinone, is treated with a suitable base, preferably a trialkylamine base such as triethylamine, and the compound of the formula (LXXXVII).

Compounds of the formula (LXXXIV) and (LXXXV) may be prepared by analogy with the methods presented above for the preparation of compounds of the formula (I). Compounds of the formula (LXXXVI) and (LXXXVII) are either commercially available or are easily prepared by methods well known to the skilled man.

Compounds of the formula (I) may also be interconverted using conventional functional group interconversion techniques.

All of the reactions and the preparations of novel starting materials used in the preceding methods are conventional and appropriate reagents and reaction conditions as well as procedures for isolating the desired products will be well-known to persons skilled in the art with reference to literature precedents and the Examples and Preparations sections below.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (I) are demonstrated by their ability to inhibit neutrophil function which indicates A2a receptor agonist activity. This is evaluated by determining the compound profile in an assay where superoxide production is measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. *Adenosine deaminase* was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the formula (I) may also be administered as fast-dispersing or fast-dissolving dosage forms or in the form of a high energy dispersion or as coated particles. Suitable formulations of the compounds of the formula (I) may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, sodium stearyl fumarate, sodium lauryl sulphate, stearic acid, glyceryl behenate and talc may be included.

General Example

A formulation of the tablet could typically contain between about 0.01 mg and 500 mg of active compound whilst tablet fill weights may range from 50 mg to 1000 mg.

An example of a formulation for a 10 mg tablet is illustrated below:

| Ingredient | % w/w |
| --- | --- |
| Compound of the formula (I) or salt | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be administered parenterally, for example, intravenously, intraarterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, a co-solvent and/or enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.00001 to 100 mg/kg, preferably from 0.0001 to 100 mg/kg (in single or divided doses).

Thus tablets or capsules of the compound of the formula (I) may contain from 0.01 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrof luoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol (optionally aqueous ethanol) or a suitable agent for dispersing, solubilising or extending release and the propellant as the solvent, which may additionally contain a lubricant, e.g. sorbitan trioleate. Capsules, blisters and cartridges (made, for example, from gelatin or HPMC) for use in an inhaler or insufflator may be formulated to contain a powder mix of a compound of the formula (I), a suitable powder base such as lactose or starch and a performance modifier such as L-leucine, manitol or magnesium stearate.

A suitable solution formulation for use in an atomiser using electrohydrodynamics to produce a fine mist may contain from 1 µg to 10 mg of a compound of the formula (I), or a salt thereof, and the actuation volume may vary from 1 to 100 µl. A typical formulation may comprise a compound of the formula (I) or salt thereof, propylene glycol, sterile water, ethanol and sodium chloride.

Aerosol or dry powder formulations are preferably arranged so that each metered dose or "puff" contains from 1 to 4000 µg of a compound of the formula (I) for delivery to the patient. The overall daily dose with an aerosol will be in the range of from 1 µg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be dermally or transdermally administered, for example, by the use of a skin patch. They may also be administered by the pulmonary, vaginal or rectal routes.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment.

Thus the invention provides:

(i) a compound of the formula (I) or a pharmaceutically acceptable salt or solvate thereof;

(ii) a process for the preparation of a compound of the formula (I) or a pharmaceutically acceptable salt or solvate thereof;

(iii) a pharmaceutical composition including a compound of the formula (I) or a pharmaceutically acceptable salt or solvate thereof, together with a pharmaceutically acceptable excipient, diluent or carrier;

(iv) a compound of the formula (I) or a pharmaceutically acceptable salt, solvate or composition thereof, for use as a medicament;

(v) a compound of the formula (I) or a pharmaceutically acceptable salt, solvate or composition thereof, for use as an A2a receptor agonist;

(vi) a compound of the formula (I) or a pharmaceutically acceptable salt, solvate or composition thereof, for use as an anti-inflammatory agent;

(vii) a compound of the formula (I) or a pharmaceutically acceptable salt, solvate or composition thereof, for use in the treatment of a respiratory disease;

(viii) a compound as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(ix) a compound of the formula (I) or a pharmaceutically acceptable salt, solvate or composition thereof, for use in the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing;

(x) the use of a compound of the formula (I) or of a pharmaceutically acceptable salt, solvate or composition thereof, for the manufacture of a medicament having A2a receptor agonist activity;

(xi) the use of a compound of the formula (I) or of a pharmaceutically acceptable salt, solvate or composition thereof, for the manufacture of an anti-inflammatory agent;

(xii) the use of a compound of the formula (I) or of a pharmaceutically acceptable salt, solvate or composition thereof, for the manufacture of a medicament for the treatment of a respiratory disease;

(xiii) use as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(xiv) the use of a compound of the formula (I) or of a pharmaceutically acceptable salt, solvate or composition thereof, for the manufacture of a medicament for the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastro-intestinal tract or a psychotic disorder, or for wound healing;

(xv) a method of treatment of a mammal, including a human being, with a A2a receptor agonist including treating said mammal with an effective amount of a compound of the formula (I) or with a pharmaceutically acceptable salt, solvate or composition thereof;

(xvi) a method of treatment of a mammal, including a human being, to treat an inflammatory disease including treating said mammal with an effective amount of a compound of the formula (I) or with a pharmaceutically acceptable salt, solvate or composition thereof;

(xvii) a method of treatment of a mammal, including a human being, to treat a respiratory disease including treating said mammal with an effective amount of a compound of the formula (I) or with a pharmaceutically acceptable salt, solvate or composition thereof;

(xviii) a method as in (xvii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(xix) a method of treatment of a mammal, including a human being, to treat septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastro-intestinal tract or a psychotic disorder, or for wound healing, including treating said mammal with an effective amount of a compound of the formula (I) or with a pharmaceutically acceptable salt, solvate or composition thereof; and (xx) certain novel intermediates disclosed herein.

The following Examples illustrate the preparation of the compounds of the formula (I):

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; DMSO, dimethylsulphoxide. The abbreviation psi means pounds per square inch and LRMS means low resolution mass spectrometry. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

EXAMPLE 1

N-({6-[(2,2-Diphenylethyl)amino]-9-[(2R,3R,4S,5R)-5-(2-ethyl-2H-tetrazol-5-yl)-3,4-dihydroxytetrahydro-2-furanyl]-9H-purin-2-yl}methyl)-2-methyl-1-propanesulphonamide

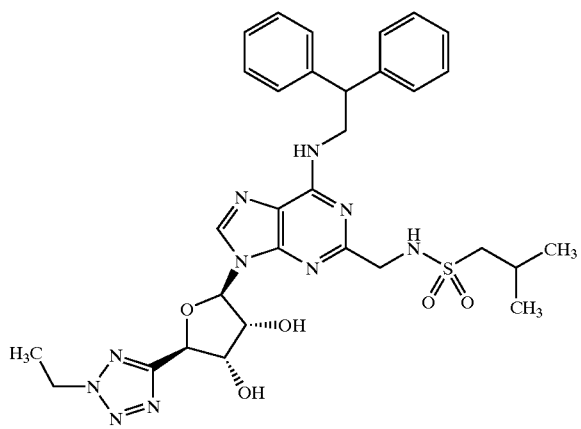

A solution of (2R,3R,4R,5R)-4-(acetyloxy)-2-(6-[(2,2-diphenylethyl)amino]-2-{[(isobutylsulphonyl)amino]methyl}-9H-purin-9-yl)-5-(2-ethyl-2H-tetrazol-5-yl)tetrahydro-3-furanyl acetate (Preparation 26) (230 mg, 0.31 mmol) and sodium carbonate (130 mg, 1.23 mmol) in methanol (15 ml) and water (1.5 ml) was stirred at room temperature overnight. The solvent was evaporated under reduced pressure and the residue was partioned between ethyl acetate (50 ml) and water (10 ml). The organic layer was washed with brine (10 ml), dried (anhydrous sodium sulphate) and evaporated under reduced pressure. The residue was purified by column chromatography on silica gel eluting with dichloromethane:methanol (97:3 by volume). Product containing fractions were evaporated to afford the title compound as a white powder (190 mg).

$^1$H-NMR (400 MHz, CDCl$_3$) δ: 7.85 (1H, s), 7.35–7.20 (10H, m), 6.35 (1H, m), 6.05 (1H, d), 5.80 (1H, br s), 5.65 (1H, m); 5.45 (1H, d), 4.80 (1H, s), 4.70–4.60 (3H, m), 4.60–4.20 (5H, m), 3.60 (1H, d), 3.00 (2H, d), 2.30 (1H, m), 1.60 (3H, t), 1.05 (6H, d).

LRMS (thermospray): m/z [MH$^+$] 663.

EXAMPLE 2

6-[(2,2-Diphenylethyl)amino]-9-[(2R,3R,4S,5R)-5-(2-ethyl-2H-tetrazol-5-yl)-3,4-dihydroxytetrahydro-2-furanyl]-N-[2-(1-piperidinyl)ethyl]-9H-purine-2-carboxamide

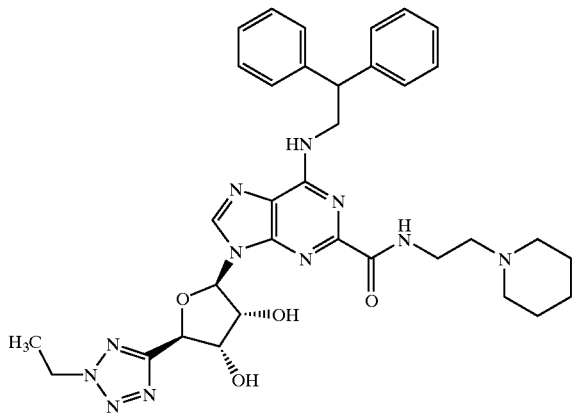

A solution of (2R,3R,4R,5R)-4-(acetyloxy)-2-[6-[(2,2-diphenylethyl)amino]-2-({[2-(1-piperidinyl)ethyl]amino}carbonyl)-9H-purin-9-yl]-5-(2-ethyl-2H-tetrazol-5-yl)tetrahydro-3-furanyl acetate (Preparation 27) (230 mg, 0.31 mmol) and sodium carbonate (130 mg, 1.23 mmol) in methanol (15 ml) and water (1.5 ml) was stirred at room temperature overnight. The solvent was evaporated under reduced pressure and the residue was partioned between ethyl acetate (50 ml) and water (10 ml). The organic layer was washed with brine (10 ml), dried (anhydrous sodium sulphate) and evaporated under reduced pressure. The residue was purified by column chromatography on silica gel eluting with a gradient system of dichloromethane:methanol:0.88 concentrated aqueous ammonia (95:5:0.5 by volume) gradually changing to dichloromethane:methanol:0.88 concentrated aqueous ammonia (93:7:0.7 by volume). Product containing fractions were evaporated and the resulting solid triturated with ether, filtered and dried to afford the title compound as a white powder (158 mg).

$^1$H-NMR (400 MHz, CDCl$_3$) δ: 8.50 (1H, s), 8.40 (1H, br s), 7.35–7.20 (10H, m), 6.85 (1H, d), 6.20 (1H, br s), 5.90 (1H, br s), 5.80 (2H, m); 4.90 (1H, m), 4.75–4.65 (3H, m), 4.40–4.25 (3H, m), 3.50 (2H, m), 2.50 (2H, m), 2.35 (4H, m), 1.65 (3H, t), 1.45–1.25 (6H, m).

LRMS (thermospray): m/z [MH$^+$] 669.

EXAMPLE 3

6-[(2,2-Diphenylethyl)amino]-9-[(2R,3R,4S,5R)-5-(2-ethyl-2H-tetrazol-5-yl)-3,4-dihydroxytetrahydro-2-furanyl]-N-(2-phenylethyl)-9H-purine-2-carboxamide

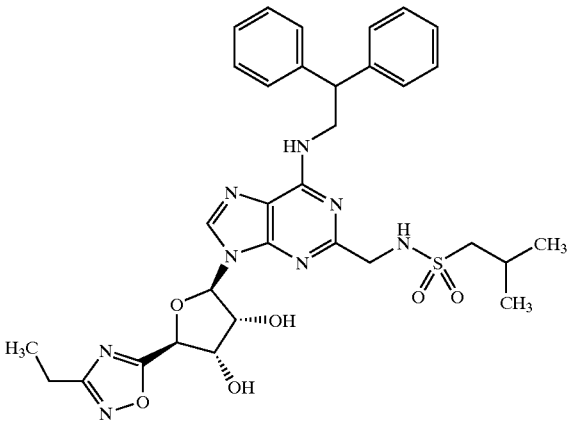

A mixture of methyl 9-[(2R,3R,4R,5R)-3,4-bis(acetyloxy)-5-(2-ethyl-2H-tetrazol-5-yl)tetrahydro-2-furanyl]-6-[(2,2-diphenylethyl)amino]-9H-purine-2-carboxylate (Preparation 30) (100 mg, 0.15 mmol) and 2-phenylethylamine (0.2 ml, 1.58 mmol) were heated together under a nitrogen atmosphere at 130° C. for three hours. The mixture was allowed to cool to room temperature and was then purified by column chromatography on silica gel eluting with a gradient system of ethyl acetate gradually changing to ethyl acetate:methanol (95:5 by volume). Product containing fractions were evaporated and the resulting solid was triturated with ether, filtered and dried to afford the title compound as a white powder (50 mg).

$^1$H-NMR (400 MHz, CDCl$_3$) δ: 8.50 (1H, s), 7.95 (1H, s), 7.35–7.05 (15H, m), 6.90 (1H, d), 6.25 (1H, br s), 5.95 (1H, d), 5.80 (2H, s), 4.95 (1H, m), 4.75–4.60 (3H, m), 4.30 (1H, m), 4.15 (2H, m), 3.65 (2H, m), 2.85 (2H, t), 1.65 (3H, t).

LRMS (thermospray): m/z [MH$^+$] 661; [MNa$^+$] 683.

EXAMPLE 4

N-({6-[(2,2-Diphenylethyl)amino]-9-[(2R,3R,4S,5S)-5-(3-ethyl-1,2,4-oxadiazol-5-yl)-3,4-dihydroxytetrahydro-2-furanyl]-9H-purin-2-yl}methyl)-2-methyl-1-propanesulphonamide Prepared from (2R,3R,4S,5S)-4-(acetyloxy)-2-(6-[(2,2-diphenylethyl)amino]-2-{[(isobutylsulphonyl)amino]methyl}-9H-purin-9-yl)-5-(3-ethyl-1,2,4-oxadiazol-5-yl)tetrahydro-3-furanyl acetate (Preparation 31) by the same method as Example 1. The title compound was obtained as a white powder.

¹H-NMR (400 MHz, CDCl₃) δ: 7.90 (1H, s), 7.35–7.20 (10H, m), 6.10 (1H, m), 6.00–5.85 (2H, m), 5.50 (1H, br s), 5.30 (1H, m), 4.80 (1H, br s), 4.75 (1H, m), 4.50–4.20 (5H, m), 3.80 (1H, s), 3.00 (2H, d), 2.80 (2H, q), 2.30 (1H, m), 1.30 (3H, t), 1.10 (6H, d).

LRMS (thermospray): m/z [MH⁺] 663.

EXAMPLE 5

6-[(2,2-Diphenylethyl)amino]-9-[(2R,3R,4S,5S)-5-(3-ethyl-5-isoxazolyl)-3,4-dihydroxytetrahydro-2-furanyl]-N-[2-(1-piperidinyl)ethyl]-9H-purine-2-carboxamide

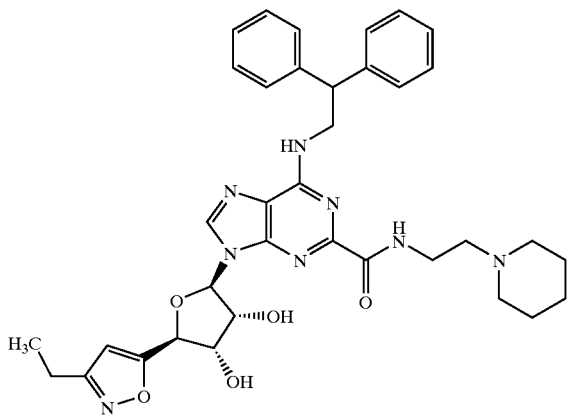

Prepared from (2R,3R,4R,5S)-4-(acetyloxy)-2-[6-[(2,2-diphenylethyl)amino]-2-({[2-(1-piperidinyl)ethyl]amino}carbonyl)-9H-purin-9-yl]-5-(3-ethyl-5-isoxazolyl)tetrahydro-3-furanyl acetate (Preparation 32) by the same method as Example 2. The title compound was obtained as a white powder.

¹H-NMR (400 MHz, CDCl₃) δ: 8.50 (1H, m), 8.20 (1H, s), 7.35–7.20 (10H, m), 6.70 (1H, d), 6.25 (1H, br s), 6.10–5.95 (2H, m), 5.50 (1H, s); 4.70–4.60 (2H, m), 4.40–4.25 (3H, m), 3.50 (2H, m), 2.70 (2H, q), 2.55 (2H, m), 2.40 (4H, m), 1.45–1.25 (9H, m).

LRMS (thermospray): m/z [MH⁺] 667.

EXAMPLE 6

N-({6-[(2,2-Diphenylethyl)amino]-9-[(2R,3R,4S,5R)-5-(1-ethyl-1H-1,2,4-triazol-3-yl)-3,4-dihydroxytetrahydro-2-furanyl]-9H-purin-2-yl}methyl)-2-methyl-1-propanesulphonamide

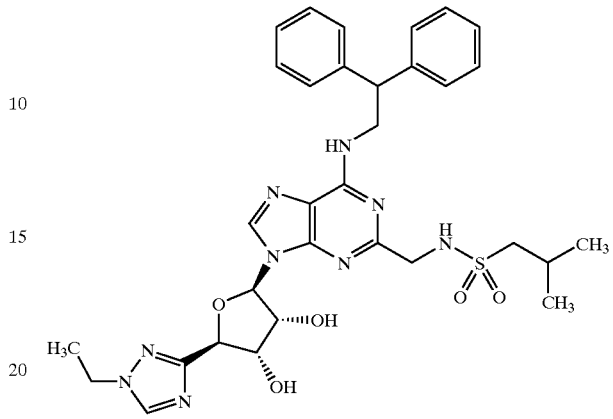

Prepared from (2R,3R,4R,5R)-4-(benzoyloxy)-2-(6-[(2,2-diphenylethyl)amino]-2-{[(isobutylsulphonyl)amino]methyl}-9H-purin-9-yl)-5-(1-ethyl-1H-1,2,4-triazol-3-yl)tetrahydro-3-furanyl benzoate (Preparation 33) by the same method as Example 1. The title compound was obtained as a white powder.

¹H-NMR (400 MHz, CDCl₃) δ: 8.10 (1H, s), 7.95 (1H, s), 7.35–7.20 (10H, m), 6.50 (1H, m), 6.10 (1H, d), 5.85 (1H, br s), 5.35 (1H, m), 5.25 (1H, m), 4.80 (1H, m), 4.50–4.10 (8H, m), 3.55 (1H, m), 2.95 (2H, d), 2.25 (1H, m), 1.50 (3H, t), 1.05 (6H, d).

LRMS (thermospray): m/z [MH⁺] 662.

EXAMPLE 7

6-[(2,2-Diphenylethyl)amino]-9-[(2R,3R,4S,5R)-5-(1-ethyl-1H-1,2,4-triazol-3-yl)-3,4-dihydroxytetrahydro-2-furanyl]-N-[2-(1-piperidnyl)ethyl]-9H-purine-2-carboxamide

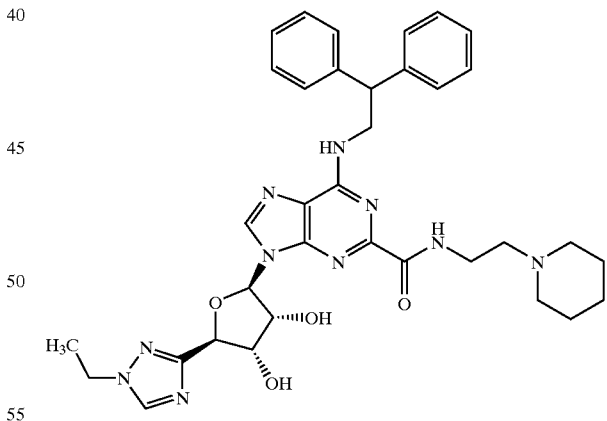

Prepared from (2R,3R,4R,5R)-4-(benzoyloxy)-5-[6-[(2,2-diphenylethyl)amino]-2-({[2-(1-piperidinyl)ethyl]amino}carbonyl)-9H-purin-9-yl]-2-(1-ethyl-1H-1,2,4-triazol-3-yl)tetrahydro-3-furanyl benzoate (Preparation 34) by the same method as Example 2. The title compound was obtained as a white powder.

¹H-NMR (400 MHz, CD₃OD) δ: 8.65 (1H, s), 8.45 (1H, s), 7.35 (4H, m), 7.25 (4H, m), 7.15 (2H, m), 6.30 (1H, d), 5.15 (1H, d); 4.70 (1H, m), 4.65–4.30 (4H, m), 4.25 (2H, q), 3.60 (2H, m), 2.75–2.55 (6H, m), 1.60 (4H, m), 1.50 (5H, m).

LRMS (thermospray): m/z [M⁺] 667.

EXAMPLE 8

N-({6-[(2,2-Diphenylethyl)amino]-9-[(2R,3R,4S,5R)-5-(5-ethyl-1,2,4-oxadiazol-3-yl)-3,4-dihydroxytetrahydro-2-furanyl]-9H-purin-2-yl}methyl)-2-methyl-1-propanesulphonamide

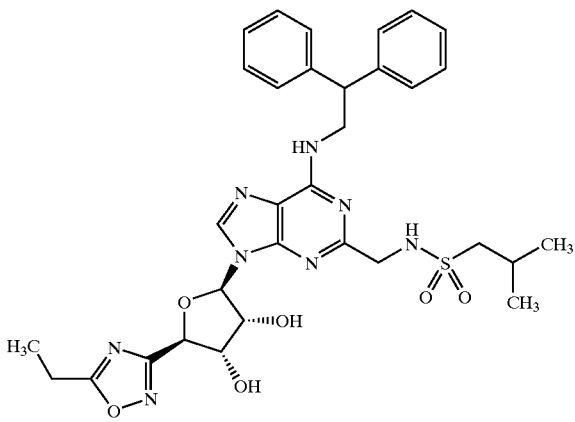

Prepared from (2R,3R,4R,5R)-4-(acetyloxy)-2-(6-[(2,2-diphenylethyl)amino]-2-{[(isobutylsulphonyl)amino]methyl}-9H-purin-9-yl)-5-(5-ethyl-1,2,4-oxadiazol-3-yl)tetrahydro-3-furanyl acetate (Preparation 39) by the same method as Example 1. The title compound was obtained as a white powder.

$^1$H-NMR (400 MHz, CDCl$_3$) δ: 7.95 (1H, s), 7.35–7.20 (10H, m), 6.10 (1H, d), 5.85 (1H, m), 5.80 (1H, br s), 5.40–5.30 (2H, m), 4.80 (1H, m), 4.65 (1H, br s), 4.50–4.20 (5H, m), 3.30 (1H, d), 2.95 (2H, d), 2.90 (2H, q), 2.30 (1H, m), 1.40 (3H, t), 1.10 (6H, d).

LRMS (thermospray): m/z [MH$^+$] 664.

EXAMPLE 9

N-({6-[(2,2-Diphenylethyl)amino]-9-[(2R,3R,4S,5R)-5-(1-ethyl-1H-1,2,3-triazol-4-yl)-3,4-dihydroxytetrahydro-2-furanyl]-9H-purin-2-yl}methyl)-2-methyl-1-propanesulphonamide

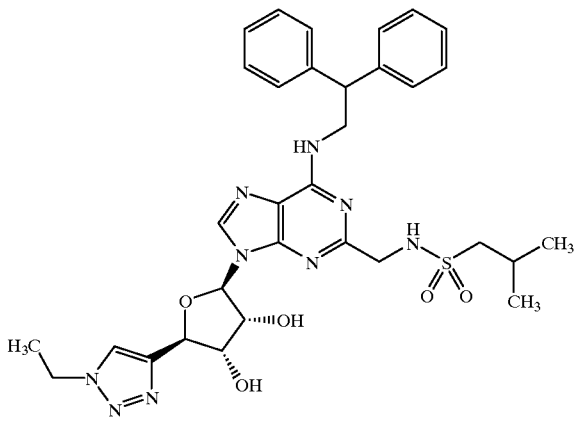

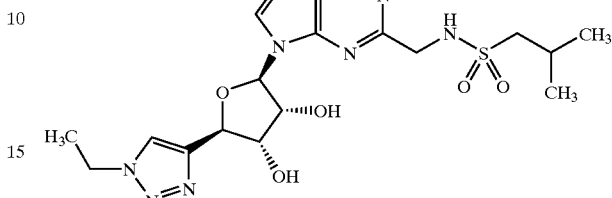

Prepared from (2R,3R,4R,5R)-4-(benzoyloxy)-5-(6-[(2,2-diphenylethyl)amino]-2-{[(isobutylsulphonyl)amino]methyl}-9H-purin-9-yl)-2-(1-ethyl-1H-1,2,3-triazol-4-yl)tetrahydro-3-furanyl benzoate (Preparation 40) by the same method as Example 1. The title compound was obtained as a white powder.

$^1$H-NMR (400 MHz, CDCl$_3$) δ: 7.85 (1H, s), 7.60 (1H, s), 7.35–7.20 (10H, m), 6.75 (1H, m), 6.00 (1H, d), 5.90–5.70 (2H, m), 5.20 (1H, m), 4.80 (1H, m), 4.55–4.20 (8H, m), 3.90 (1H, br s), 3.00 (2H, m), 2.30 (1H, m), 1.50 (3H, t), 1.05 (6H, d).

LRMS (thermospray): m/z [MH$^+$] 662.

EXAMPLE 10

N-{2-[Cyclopentyl(isopropyl)amino]ethyl}-N'-({6-[(2,2-diphenylethyl)amino]-9-[(2R,3R,4S,5R)-5-(2-ethyl-2H-tetrazol-5-yl)-3,4-dihydroxytetrahydro-2-furanyl]-9H-purin-2-yl}methyl)urea

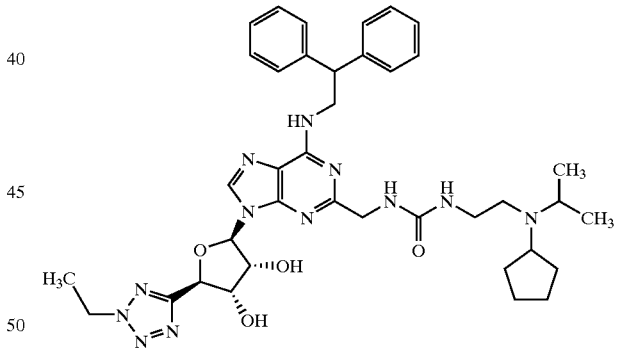

A solution of (2R,3R,4R,5R)-4-(acetoxy)-2-{2-({[({2-[cyclopentyl(isopropyl)amino]ethyl}amino)carbonyl]amino}methyl)-6-[(2,2-diphenylethyl)amino]-9H-purin-9-yl}-5-(2-ethyl-2H-tetrazol-5-yl)tetrahydro-3-furanyl acetate (Preparation 45) (135 mg, 0.16 mmol) and sodium carbonate (5 mg, 0.05 mmol) in methanol (5 ml) was stirred at room temperature overnight. The solvent was evaporated under reduced pressure and the residue was purified by column chromatography on silica gel eluting with a gradient system of dichloromethane:methanol:conc. aqueous ammonia (95:5:0.5 by volume) gradually changing to dichloromethane:methanol:conc. aqueous ammonia (90:10:1 by volume). Product containing fractions were evaporated and the resulting solid was dried under vacuum to afford the title compound as a white powder (35 mg).

¹H-NMR (400 MHz, CD₃OD) δ: 8.35 (1H, s), 7.35–7.25 (8H, m), 7.20–7.10 (2H, m), 6.25 (1H, d), 5.35 (1H, d), 4.75–4.65 (3H, m), 4.50–4.35 (4H, m), 4.30–4.20 (2H, m), 3.30 (2H, s), 3.25–3.10 (4H, m), 2.70 (2H, m), 1.90–1.80 (3H, m), 1.70–1.40 (9H, m), 1.10 (6H, d).

LRMS (thermospray): m/z [MH⁺] 740.

EXAMPLE 11

N-({6-[(2,2-Diphenylethyl)amino]-9-[(2R,3R,4S,5R)-5-(2-ethyl-2H-tetrazol-5-yl)-3,4-dihydroxytetrahydro-2-furanyl]-9H-purin-2-yl}methyl)-N'-[2-(1-piperidinyl)ethyl]urea

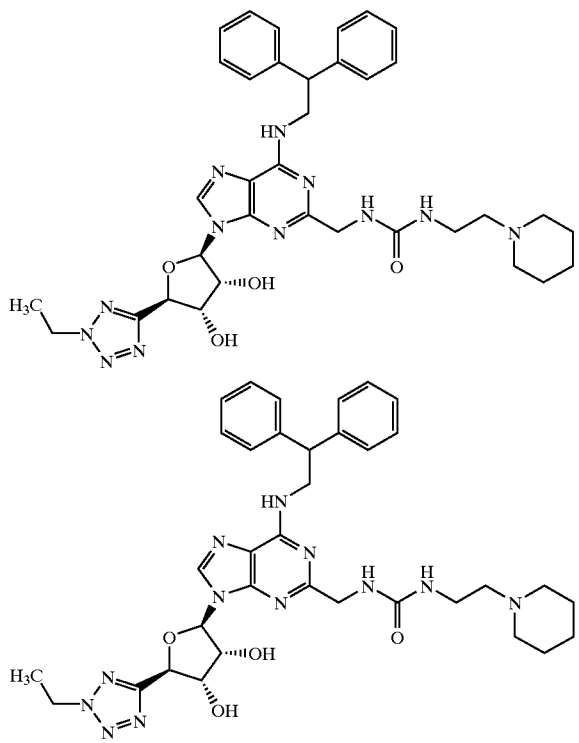

The title compound was prepared from (2R,3R,4R,5R)-4-(acetoxy)-2-(6-[(2,2-diphenylethyl)amino]-2-{[({[2-(1-piperidinyl)ethyl]amino}carbonyl)amino]methyl}-9H-purin-9-yl)-5-(2-ethyl-2H-tetrazol-5-yl)tetrahydro-3-furanyl acetate (Preparation 46) by a similar method to Example 10. The title compound was obtained as a white powder.

¹H-NMR (400 MHz, CD₃OD) δ: 8.35 (1H, s), 7.35–7.25 (8H, m), 7.20–7.15 (2H, m), 6.25 (1H, d), 5.35 (1H, d), 4.85 (1H, m), 4.75–4.65 (3H, m), 4.50–4.35 (4H, m), 4.30–4.20 (2H, m), 2.50–2.40 (6H, m), 1.65–1.55 (7H, m), 1.45–1.40 (2H, m).

LRMS (thermospray): m/z [MH⁺] 698.

The following Preparations describe the preparation of certain intermediates used in the preceding Examples.

Preparation 1

2,6-Dichloro-9-tetrahydro-2H-pyran-2-yl-9H-purine

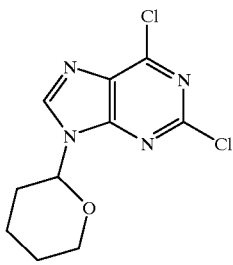

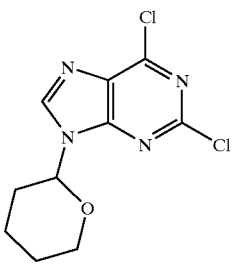

2,6-Dichloro-9H-purine (20 g, 0.11 mol) and 4-toluenesulphonic acid monohydrate (0.2 g) were dissolved in ethyl acetate (300 ml), the mixture was heated to 50° C. and a solution of 2,3-dihydropyran (12.6 ml, 0.14 mol) in ethyl acetate (50 ml) was added slowly over 30 minutes. The reaction mixture was then cooled to room temperature, water (100 ml) was added and the pH of the solution was adjusted to 7 with a saturated aqueous solution of sodium hydrogen carbonate. The layers were separated and the organic layer was washed sequentially with water and brine, dried (anhydrous magnesium sulphate), filtered and evaporated under reduced pressure. The residue was twice azeotroped from pentane to afford the title compound as a slightly impure white solid (30.9 g).

¹H-NMR (CDCl₃) δ: 8.30 (1H, s), 5.75 (1H, dd), 4.25–4.15 (1H, m), 3.85–3.70 (1H, m), 2.20–1.60 (6H, m).

Preparation 2

2-Chloro-N-(2,2-diphenylethyl)-9-tetrahydro-2H-pyran-2-yl-9H-purin-6-amine

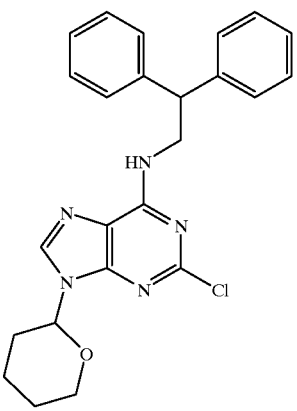

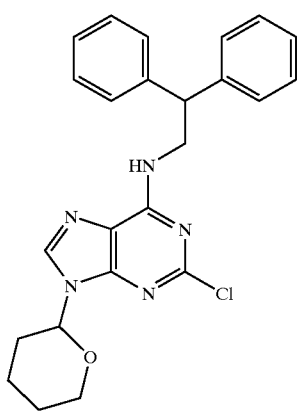

A solution of 2,6-dichloro-9-tetrahydro-2H-pyran-2-yl-9H-purine (Preparation 1) (30.9 g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture was heated under reflux for 3 hours. The solvent was removed under reduced pressure and the residue was azeotroped from ethyl acetate. The residue was purified by column chromatography on silica gel eluting with a gradient system of ethyl acetate:hexane (40:60 by volume) gradually changing to ethyl acetate:hexane (60:40 by volume) to afford the title compound as a foam (49.7 g).

$^1$H-NMR (CDCl$_3$) δ: 7.95–7.75 (1H, br s), 7.35–7.15 (10H, m), 5.80–5.70 (1H, br s), 5.65 (1H, d), 4.35 (1H, m), 4.30–4.18 (1 H, br s), 4.10 (1H, d), 3.70 (1H, t), 2.05–1.95 (2H, m), 1.95–1.80 (1H, m), 1.80–1.55 (3H, m).

Preparation 3

N-(2,2-Diphenylethyl)-2-(methylsulphanyl)-9-tetrahydro-2H-pyran-2-yl-9H-purin-6-amine

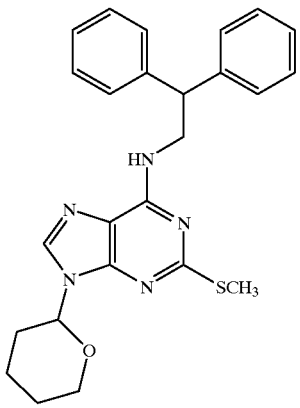

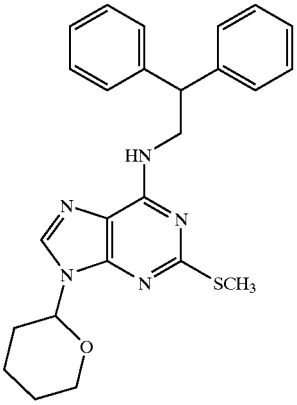

A solution of 2-chloro-N-(2,2-diphenylethyl)-9-tetrahydro-2H-pyran-2-yl-9H-purin-6-amine (Preparation 2) (49.7 g, 0.11 mol) in dry N,N-dimethylformamide (200 ml) was treated with sodium thiomethoxide (10 g, 0.14 mol) and the resulting mixture was heated under an atmosphere of nitrogen at 100° C. for 90 minutes. The mixture was stirred at room temperature for 72 hours and then reheated to 100° C. for a further 2 hours. The reaction mixture was cooled and diluted with water (1000 ml). A suspension was formed which was extracted with two portions of diethyl ether (1000 ml). The combined organic layers were washed sequentially with water and brine, dried (anhydrous magnesium sulphate), filtered and evaporated under reduced pressure. The residue was azeotroped from diethyl ether and then pentane to afford the title compound as a foam (48.9 g).

$^1$H-NMR (CDCl$_3$) δ: 7.80 (1H, s), 7.20–7.10 (10H, m), 5.70–5.55 (2H, d), 4.40–4.20 (3H, m), 4.20–4.05 (1H, m), 3.80–3.65 (1H, m), 2.60 (3H, s), 2.15–1.90 (3H, m), 1.90–1.60 (3H, m).

Preparation 4

N-(2,2-Diphenylethyl)-2-(methylsulphonyl)-9-tetrahydro-2H-pyran-2-yl-9H-purin-6-amine

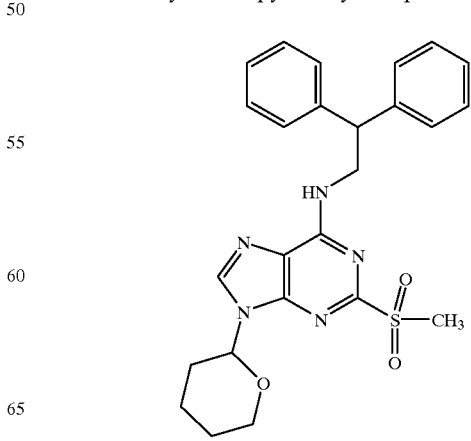

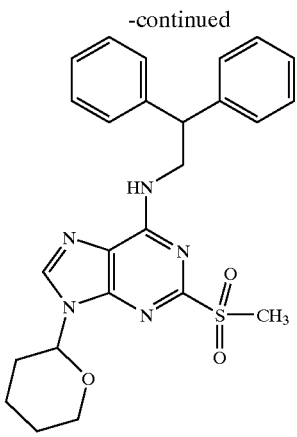

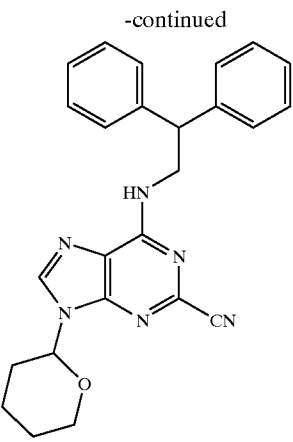

A solution of Oxone (trade mark) (potassium peroxymonosulphate) (44 g, 71.7 mmol) in water (200 ml) was added dropwise over 2 hours to a solution of N-(2,2-diphenylethyl)-2-(methylsulphanyl)-9-tetrahydro-2H-pyran-2-yl-9H-purin-6-amine (Preparation 3) (25 g, 56.2 mmol) and sodium hydrogen carbonate (20 g, 238 mmol) in acetone (1000 ml) and water (250 ml). The resulting mixture was stirred at room temperature for 24 hours and filtered and the residue was washed with acetone. The acetone was removed from the filtrate under reduced pressure and the resulting aqueous residue was extracted with ethyl acetate (1000 ml) and then dichloromethane (1000 ml). The combined organic layers were washed with brine, dried (anhydrous magnesium sulphate), filtered and evaporated under reduced pressure. The residue was triturated with diethyl ether, filtered, washed with diethyl ether and pentane and then dried to afford the title compound as a white solid (20.32 g).

$^1$H-NMR (CDCl$_3$) δ: 8.00 (1H, s), 7.35–7.15 (10H, m), 6.05–5.95 (1H, br s), 5.75 (1H, d), 4.40–4.35 (1H, m), 4.35–4.20 (2H, br s), 4.15–4.05 (1H, m), 3.75 (1H, t), 3.30 (3H, s), 2.18–2.05 (1H, m), 2.05–1.98 (1H, m), 1.98–1.80 (1H, m), 1.80–1.60 (3H, m).

Preparation 5

6-[(2,2-Diphenylethyl)amino]-9-tetrahydro-2H-pyran-2-yl-9H-purine-2-carbonitrile

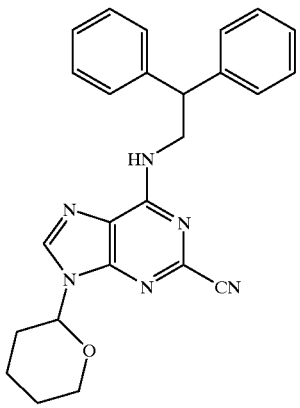

A solution of N-(2,2-diphenylethyl)-2-(methylsulphonyl)-9-tetrahydro-2H-pyran-2-yl-9H-purin-6-amine (Preparation 4) (20.1 g, 42.1 mmol) in dry N,N-dimethylformamide (100 ml) was treated with potassium cyanide (5.5 g, 84.6 mmol) and the mixture was heated at 120° C. for 24 hours under a nitrogen atmosphere. The mixture was then cooled to room temperature, poured into water (1000 ml) and stirred for a further 1 hour. The resultant solid was slowly filtered and washed several times with water. The solid was then dissolved in dichloromethane and the resulting solution was washed with water, dried (anhydrous magnesium sulphate), filtered and evaporated under reduced pressure. The residue was azeotroped from diethyl ether twice to afford the title compound as an oil (17 g). $^1$H-NMR (CDCl$_3$) δ: 8.00 (1H, s), 7.40–7.20 (10H, m), 6.00–5.75 (1H, br s), 5.70 (1H, d), 4.40–4.20 (3H, m), 4.20–4.10 (1H, m), 3.80–3.70 (1H, m), 2.20–1.90 (3H, m), 1.90–1.60 (3H, m).

Preparation 6

2-(Aminomethyl)-N-(2,2-diphenylethyl)-9-tetrahydro-2H-pyran-2-yl-9H-purin-6-amine (1.0 g, 2.33 mmol)

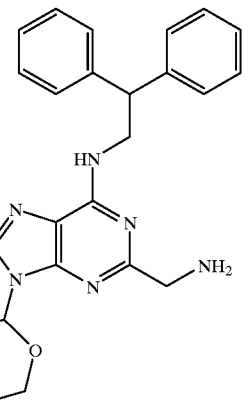

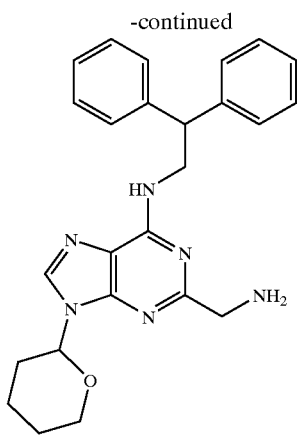

A solution of 6-[(2,2-diphenylethyl)amino]-9-tetrahydro-2H-pyran-2-yl-9H-purine-2-carbonitrile (5.70 g, 13.18 mmol) (Preparation 5) in ethanol (200 ml) saturated with ammonia gas was treated with Pearlman's catalyst (1.00 g), pressurised to 414 kPa (60 psi) with hydrogen in a sealed vessel and stirred at room temperature for 30 hours. The suspension was filtered through a pad of Arbocel (trade mark) and the solvent was removed under reduced pressure. The residue was twice azeotroped from dichloromethane and then purified by column chromatography on silica gel eluting with dichloromethane:methanol (95:5 by volume) gradually changing to dichloromethane:methanol:0.88 ammonia (90:10:0.5 by volume) to afford the title compound (4.34 g).

$^1$H-NMR (CDCl$_3$) δ: 7.84 (1H, s), 7.14–7.36 (10H, m), 5.70 (1H, d), 5.50–5.70 (1H, br s), 4.20–4.42 (3H, m), 4.14 (1H, d), 3.95 (2H, s), 3.78 (1H, t), 1.90–2.20 (5H, m), 1.50–1.88 (3H, m).

LRMS (thermospray): m/z [MH$^+$] 429.

Preparation 7

N-({6-[(2,2-Diphenylethyl)amino]-9-tetrahydro-2H-pyran-2-yl-9H-purin-2-yl}methyl)-2-methyl-1-propanesulphonamide

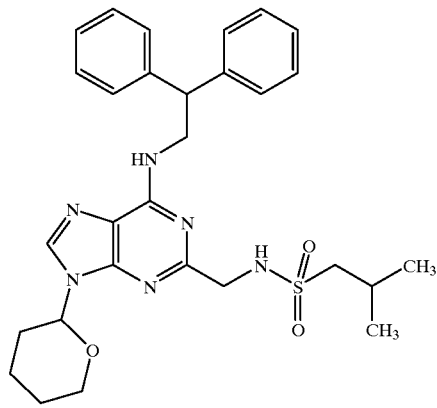

A solution of N-[2-(aminomethyl)-9-tetrahydro-2H-pyran-2-yl-9H-purin-6-yl]-N-(2,2-diphenylethyl)amine (3.70 g, 8.63 mmol) (Preparation 6) and triethylamine (2.20 g, 21.78 mmol) in dry dichloromethane (20 ml) was treated with 2-methyl-1-propanesulphonyl chloride (1.48 g, 9.46 mmol) and the mixture was stirred at room temperature for 18 hours. TLC indicated that some starting material still remained and so further 2-methyl-1-propanesulphonyl chloride (0.2 g, 1.28 mmol) was added and the mixture was stirred at room temperature for 1 hour. The solvent was removed under reduced pressure and the residue was purified by column chromatography on silica gel eluting with dichloromethane:methanol (98:2 by volume) to afford the title compound as a foam (4.4 g).

$^1$H-NMR (CDCl$_3$) δ: 7.86 (1H, s), 7.16–7.36 (10H, m), 5.74 (1H, br s), 5.64 (1H, d), 5.57 (1H, t), 4.18–4.46 (5H, m), 4.14 (1H, d), 3.77 (1H, t), 2.92 (2H, d), 2.28 (1H, m) 1.92–2.10 (3H, m), 1.58–1.88 (3H, m), 1.03 (6H, d).

LRMS (thermospray): m/z [MH$^+$] 549.

Preparation 8

N-({6-[(2,2-Diphenylethyl)amino]-9H-purin-2-yl}methyl)-2-methyl-1-propanesulphonamide hydrochloride

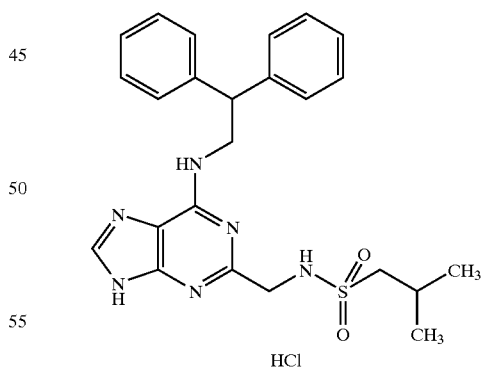

A solution of N-({6-[(2,2-diphenylethyl)amino]-9-tetrahydro-2H-pyran-2-yl-9H-purin-2-yl}methyl)-2-methyl-1-propanesulphonamide (4.30 g, 7.84 mmol) (Preparation 7) in ethanol (100 ml) was heated to 37° C. and then treated with 2M aqueous hydrochloric acid (15 ml). The mixture was left to stand at room temperature for 18 hours, after which time a crystalline precipitate was filtered off, washed with ethanol (10 ml) and dried to afford the title compound as a solid (3.0 g).

¹H-NMR (DMSO-d₆) δ: 8.48 (1H, br s), 7.75 (1H, br s), 7.37 (4H, d), 7.27 (4H, dd), 7.16 (2H, dd), 4.56 (1H, t), 4.20–4.40 (4H, m), 2.95 (2H, d), 2.10 (1H, m), 0.95 (6H, d).

Preparation 9

Methyl 6-[(2,2-diphenylethyl)amino]-9-tetrahydro-2H-pyran-2-yl-9H-purine-2-carboxylate

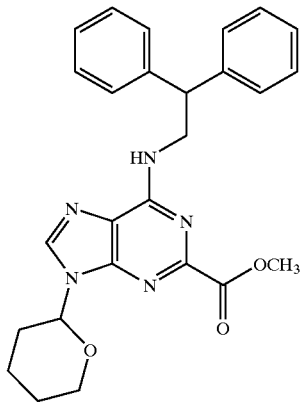

A suspension of 6-[(2,2-diphenylethyl)amino]-9-tetrahydro-2H-pyran-2-yl-9H-purine-2-carbonitrite (Preparation 5) (1.00 g, 2.36 mmol) in methanol (20 ml) was treated with sodium methoxide (0.14 g, 2.59 mmol) and the resulting mixture was heated at reflux under a nitrogen atmosphere for 20 hours. TLC analysis showed that some starting material still remained therefore further sodium methoxide (64 mg, 1.18 mmol) was added and the mixture was heated at reflux under a nitrogen atmosphere for a further hour. The mixture was then cooled to room temperature and the solvent was removed under reduced pressure. Tetrahydrofuran (30 ml) and water (10 ml) were added to the residue and the pH was adjusted to 4 by addition of acetic acid (1 ml). This mixture was heated under reflux for 1 hour. TLC analysis showed an incomplete reaction and therefore more acetic acid (0.5 ml) was added and heating under reflux continued for 18 hours. The reaction was cooled to room temperature and partitioned between ethyl acetate and a saturated aqueous solution of sodium hydrogen carbonate. The organic phase was separated, washed with brine, dried (anhydrous magnesium sulphate), filtered and evaporated under reduced pressure. The residue was purified by column chromatography on silica gel eluting with dichloromethane:methanol (98.5:1.5 by volume) to afford the title compound as a white solid (521 mg).

¹H-NMR (400 MHz, CDCl₃) δ: 8.05 (1H, br s), 7.37–7.18 (10H, m), 5.84 (2H, m), 4.40 (3H, m), 4.14 (1H, d), 4.00 (3H, s), 3.78 (1H, t), 2.17–1.60 (6H, m).

LRMS (thermospray): m/z [MH⁺] 458, [MNa⁺] 480.

Preparation 10

6-[(2,2-Diphenylethyl)amino]-N-[2-(1-piperidinyl)ethyl]-9-tetrahydro-2H-pyran-2-yl-9H-purine-2-carboxamide

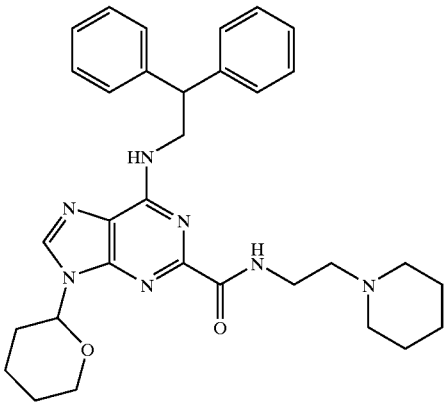

Methyl 6-[(2,2-diphenylethyl)amino]-9-tetrahydro-2H-pyran-2-yl-9H-purine-2-carboxylate (Preparation 9) (100 mg, 0.22 mmol) and 1-(2-aminoethyl)piperidine (0.31 ml, 2.19 mmol) were heated together at 130° C. for 2 hours. The excess amine was removed under reduced pressure and the residue was purified by column chromatography on silica gel eluting with dichloromethane:methanol (95:5 by volume) to afford the title compound as a yellow foam (104 mg).

¹H-NMR (400 MHz, CDCl₃) δ: 8.43 (1H, br m), 8.00 (1H, br s), 7.17–7.36 (10H, m), 5.94 (1H, d), 5.80 (1H, br m), 4.37 (3H, m), 4.33 (1H, d), 3.78 (1H, t), 3.57 (2H, m), 2.55 (2H, m), 2.40 (4H, br m), 1.65–2.17 (6H, m), 1.26–1.33 (6H, br m).

LRMS (thermospray): m/z [MH⁺] 554.

Preparation 11

6-[(2,2-Diphenylethyl)amino]-N-[2-(1-piperidinyl)ethyl]-9H-purine-2-carboxamide

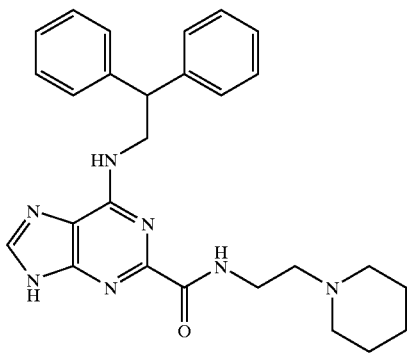

A solution of 6-[(2,2-diphenylethyl)amino]-N-[2-(1-piperidinyl)ethyl]-9-tetrahydro-2H-pyran-2-yl-9H-purine-2-carboxamide (Preparation 10) (420 mg, 0.76 mmol) in ethanol (20 ml) was treated with 2 M aqueous hydrochloric acid (0.9 ml). The mixture was heated under reflux for 30 minutes after which time a white precipitate had formed. The mixture was cooled to room temperature and the solvent was removed under reduced pressure. The residue was partitioned between dichloromethane and 10% weight by volume aqueous ammonia. The organic phase was separated, dried (anhydrous magnesium sulphate), filtered and evaporated under reduced pressure to afford the title compound as a white solid (319 mg).

¹H-NMR (400 MHz, CDCl₃) δ: 8.57 (1H, br m), 8.30 (1H, s), 7.40–7.20 (10H, m), 5.93 (1H, br s), 4.39 (3H, m), 3.62 (2H, m), 2.56 (2H, t), 2.40 (4H, br m), 1.47–1.24 (6H, br m).

LRMS (thermospray): m/z [MH⁺] 470, [MNa⁺] 492.

Preparation 12

N'-({[(3aS,4S,6R,6aR)-6-Methoxy-2,2-dimethyltetrahydrofuro[3,4-d][1,3]dioxol-4-yl]carbonyl}oxy)propanimidamide

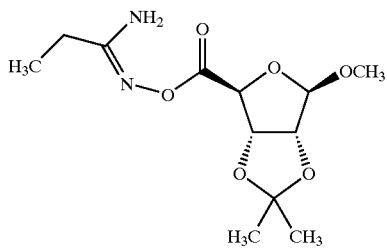

Oxalyl chloride (4 ml, 46 mmol) was added to a solution of (3aS,4S,6R,6aR)-6-methoxy-2,2-dimethyltetrahydrofuro[3,4-d][1,3]dioxole-4-carboxylic acid (*Justus Liebigs Ann. Chem.*, 1974, 11, 1856) (5 g, 23 mmol) in dichloromethane (100 ml). The solution was stirred at room temperature for two hours and then the solvent was evaporated under reduced pressure to yield a white solid. This was dissolved in ethyl acetate (80 ml) and N'-hydroxypropanimidamide (2.63 g, 30 mmol) was added followed by N-ethyldiisopropylamine (8.12 ml, 46 mmol). The reaction mixture was stirred at room temperature for 48 hours and then washed with saturated sodium hydrogencarbonate solution (50 ml) and brine (50 ml). The organic layer was separated, dried (anhydrous magnesium sulphate) and evaporated under reduced pressure to give the product as a dark yellow oil (5.85 g).

¹H-NMR (400 MHz, CDCl₃) δ: 5.20 (1H, d), 5.05 (1H, s), 4.70 (1H, s), 4.60 (1H, d), 3.40 (3H, s), 2.30 (2H, q), 1.50 (3H, s), 1.30 (3H, s), 1.20 (3H, t).

LRMS (thermospray): m/z [MH⁺] 289.

Preparation 13

5-[(3aR,4S,6R,6aR)-6-Methoxy-2,2-dimethyltetrahydrofuro[3,4-d][1,3]dioxol-4-yl]-3-ethyl-1,2,4-oxadiazole

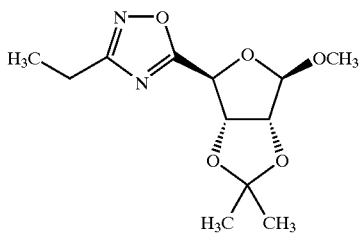

A solution of N'-({[(3aS,4S,6R,6aR)-6-methoxy-2,2-dimethyltetrahydrofuro[3,4-d][1,3]dioxol-4-yl]carbonyl}oxy)propanimidamide (Preparation 12) (5.85 g, 20 mmol) in 2-methoxyethyl ether (20 ml) was heated at 120° C. for four hours. The reaction mixture was allowed to cool to room temperature and evaporated under reduced pressure. The final traces of 2-methoxyethyl ether were removed by co-evaporation with first xylene and then toluene. The title compound was obtained as a dark orange oil (5.22 g).

¹H-NMR (400 MHz, CDCl₃) δ: 5.50 (1H, d), 5.25 (1H, s), 5.10 (1H, s), 4.60 (1H, d), 3.20 (3H, s), 2.75 (2H, q), 1.50 (3H, s), 1.40–1.30 (6H, m).

Preparation 14

(2R,3R,4R,5S)-2,4-bis(Acetoxy)-5-(3-ethyl-1,2,4-oxadiazol-5-yl)tetrahydro-3-furanyl acetate and (2S,3R,4R,5S)-2,4-bis(acetoxy)-5-(3-ethyl-1,2,4-oxadiazol-5-yl)tetrahydro-3-furanyl acetate

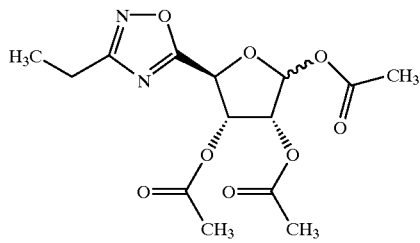

A solution of 5-[(3aR,4S,6R,6aR)-6-methoxy-2,2-dimethyltetrahydrofuro[3,4-d][1,3]dioxol-4-yl]-3-ethyl-1,2,4-oxadiazole (Preparation 13) (5.2 g, 19 mmol) in a mixture of trifluoroacetic acid (10 ml) and water (1 ml) was stirred at room temperature for 12 hours. The solvent was evaporated under reduced pressure and the final traces of trifluoroacetic acid were removed by co-evaporation with toluene. The residual dark oil was dissolved in pyridine (50 ml), acetic anhydride (18 ml, 0.19 mol) was added and the mixture was stirred at room temperature for 12 hours. The reaction mixture was evaporated to dryness and the residue was dissolved in diethyl ether (100 ml) and washed with water (30 ml). The organic layer was separated, dried (anhydrous magnesium sulphate) and evaporated under reduced pressure. TLC analysis showed two major products that were separated by column chromatography on silica gel eluting with a gradient system of dichloromethane:methanol (99.5:0.5 by volume) gradually changing to dichloromethane:methanol (98:2 by volume). The more polar component (TLC data—R_f 0.49 in solvent system dichloromethane:methanol 98:2 by volume) was identified as a 2:1 anomeric mixture of the title compounds (0.93 g).

¹H-NMR (400 MHz, CDCl₃) δ: 6.60 (1H', m), 6.30 (1H, s), 5.80 (1H, m), 5.60 (1H', m), 5.55–5.40 (1H+1H', m), 5.40 (1H', s), 5.30 (1H, m), 2.80 (2H+2H', q), 1.40–1.30 (3H+3H', m).

LRMS (thermospray): m/z [MH⁺] 343.

Preparation 15

Benzyl 2-{[(3aS,4S,6R,6aR)-6-methoxy-2,2-dimethyltetrahydrofuro[3,4-d][1,3]dioxol-4-yl]carbonyl}hydrazinecarboxylate

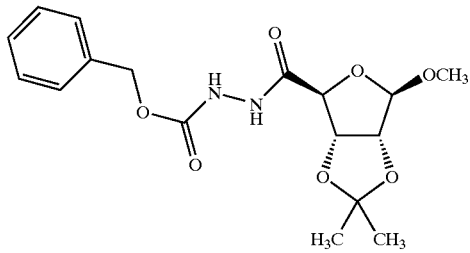

Oxalyl chloride (3.5 ml, 40 mmol) was added to a solution of (3aS,4S,6R,6aR)-6-methoxy-2,2-dimethyltetrahydrofuro[3,4-d][1,3]dioxole-4-carboxylic acid (*Justus Liebigs Ann. Chem.*, 1974, 11, 1856) (3 g, 13.8 mmol) in dichloromethane (25 ml). The solution was stirred at room temperature for 3 hours and the solvent was then evaporated under reduced pressure. The acid chloride was re-dissolved in dichloromethane (25 ml) and treated with benzyl carbazate (2.3 g, 13.8 mmol) and triethylamine (5.7 ml, 41.4 mmol). After having been stirring at room temperature for 12 hours, the mixture was partioned between ethyl acetate (100 ml) and water (50 ml). The ethyl acetate layer was separated, washed with 1M aqueous citric acid solution (50 ml), saturated sodium hydrogencarbonate solution (50 ml) and brine (50 ml) and dried (anhydrous sodium sulphate). Evaporation of solvent under reduced pressure yielded the title compound as a yellow foam (4.87 g).

$^1$H-NMR (400 MHz, CDCl$_3$) δ: 8.35 (1H, s), 7.40–7.30 (5H, m), 6.80 (1H, br s), 5.20 (2H, s), 5.20–5.05 (2H, m), 4.70 (1H, s), 4.60 (1H, br s), 3.50–3.30 (2H, m), 1.45 (3H, s), 1.30 (3H, s).

LRMS (thermospray): m/z [MNH$_4^+$] 384.

Preparation 16

(3aS,4S,6R,6aR)-6-Methoxy-2,2-dimethyltetrahydrofuro[3,4-d][1,3]dioxole-4-carbohydrazide

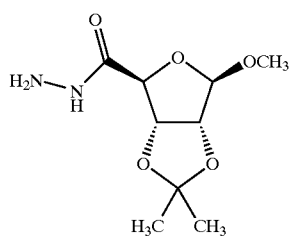

A solution of benzyl 2-{[(3aS,4S,6R,6aR)-6-methoxy-2,2-dimethyltetrahydrofuro[3,4-d][1,3]dioxol-4-yl]carbonyl}hydrazinecarboxylate (Preparation 15) (4.87 g, 13.3 mmol) in ethanol (60 ml) was hydrogenated over 10% w/w palladium on carbon (0.3 g) at 414 kPa (60 p.s.i), room temperature for 6 hours. The catalyst was removed by filtration and the filtrate was evaporated under reduced pressure to give the title compound as a yellow oil (3.56 g).

$^1$H-NMR (400 MHz, CDCl$_3$) δ: 7.70 (1H, br s), 5.10 (1H, d), 5.05 (1H, s), 4.65 (1H, s), 4.55 (1H, d), 3.90–3.60 (2H, br s), 3.40 (3H, s), 1.45 (3H, s), 1.30 (3H, s).

Preparation 17

2-{[(3aS,4S,6R,6aR)-6-Methoxy-2,2-dimethyltetrahydrofuro[3,4-d][1,3]dioxol-4-yl]carbonyl}-N-benzylhydrazinecarbothioamide

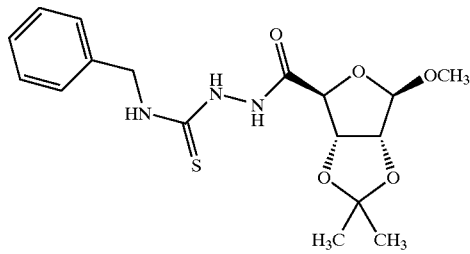

A solution of (3aS,4S,6R,6aR)-6-methoxy-2,2-dimethyltetrahydrofuro[3,4-d][1,3]dioxole-4-carbohydrazide (Preparation 16) (4 g, 17.2 mmol) and benzyl isothiocyanate (2.38 ml, 18 mmol) in dichloromethane (50 ml) was stirred at room temperature for 12 hours. The solvent was removed by evaporation under reduced pressure and the residue was partioned between dichloromethane (100 ml) and water (100 ml). The organic layer was separated, dried (anhydrous magnesium sulphate) and evaporated under reduced pressure to give the title compound (5.90 g) which was used without further purification.

$^1$H-NMR (400 MHz, CDCl$_3$) δ: 8.80 (1H, br s), 8.30 (1H, br s), 7.40–7.20 (5H, m), 7.10 (1H, m), 5.05 (1H, d), 5.00 (1H, s), 4.85 (1H, m), 4.75 (1H, m), 4.65 (1H, s), 4.30 (1H, d), 3.25 (3H, s), 1.45 (3H, s), 1.30 (3H, s).

LRMS (thermospray): m/z [MNH$_4^+$] 382.

Preparation 18

5-[(3aR,4R,6R,6aR)-6-Methoxy-2,2-dimethyltetrahydrofuro[3,4-d][1,3]dioxol-4-yl]-4-benzyl-2,4-dihydro-3H-1,2,4-triazole-3-thione

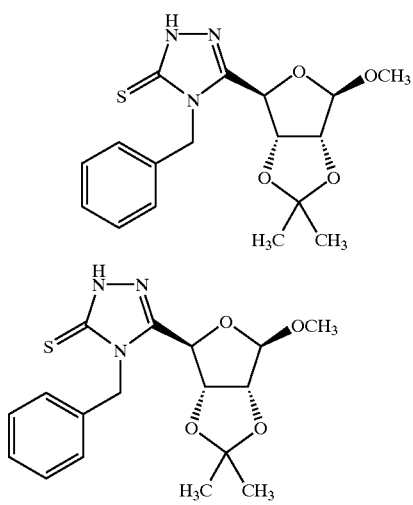

A solution of 2-{[(3aS,4S,6R,6aR)-6-methoxy-2,2-dimethyltetrahydrofuro[3,4-d][1,3]dioxol-4-yl]carbonyl}-N-benzylhydrazinecarbothioamide (Preparation 17) (5.9 g, 15.5 mmol) in 2 M aqueous sodium hydroxide (200 ml) was heated under reflux for 2 hours. The solution was allowed to cool to room temperature and extracted with dichloromethane (50 ml). The aqueous phase was then acidified to pH 4 with 2 M aqueous hydrochloric acid and extracted with ethyl acetate (300 ml). The ethyl acetate layer was dried (anhydrous magnesium sulphate) and evaporated under reduced pressure to give the title compound (2.20 g).

$^1$H-NMR (400 MHz, CDCl$_3$) δ: 7.40–7.30 (5H, m), 5.80 (1H, d), 5.55 (1H, d), 5.20 (1H, d), 5.05 (1H, s), 4.80 (1H, s), 4.65 (1H, d), 3.15 (3H, s), 1.45 (3H, s), 1.30 (3H, s).

Preparation 19

3-[(3aR,4R,6R,6aR)-6-Methoxy-2,2-dimethyltetrahydrofuro[3,4-d][1,3]dioxol-4-yl]-4-benzyl-4H-1,2,4-triazole

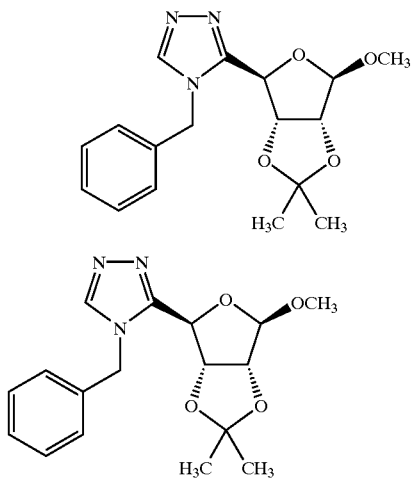

A solution of 5-[(3aR,4R,6R,6aR)-6-methoxy-2,2-dimethyltetrahydrofuro[3,4-d][1,3]dioxol-4-yl]-4-benzyl-2,4-dihydro-3H-1,2,4-triazole-3-thione (Preparation 18) (2.2 g, 6.1 mmol) in acetic acid (30 ml) was treated portionwise with sodium nitrite (1.2 g, 18 mmol) over 30 minutes. After an additional 30 minutes, the solvent was removed by evaporation under reduced pressure and the residue was suspended in acetone (30 ml). The insoluble inorganic salts were removed by filtration and the filtrate was evaporated under reduced pressure. The residue was then dissolved in dichloromethane (30 ml), the mixture was filtered again and the filtrate was evaporated under reduced pressure to give the title compound (2.0 g).

$^1$H-NMR (400 MHz, CDCl$_3$) δ: 8.10 (1H, s), 7.40–7.30 (3H, m), 7.20 (2H, m), 5.95 (1H, d), 5.40 (1H, AB system), 5.25 (1H, AB System), 5.10 (1H, s), 5.05 (1H, s), 4.80 (1H, d), 3.05 (3H, s), 1.50 (3H, s), 1.35 (3H, s).

LRMS (thermospray): m/z [MH$^+$] 332.

Preparation 20

3-[(3aR,4R,6R,6aR)-6-Methoxy-2,2-dimethyltetrahydrofuro[3,4-d][1,3]dioxol-4-yl]-4H-1,2,4-triazole

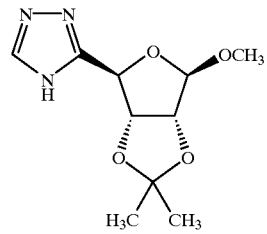

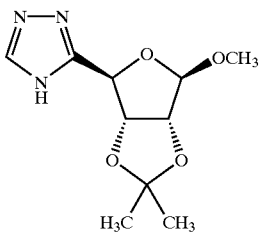

A solution of 3-[(3aR,4R,6R,6aR)-6-methoxy-2,2-dimethyltetrahydrofuro[3,4-d][1,3]dioxol-4-yl]-4-benzyl-4H-1,2,4-triazole (Preparation 19) (1.5 g, 4.5 mmol) in ethyl acetate (45 ml) and ethanol (5 ml) was hydrogenated over palladium black (0.4 g) at 2758 kPa (400 p.s.i) and 100 °C. for 24 hours. Additional palladium black (0.2 g) was then added and hydrogenation was continued for a further 72 hours. The catalyst was removed by filtration and the filtrate was evaporated under reduced pressure to give the title compound (1.0 g).

$^1$H-NMR (400 MHz, CDCl$_3$) δ: 8.00 (1H, s), 5.50 (1H, s), 5.20–5.10 (2H, m), 4.70 (1H, d), 3.40 (3H, s), 1.55 (3H, s), 1.35 (3H, s).

LRMS (thermospray): m/z [MH$^+$] 242.

Preparation 21

3-[(3aR,4R,6R,6aR)-6-Methoxy-2,2-dimethyltetrahydrofuro[3,4-d][1,3]dioxol-4-yl]-1-ethyl-1H-1,2,4-triazole

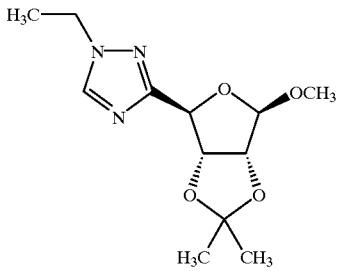

-continued

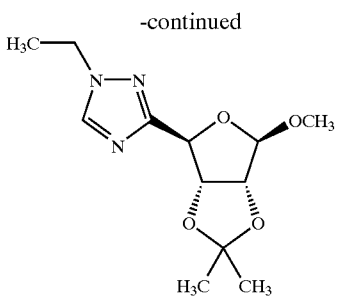

A solution of 3-[(3aR,4R,6R,6aR)-6-methoxy-2,2-dimethyltetrahydrofuro[3,4-d][1,3]dioxol-4-yl]-4H-1,2,4-triazole (Preparation 20) (1.0 g, 4.2 mmol), potassium carbonate (0.57 g, 4.2 mmol) and iodoethane (0.33 ml, 4.2 mmol) in acetone (10 ml) was heated under reflux for one hour. Further iodoethane (0.05 ml, 0.6 mmol) and potassium carbonate (0.1 g, 0.7 mmol) were added and heating under reflux continued for 30 minutes. The reaction mixture was allowed to cool to room temperature and the solvent was evaporated under reduced pressure. The residue was purified by column chromatography on silica gel eluting with a gradient system of dichloromethane gradually changing to dichloromethane:methanol (97:3 by volume) to give the title compound (0.4 g) (TLC data—$R_f$ 0.65 in solvent system dichloromethane:methanol 95:5 by volume).

$^1$H-NMR (400 MHz, CDCl$_3$) δ: 8.00 (1H, s), 5.50 (1H, d), 5.25 (1H, s), 5.05 (1H, s), 4.70 (1H, d), 4.20 (2H, q), 3.20 (3H, s), 1.55 (3H, s), 1.50 (3H, t), 1.35 (3H, s).

LRMS (thermospray): m/z [MH$^+$] 270.

Preparation 22

(2R,3R,4R,5R)-3,4-bis(Benzoyloxy)-5-(1-ethyl-1H-1,2,4-triazol-3-yl)tetrahydro-2-furanyl benzoate and (2S,3R,4R,5R)-3,4-bis(benzoyloxy)-5-(1-ethyl-1H-1,2,4-triazol-3-yl)tetrahydro-2-furanyl benzoate

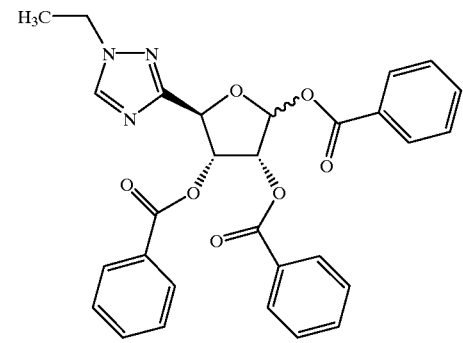

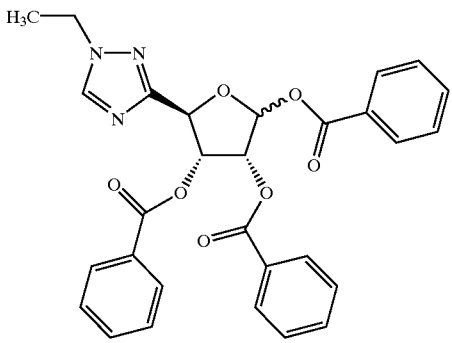

A solution of 3-[(3aR,4R,6R,6aR)-6-methoxy-2,2-dimethyltetrahydrofuro[3,4-d][1,3]dioxol-4-yl]-1-ethyl-1H-1,2,4-traizole (Preparation 21) (0.4 g, 1.5 mmol), in 2 M aqueous hydrochloric acid (5 ml) was heated at 60 °C. for two hours. The reaction mixture was allowed to cool to room temperature and the solvent was evaporated under reduced pressure. The residue was dissolved in pyridine (6 ml) and benzoyl chloride (4 ml, 17 mmol) was added. The reaction mixture was stirred at room temperature overnight and then diluted with dichloromethane (60 ml). The solution was washed with 2 M aqueous hydrochloric acid (50 ml), dried (anhydrous magnesium sulphate) and evaporated under reduced pressure to give an oil. Purification by column chromatography on silica gel eluting with a gradient system of ethyl acetate:pentane (60:40 by volume) gradually changing to ethyl acetate gave the title compounds as a 1:1 mixture of anomers (0.7 g).

$^1$H-NMR (400 MHz, CDCl$_3$) δ: 8.20–7.80 (6H, m), 7.60–7.20 (9H, m), 7.05 (0.5H, d), 6.80 (0.5H, s), 6.45 (0.5H, m), 6.20–6.10 (1.5H, m), 5.70 (0.5H, s), 5.60 (0.5H, d), 4.25 (1H, q), 4.15 (1H, m), 1.55 (1.5H, t), 1.40 (1.5H, t).

LRMS (thermospray): m/z [MH$^+$] 528.

Preparation 23

4-[(3aR,4R,6R,6aR)-6-Methoxy-2,2-dimethyltetrahydrofuro[3,4-d][1,3]dioxol-4-yl]-2H-1,2,3-triazole

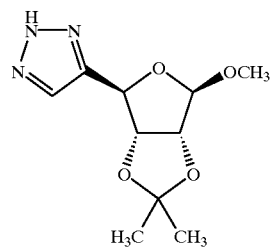

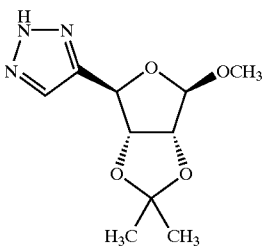

A solution of (3aR,4R,6R,6aR)-4-ethynyl-6-methoxy-2,2-dimethyltetrahydrofuro[3,4-d][1,3]dioxole (*Helv. Chim. Acta,* 1980, 63(5), 1181) (0.55 g, 2.8 mmol), in trimethylsilylazide (5 ml) was heated at 120 °C. in a teflon lined bomb for 12 hours. The reaction mixture was allowed to cool to room temperature and the solvent was evaporated under reduced pressure. The residue was purified by column chromatography on silica gel eluting with a gradient system of dichloromethane gradually changing to dichloromethane:methanol (98:2 by volume) to give the title compound as a pale brown oil which solidified on standing (0.36 g).

$^1$H-NMR (400 MHz, CDCl$_3$) δ: 7.70 (1H, s), 5.40 (1H, s), 5.15 (1H, m), 5.10 (1H, s), 4.70 (1H, m), 3.20 (3H, s), 1.55 (3H, s), 1.35 (3H, s).

LRMS (thermospray): m/z [MH$^+$] 242.

Preparation 24

4-[(3aR,4R,6R,6aR)-6-Methoxy-2,2-dimethyltetrahydrofuro[3,4-d][1,3]dioxol-4-yl]-1-ethyl-1H-1,2,3-triazole

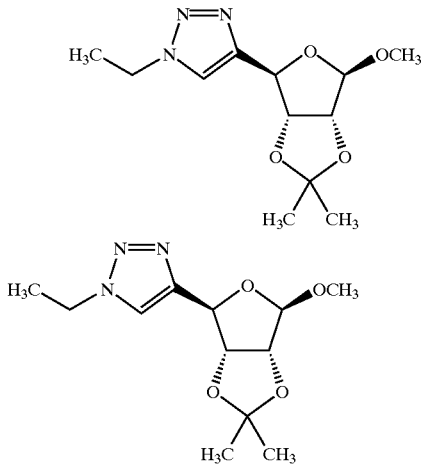

A solution of 4-[(3aR,4R,6R,6aR)-6-methoxy-2,2-dimethyltetrahydrofuro[3,4-d][1,3]dioxol-4-yl]-2H-1,2,3-triazole (Preparation 23) (0.35 g, 1.45 mmol), potassium carbonate (0.2 g, 1.45 mmol) and iodoethane (0.12 ml, 1.45 mmol) in acetone (5 ml) was stirred at room temperature for 48 hours. The reaction mixture was allowed to cool to room temperature, filtered and evaporated under reduced pressure. The residue was purified by column chromatography on silica gel eluting with a gradient system of dichloromethane:methanol (99.7:0.3 by volume) gradually changing to dichloromethane:methanol (99:1 by volume) to give initially 4-[(3aR,4R,6R,6aR)-6-methoxy-2,2-dimethyltetrahydrofuro[3,4-d][1,3]dioxol-4-yl]-2-ethyl-2H-1,2,3-triazole (0.18 g) followed by the title compound (TLC data—$R_f$ 0.25 in solvent system dichloromethane:methanol 98:2 by volume) contaminated with 25% of 5-[(3aR,4R,6R,6aR)-6-methoxy-2,2-dimethyltetrahydrofuro[3,4-d][1,3]dioxol-4-yl]-1-ethyl-1H-1,2,3-triazole (0.16 g). This material was used in subsequent steps without further purification.

$^1$H-NMR (400 MHz, CDCl$_3$) δ: 7.45 (1H, s), 5.40 (1H, s), 5.20 (1H, m), 5.10 (1H, s), 4.70 (1H, d), 4.40 (2H, q), 3.20 (3H, s), 1.60–1.50 (6H, m), 1.35 (3H, s).

LRMS (thermospray): m/z [MH$^+$] 270.

Preparation 25

(2S,3R,4R,5R)-3,4-bis(Benzoyloxy)-5-(1-ethyl-1H-1,2,3-triazol-4-yl)tetrahydro-2-furanyl benzoate

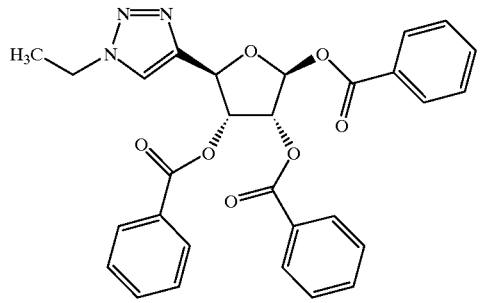

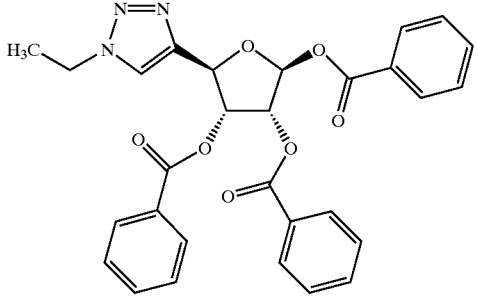

A solution of 4-[(3aR,4R,6R,6aR)-6-methoxy-2,2-dimethyltetrahydrofuro[3,4-d][1,3]dioxol-4-yl]-1-ethyl-1H-1,2,3-traizole (Preparation 24) (0.22 g, 0.82 mmol) in 2 M aqueous hydrochloric acid (3 ml) and methanol (6 ml) was heated at 50° C. for 12 hours. The reaction mixture was allowed to cool to room temperature and solvent was evaporated under reduced pressure. The residue was disolved in pyridine (0.3 ml) and dichloromethane (10 ml) and benzoyl chloride (0.29 ml, 2.48 mmol) were added. The reaction mixture was stirred at room temperature for one hour and then the solvent was removed by evaporation under reduced pressure. The residue was purified by column chromatography on silica gel eluting with dichloromethane:methanol (99.5:0.5 by volume) to give the title compound as a white solid (0.05 g) (TLC data—$R_f$ 0.54 in solvent system dichloromethane:methanol 99:1 by volume).

$^1$H-NMR (400 MHz, CDCl$_3$) δ: 8.10–7.85 (6H, m), 7.60–7.30 (10H, m), 6.70 (1H, s), 6.25 (1H, m), 6.05 (1H, m), 5.70 (1H, m), 4.25 (2H, q), 1.40 (3H, t).

LRMS (thermospray): m/z [MH$^+$] 528.

Preparation 26

(2R,3R,4R,5R)-4-(Acetyloxy)-2-(6-[(2,2-diphenylethyl)amino]-2-{[(isobutylsulphonyl)amino]methyl}-9H-purin-9-yl)-5-(2-ethyl-2H-tetrazol-5-yy)tetrahydro-3-furanyl acetate

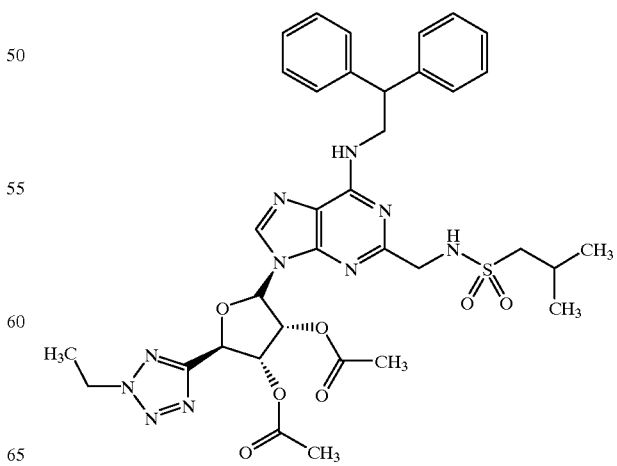

-continued

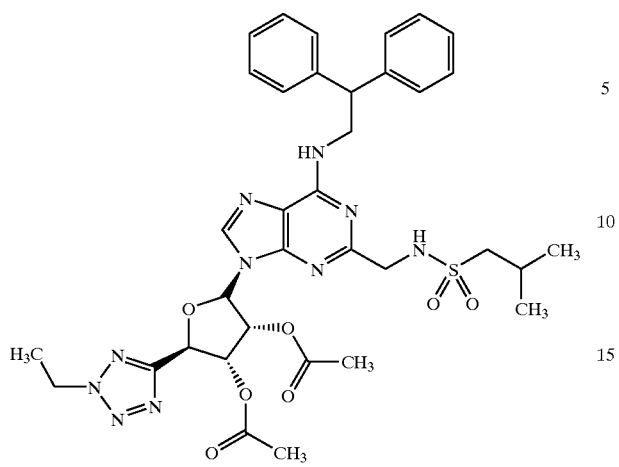

A suspension of N-({6-[(2,2-diphenylethyl)amino]-9H-purin-2-yl}methyl)-2-methyl-1-propanesulphonamide hydrochloride (Preparation 8) (0.2 g, 0.40 mmol) in 1,1,1-trichloroethane (10 ml) was treated with N,O-bis(trimethylsilylacetamide) (0.6 ml, 2.45 mmol) and the mixture was heated under reflux for 2 hours. The solvent was removed under reduced pressure and the residue was twice azeotroped with toluene. The residue was dissolved in toluene (5 ml) and treated sequentially with a solution of (2R,3R,4R)-4,5-bis(acetyloxy)-2-(2-ethyl-2H-tetrazol-5-yl)tetrahydro-3-furanyl acetate (WO-A-9967265) (0.165 g, 0.48 mmol) in toluene (5 ml) and then trimethylsilyltriflate (0.09 ml, 0.49 mmol). The mixture was heated under reflux for 3 hours and then allowed to stand at room temperature overnight. The solution was diluted with ethyl acetate (40 ml), washed sequentially with saturated aqueous sodium hydrogen carbonate solution (20 ml) and brine (20 ml), dried (anhydrous magnesium sulphate) and evaporated under reduced pressure. The residue was purified by column chromatography on silica gel eluting with a gradient system of dichloromethane:ethyl acetate (4:1 by volume) gradually changing to dichloromethane:ethyl acetate (2:1 by volume) to afford the title compound (0.24 g).

$^1$H-NMR (400 MHz, CDCl$_3$) δ: 8.10 (1H, s), 7.35–7.20 (10H, m), 6.30 (1H, m), 6.20 (1H, m), 6.05 (1H, m), 5.85 (1H, br s), 5.75 (1H, br s); 5.55 (1H, d), 4.70 (2H, q), 4.45–4.20 (5H, m), 2.95 (2H, d), 2.30 (1H, m), 2.20 (3H, s), 2.10 (3H, s), 1.65 (3H, t), 1.05 (6H, d).

LRMS (thermospray): m/z [MH$^+$] 747.

Preparation 27

(2R,3R,4R,5R)-4-(Acetyloxy)-2-[6-[(2,2-diphenylethyl)amino]-2-({[2-(1-piperidinyl)ethyl]amino}carbonyl)-9H-purin-9-yl]-5-(2-ethyl-2H-tetrazol-5-yl)tetrahydro-3-furanyl acetate

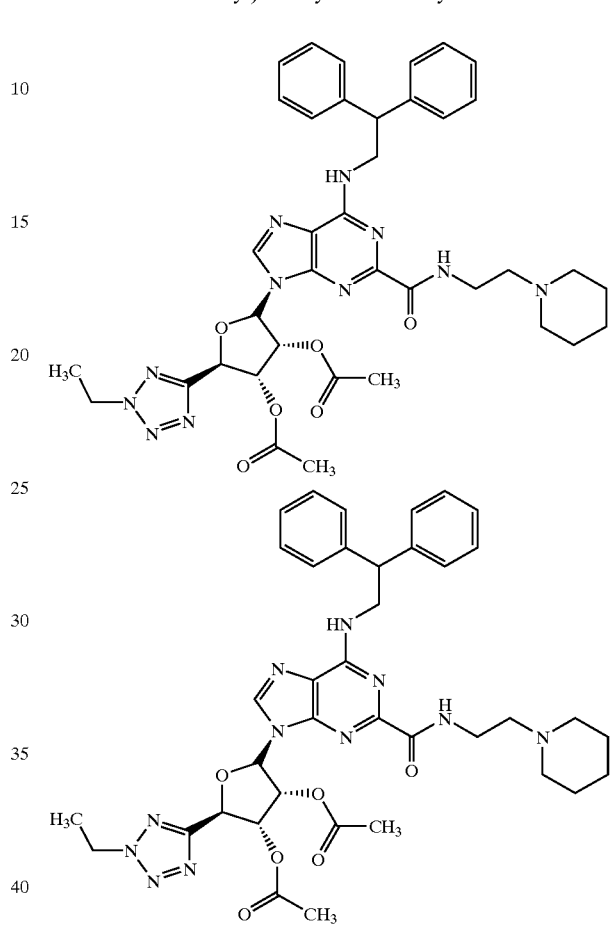

A suspension of 6-[(2,2-diphenylethyl)amino]-N-[2-(1-piperidinyl)ethyl]-9H-purine-2-carboxamide (Preparation 11) (0.2 g, 0.42 mmol) in 1,1,1-trichloroethane (10 ml) was treated with N,O-bis(trimethylsilylacetamide) (0.65 ml, 2.65 mmol) and the mixture was heated under reflux for 2 hours. The solvent was removed under reduced pressure and the residue was twice azeotroped with toluene. The residue was dissolved in toluene (5 ml) and treated sequentially with a solution of (2R,3R,4R)-4,5-bis(acetyloxy)-2-(2-ethyl-2H-tetrazol-5-yl)tetrahydro-3-furanyl acetate (WO-A-9967265) (0.175 g, 0.51 mmol) in toluene (5 ml) and then trimethylsilyltriflate (0.1 ml, 0.55 mmol). The mixture was heated under reflux for 3 hours and then allowed to stand at room temperature overnight. The solution was diluted with ethyl acetate (40 ml), washed sequentially with saturated aqueous sodium hydrogen carbonate solution (20 ml) and brine (20 ml) and evaporated under reduced pressure. The residue was purified by column chromatography on silica gel eluting with a gradient system of dichloromethane:methanol (93:7 by volume) gradually changing to dichloromethane:methanol (90:10 by volume) to afford the title compound (0.235 g).

¹H-NMR (400 MHz, CDCl₃) δ: 8.45 (1H, br s), 8.40 (1H, s), 7.35–7.20 (10H, m), 6.70 (1H, br s), 6.20 (1H, br s), 5.85–5.75 (2H, m), 5.55 (1H, d); 4.70 (2H, q), 4.40–4.20 (3H, m), 3.60 (2H, m), 2.50 (2H, m), 2.35 (4H, m), 2.20 (3H, s), 2.05 (3H, s), 1.65 (3H, t), 1.60–1.25 (6H, m).

LRMS (thermospray): m/z [MH⁺] 753.

Preparation 28

6-[(2,2-Diphenylethyl)amino]-9H-purine-2-carbonitrile

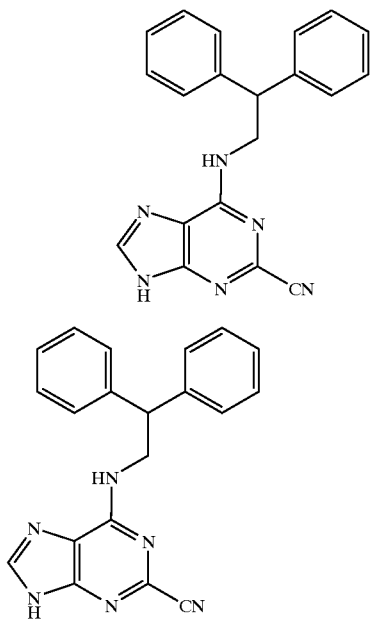

A solution of 6-[(2,2-diphenylethyl)amino]-9-(tetrahydro-2H-pyran-2-yl)-9H-purine-2-carbonitrile (Preparation 5) (17 g, 40.1 mmol) in ethanol (850 ml) was treated with 2 M aqueous hydrochloric acid (50 ml) and the mixture was stirred at room temperature for 24 hours. The solvent was removed under reduced pressure, the residue was dissolved in ethanol and the solvent was again removed under reduced pressure. The residue was triturated with diethyl ether, filtered, washed with diethyl ether and pentane, and dried to afford the title compound as a solid (13.6 g).

¹H-NMR (400 MHz, DMSO-d₆) δ: 8.30 (1H, s), 8.20–8.05 (1H, br s), 7.40–7.10 (10H, m), 4.60–4.40 (1.4H, m), 4.20–4.00 (1.6H, m).

LRMS (thermospray): m/z [MH⁺] 341.

Preparation 29

Methyl 6-[(2,2-diphenylethyl)amino]-9H-purine-2-carboxylate

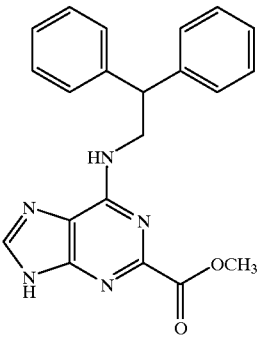

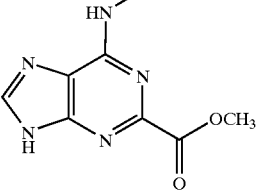

A solution of 6-[(2,2-diphenylethyl)amino]-9H-purine-2-carbonitrile (Preparation 28) (5.0 g, 14.7 mmol) and sodium methoxide (4.0 g, 74.1 mmol) in methanol (300 ml) was heated under reflux for 24 hours. Further sodium methoxide (2.0 g, 37 mmol) and methanol (100 ml) were added and heating was continued for a further 24 hours. The reaction mixture was allowed to cool and the solvent was removed under reduced pressure. The residue was dissolved in tetrahydrofuran (375 ml), 2 M aqueous hydrochloric acid (125 ml) was added and the mixture was stirred at room temperature for 24 hours. The tetrahydrofuran was removed under reduced pressure and the pH of the suspension was adjusted to 7 with saturated aqueous sodium bicarbonate solution. Ethyl acetate (100 ml) was added and the white solid consisting mainly of the desired product was filtered, washed with a little water and ethyl acetate and dried. Purification by column chromatography on silica gel eluting with a gradient system of dichloromethane:methanol (90:10 by volume) gradually changing to dichloromethane:methanol (75:25 by volume) afforded the title compound as a white solid (1.25 g). Evaporation of the ethyl acetate filtrate provided 2.6 g of the starting material.

¹H-NMR (400 MHz, CDCl3) δ: 12.40 (1H, br s), 8.05 (1H, s), 7.55 (1H, s), 7.30–7.20 (10H, m), 4.80 (2H, m), 4.75 (1H, m), 3.80 (3H, s).

LRMS (thermospray): m/z [MH⁺] 375.

Preparation 30

Methyl 9-[(2R,3R,4R,5R)-3,4-bis(acetyloxy)-5-(2-ethyl-2H-tetraazol-5-yl)tetrahydro-2-furanyl]-6-[(2,2-diphenylethyl)amino]-9H-purine-2-carboxylate

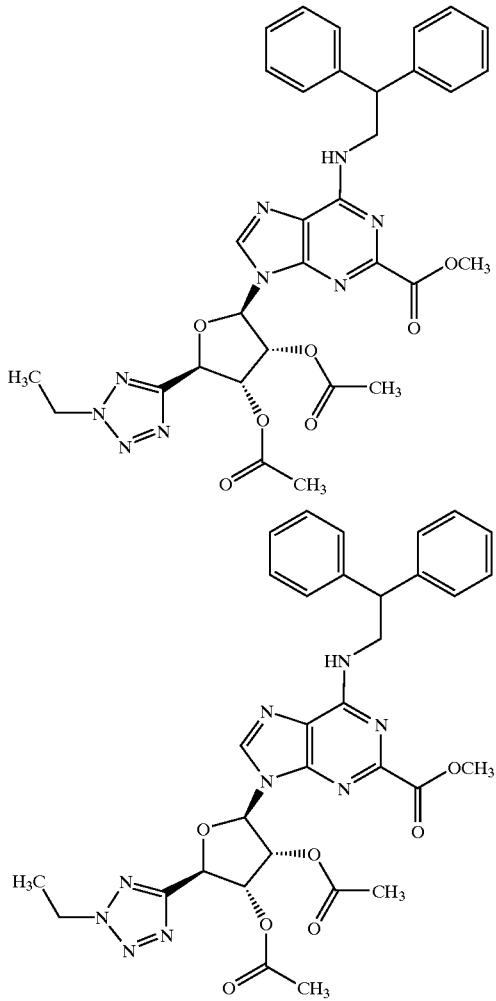

A suspension of methyl 6-[(2,2-diphenylethyl)amino]-9H-purine-2-carboxylate (Preparation 29) (0.4 g, 1.07 mmol) in 1,1,1-trichloroethane (25 ml) was treated with N,O-bis(trimethylsilylacetamide) (1.6 ml, 6.54 mmol) and the mixture was heated under reflux for one hour. The solvent was removed under reduced pressure and the residue was twice azeotroped with toluene. The residue was dissolved in toluene (5 ml) and treated sequentially with a solution of (2R,3R,4R)-4,5-bis(acetyloxy)-2-(2-ethyl-2H-tetrazol-5-yl)tetrahydro-3-furanyl acetate (WO-A-9967265) (0.45 g, 1.31 mmol) in toluene (20 ml) and then trimethylsilyltriflate (0.25 ml, 1.37 mmol). The mixture was heated under reflux for 3 hours and then allowed to stand at room temperature overnight. The solution was diluted with ethyl acetate (40 ml), washed sequentially with saturated aqueous sodium hydrogen carbonate solution (20 ml) and brine (20 ml), dried (anhydrous magnesium sulphate) and evaporated under reduced pressure. The residue was purified by column chromatography on silica gel eluting with a gradient system of dichloromethane:ethyl acetate (80:20 by volume) gradually changing to dichloromethane:ethyl acetate (60:40 by volume) to afford the title compound (0.44 g).

$^1$H-NMR (400 MHz, CDCl$_3$) δ: 8.45 (1H, br s), 7.35–7.20 (10H, m), 6.70 (1H, m), 6.20 (1 H, br s), 5.85–5.75 (2H, m), 5.55 (1H, m); 4.80–4.65 (3H, m), 4.45–4.25 (2H, m), 4.00 (3H, s), 2.20 (3H, s), 2.05 (3H, s), 1.65 (3H, t).

LRMS (thermospray): m/z [MH$^+$] 656.

Preparation 31

(2R,3R,4S,5S)-4-(Acetyloxy)-2-(6-[(2,2-diphenylethyl)amino]-2-{[(isobutylsulphonyl)amino]methyl}-9H-purin-9-yl)-5-(3-ethyl-1,2,4-oxadiazol-5-yl)tetrahydro-3-furanyl acetate

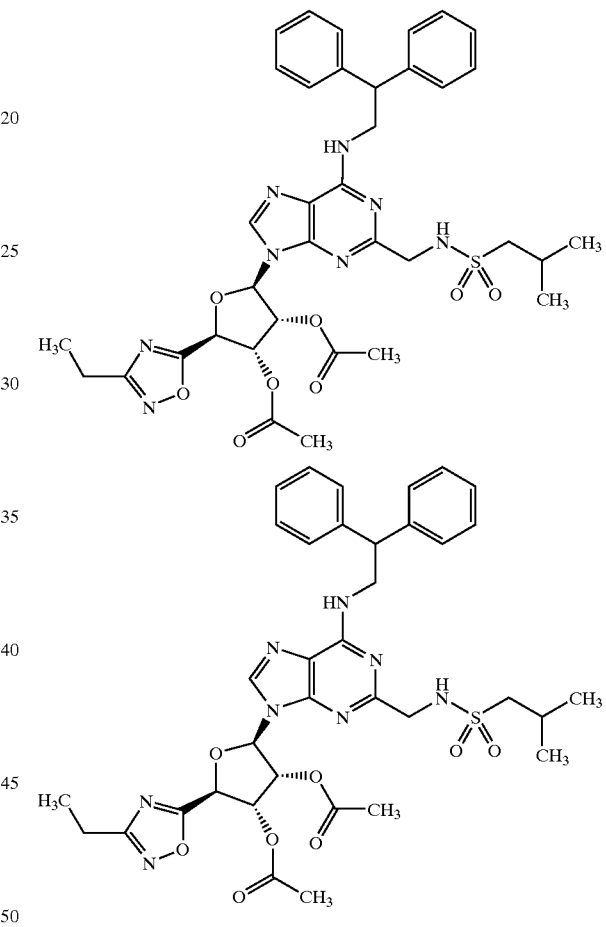

Prepared by the same method as Preparation 26 from N-({6-[(2,2-diphenylethyl)amino]-9H-purin-2-yl}methyl)-2-methyl-1-propanesulphonamide hydrochloride (Preparation 8) and a mixture of (2R,3R,4R,5S)-2,4-bis(acetoxy)-5-(3-ethyl-1,2,4-oxadiazol-5-yl)tetrahydro-3-furanyl acetate and (2S,3R,4R,5S)-2,4-bis(acetoxy)-5-(3-ethyl-1,2,4-oxadiazol-5-yl)tetrahydro-3-furanyl acetate (Preparation 14).

$^1$H-NMR (400 MHz, CDCl$_3$) δ: 8.10 (1H, s), 7.35–7.20 (10H, m), 6.30 (1H, m), 6.15 (1H, m), 6.05 (1H, m), 5.85 (1H, br s), 5.75 (1H, br s); 5.40 (1H, d), 4.45–4.20 (5H, m), 2.95 (2H, d), 2.80 (2H, q), 2.30 (1H, m), 2.20 (3H, s), 2.10 (3H, s), 1.35 (3H, t), 1.05 (6H, d).

LRMS (thermospray): m/z [MH$^+$] 747.

Preparation 32

(2R,3R,4R,5S)-4-(Acetyloxy)-2-[6-[(2,2-diphenylethyl)amino]-2-({[2-(1-piperidinyl)ethyl]amino}carbonyl)-9H-purin-9-yl]-5-(3-ethyl-5-isoxazolyl)tetrahydro-3-furanyl acetate

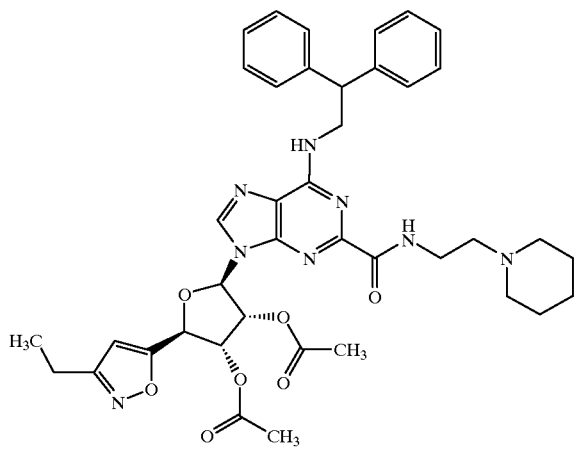

Prepared by the same method as Preparation 27 from 6-[(2,2-diphenylethyl)amino]-N-[2-(1-piperidinyl)ethyl]-9H-purine-2-carboxamide (Preparation 11) and a mixture of (2S,3R,4R,5R)-4,5-bis(acetyloxy)-2-(3-ethyl-5-isoxazolyl) tetrahydro-3-furanyl acetate and (2S,3R,4R,5S)-4,5-bis (acetyloxy)-2-(3-ethyl-5-isoxazolyl)tetrahydro-3-furanyl acetate (WO-A-9967262).

$^1$H-NMR (400 MHz, CDCl$_3$) δ: 8.50 (1H, br s), 8.00 (1H, br s), 7.35–7.20 (10H, m), 6.45 (1H, br s), 6.00 (1H, br s), 5.90 (1H, br s), 5.30 (1H, m); 4.40–4.30 (3H, m), 3.70–3.60 (2H, m), 2.70 (2H, q), 2.65–2.40 (4H, m), 2.20 (3H, s), 2.05 (3H, s), 1.60–1.30 (6H, m), 1.25 (3H, t).

LRMS (thermospray): m/z [MH$^+$] 751.

Preparation 33

(2R,3R,4R,5R)-4-(Benzoyloxy)-2-(6-[(2,2-diphenylethyl)amino]-2-{[(isobutylsulphonyl)amino]methyl}-9H-purin-9-yl)-5-(1-ethyl-1H-1,2,4-triazol-3-yl)tetrahydro-3-furanyl benzoate

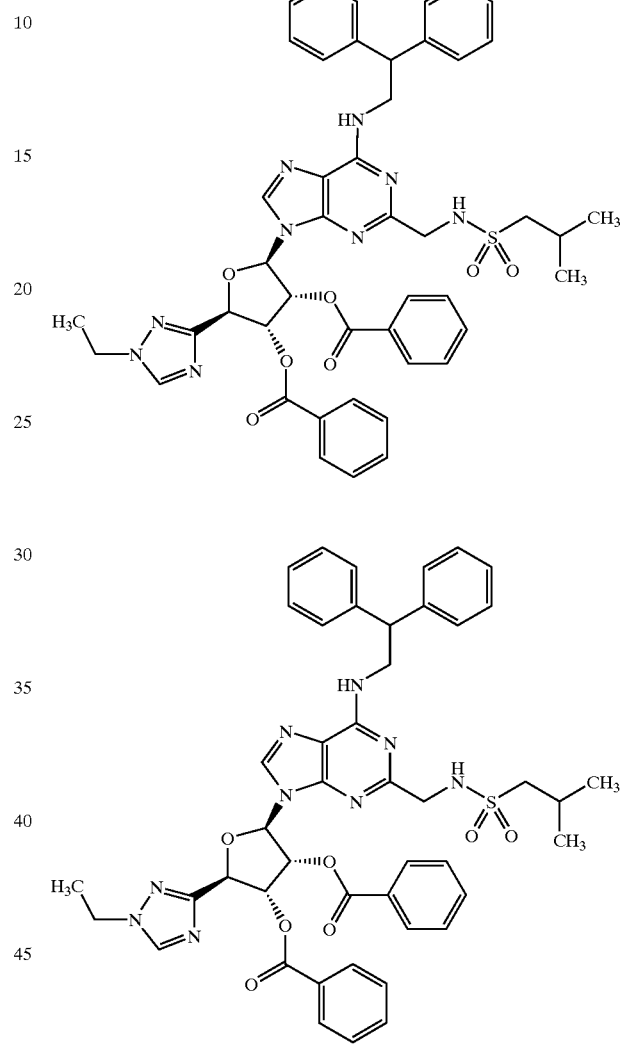

Prepared by the same method as Preparation 26 from N-({6-[(2,2-diphenylethyl)amino]-9H-purin-2-yl}methyl)-2-methyl-1-propanesulphonamide hydrochloride (Preparation 8) and a mixture of (2R,3R,4R,5R)-3,4-bis (benzoyloxy)-5-(1-ethyl-1H-1,2,4-triazol-3-yl)tetrahydro-2-furanyl benzoate and (2S,3R,4R,5R)-3,4-bis(benzoyloxy)-5-(1-ethyl-1H-1,2,4-triazol-3-yl)tetrahydro-2-furanyl benzoate (Preparation 22).

$^1$H-NMR (400 MHz, CDCl$_3$, 3:2 mixture of rotamers) δ: 8.70 (0.4H, s), 8.30 (0.6H, s), 8.20–7.80 (6H, m), 7.65–7.20 (15H, m), 6.90–6.75 (1H, m), 6.65–6.40 (2H, m), 6.20–6.00 (1H, m), 5.65–5.55 (1H, m), 4.60–4.20 (7H, m), 3.05–2.80 (2H, m), 2.20 (1H, m), 1.60–1.50 (3H, m), 1.05–0.80 (6H, m).

LRMS (thermospray): m/z [MH$^+$] 871.

Preparation 34

(2R,3R,4R,5R)-4-(Benzoyloxy)-5-[6-[(2,2-diphenylethyl)amino]-2-({[2-(1-piperidinyl)ethyl]amino}carbonyl)-9H-purin-9-yl]-2-(1-ethyl-1H-1,2,4-triazol-3-yl)tetrahydro-3-furanyl benzoate

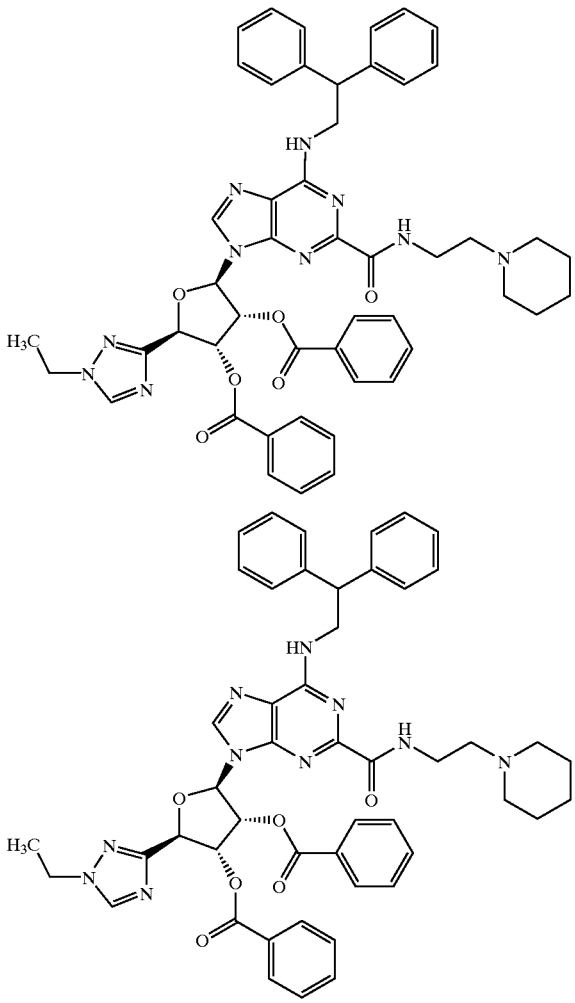

Prepared by the same method as Preparation 27 from 6-[(2,2-diphenylethyl)amino]-N-[2-(1-piperidinyl)ethyl]-9H-purine-2-carboxamide (Preparation 11) and a mixture of (2R,3R,4R,5R)-3,4-bis(benzoyloxy)-5-(1-ethyl-1H-1,2,4-triazol-3-yl)tetrahydro-2-furanyl benzoate and (2S,3R,4R,5R)-3,4-bis(benzoyloxy)-5-(1-ethyl-1H-1,2,4-triazol-3-yl)tetrahydro-2-furanyl benzoate (Preparation 22).

$^1$H-NMR (400 MHz, CDCl$_3$) δ: 8.50–8.30 (1H, m), 8.05–7.90 (7H, m), 7.60–7.10 (14H, m), 6.60–6.50 (2H, m), 6.35 (1H, br s), 5.60 (1H, m), 4.45–4.30 (2H, m); 4.25–4.10 (3H, m), 4.05–3.90 (2H, m), 3.40–3.05 (6H, m), 1.90–1.80 (4H, m), 1.60–1.40 (5H, m).

LRMS (thermospray): m/z [MH$^+$] 876.

Preparation 35

(3aR,4R,6R,6aR)-N'-Hydroxy-6-methoxy-2,2-dimethyltetrahydrofuro[3,4-d][1,3]dioxole-4-carboximidamide

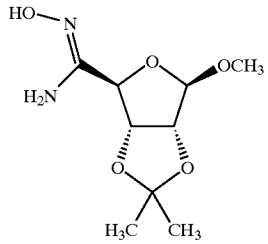

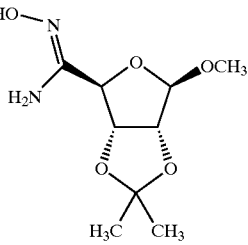

Sodium methoxide (0.4 g, 7.41 mmol) was added to a stirred solution of (3aR,4R,6R,6aR)-6-methoxy-2,2-dimethyltetrahydrofuro[3,4-d][1,3]dioxole-4-carbonitrile (WO-A-9967265) (1.2 g, 6.0 mmol) and hydroxylamine hydrochloride (0.5 g, 7.2 mmol) in methanol (15 ml). The mixture was heated under reflux for one hour and then allowed to cool to room temperature. Water (50 ml) was added and the solution was extracted twice with ethyl acetate (50 ml). The combined extracts were dried (anhydrous magnesium sulphate) and evaporated under reduced pressure. The residue was purified by column chromatography on silica gel eluting with dichloromethane:methanol (98:2 by volume) to give the title compound (0.81 g).

$^1$H-NMR (400 MHz, CDCl$_3$) δ: 6.75 (1H, s), 5.10–5.00 (4H, m), 4.70 (1H, s), 4.60 (1H, d), 3.40 (3H, s), 1.50 (3H, s), 1.30 (3H, s).

LRMS (thermospray): m/z [MH$^+$] 233.

Preparation 36

3-[(3aR,4R,6R,6aR)-6-Methoxy-2,2-dimethyltetrahydrofuro[3,4-d][1,3]dioxol-4-yl]-5-ethyl-1,2,4-oxadiazole

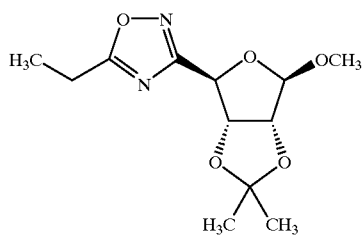

77

-continued

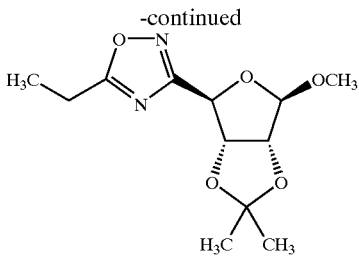

A solution of (3aR,4R,6R,6aR)-N'-hydroxy-6-methoxy-2,2-dimethyl tetrahydrofuro[3,4-d][1,3]dioxole-4-carboximidamide (Preparation 35) (1.1 g, 4.74 mmol), propionic acid (0.39 g, 5.27 mmol) and 1-(3-dimethylaminopropyl)-3-ethylcarbodiimide hydrochloride (1.1 g, 5.74 mmol) in diethylene glycol dimethyl ether (10 ml) was heated under reflux at 60° C. for twelve hours and then heated at 110° C. for a further 3 hours. The solvent was evaporated under reduced pressure and the residue was partitioned between water (50 ml) and a mixture of ether (25 ml) and pentane (25 ml). The organic phase was separated and the aqueous layer was extracted with more ether/pentane mixture (50 ml). The combined organic extracts were dried (anhydrous magnesium sulphate) and the solvent was evaporated under reduced pressure. The residue was purified by column chromatography on silica gel eluting with a gradient system of diethyl ether:pentane (1:2 by volume) gradually changing to diethyl ether:pentane (1:1 by volume) to give the title compound (0.87 g).

$^1$H-NMR (400 MHz, CDCl$_3$) δ: 5.40 (1H, d), 5.20 (1H, s), 5.10 (1H, s), 4.65 (1H, d), 3.20 (3H, s), 2.90 (2H, q), 1.55 (3H, s), 1.40–1.30 (6H, m).

LRMS (thermospray): m/z [MH$^+$] 271.

Preparation 37

(2R,3S,4R,5R)-2-(5-Ethyl-1,2,4-oxadiazol-3-yl)-5-methoxytetrahydro-3,4-furandiol and (2R,3S,4R,5S)-2-(5-ethyl-1,2,4-oxadiazol-3-yl)-5-methoxytetrahydro-3,4-furandiol

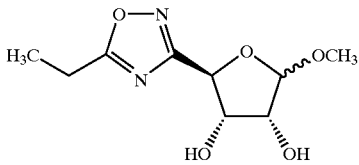

A solution of 3-[(3aR,4R,6R,6aR)-6-methoxy-2,2-dimethyltetrahydrofuro[3,4-d][1,3]dioxol-4-yl]-5-ethyl-1,2,4-oxadiazole (Preparation 36) (0.87 g, 3.22 mmol) in 2 M aqueous hydrochloric acid (7 ml) and methanol (15 ml) was stirred at room temperature for 8 days. Solid sodium hydrogencarbonate was added to neutralise the solution and the solvent was evaporated under reduced pressure. The residue was suspended in methanol (30 ml) and the solvent was again evaporated under reduced pressure. This process was repeated. The resulting solid was slurried in dichloromethane (50 ml), anhydrous magnesium was sulphate added, insoluble solids were filtered off and the filtrate was evaporated under reduced pressure. The title compound, as a 3:1 mixture of anomers, was obtained as an oil (0.68 g).

$^1$H-NMR (400 MHz, CDCl$_3$) δ: 5.15 (1H', d), 5.10 (1H', d), 5.05 (1H, d), 5.00 (1H, s), 4.75 (1H, m), 4.40 (1H', m), 4.30 (1H', m), 4.20 (1H, m), 3.55 (3H', s), 3.40 (3H, s), 3.00–2.90 (2H+4H', m), 2.75 (1H, d), 2.70 (1H, m), 1.40 (3H+3H', m).

LRMS (thermospray): m/z [MH$^+$] 231.

78

Preparation 38

(2R,3R,4R,5S)-4,5-bis(Acetoxy)-2-(5-ethyl-1,2,4-oxadiazol-3-yl)tetrahydro-3-furanyl acetate

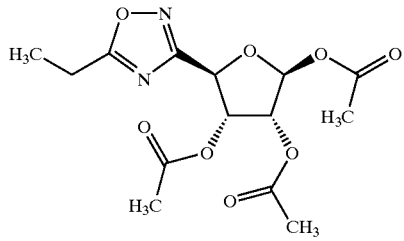

Acetic acid (1.0 ml, 17.5 mmol), acetic anhydride (1.65 ml, 17.5 mmol) and concentrated sulphuric acid (1 drop) were added to a solution of (2R,3S,4R,5R)-2-(5-ethyl-1,2,4-oxadiazol-3-yl)-5-methoxytetrahydro-3,4-furandiol and (2R,3S,4R,5S)-2-(5-ethyl-1,2,4-oxadiazol-3-yl)-5-methoxytetrahydro-3,4-furandiol (Preparation 37) (0.675 g, 2.93 mmol) in dichloromethane (15 ml) and the solution was heated under reflux for 12 hours. The cooled reaction mixture was then diluted with diethyl ether (30 ml) and water (20 ml). Solid sodium hydrogencarbonate was added to neutralise the solution and the organic layer was separated. The aqueous layer was extracted with more diethyl ether (50 ml) and the combined organic extracts were dried (anhydrous magnesium sulphate) and evaporated under reduced pressure. The semi-crystalline residue was triturated with a mixture of diethyl ether and pentane and the solid was filtered off and dried (0.56 g).

$^1$H-NMR (400 MHz, CDCl$_3$) δ: 6.25 (1H, s), 5.80 (1H, dd), 5.50 (1H, d), 5.25 (1H, d), 2.90 (2H, q), 2.15 (3H, s), 2.10 (3H, s), 2.05 (3H, s), 1.40 (3H, t).

LRMS (thermospray): m/z [MH$^+$] 343.

Preparation 39

(2R,3R,4R,5R)-4-(Acetyloxy)-2-(6-[(2,2-diphenylethyl)amino]-2-{[[(isobutylsulphonyl)amino]methyl}9H-purin-9-yl)-5-(5-ethyl-1,2,4-oxadiazol-3-yl)tetrahydro-3-furanyl acetate

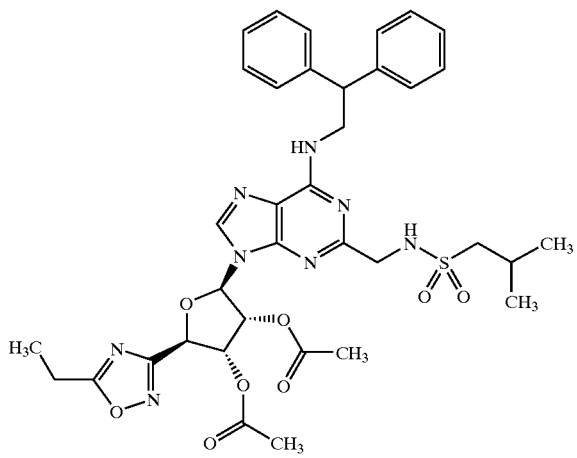

Prepared by the same method as Preparation 26 from N-({6-[(2,2-diphenylethyl)amino]-9H-purin-2-yl}methyl)-2-methyl-1-propanesulphonamide hydrochloride (Preparation 8) and (2R,3R,4R,5S)-4,5-bis(acetoxy)-2-(5-ethyl-1,2,4-oxadiazol-3-yl)tetrahydro-3-furanyl acetate (Preparation 38).

$^1$H-NMR (400 MHz, CDCl$_3$) δ: 8.20 (1H, s), 7.35–7.20 (10H, m), 6.30 (1H, d), 6.15 (1H, m), 5.90 (1H, m), 5.80 (1H, br s), 5.75 (1H, br s); 5.40 (1H, d), 4.45–4.20 (5H, m), 3.00–2.90 (4H, m), 2.30 (1H, m), 2.20 (3H, s), 2.10 (3H, s), 1.40 (3H, t), 1.05 (6H, d).

LRMS (thermospray): m/z [MH$^+$] 747.

Preparation 40

(2R,3R,4R,5R)-4-(Benzoyloxy)-5-(6-[(2,2-diphenylethyl)amino]-2-{[(isobutylsulphonyl)amino]methyl}-9H-purin-9-yl)-2-(1-ethyl-1H-1,2,3-triazol-4-yl)tetrahydro-3-furanyl benzoate

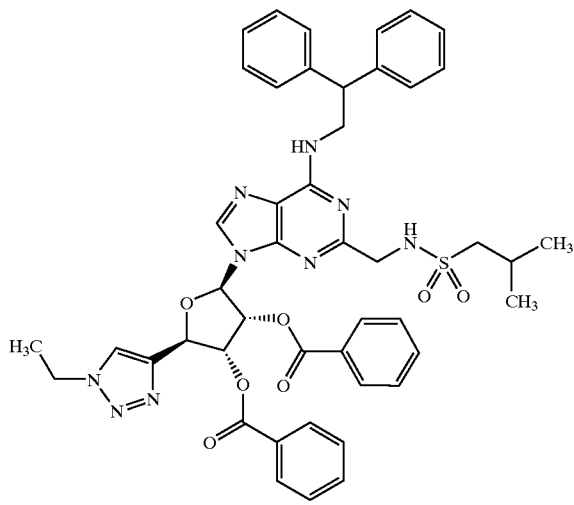

Prepared by the same method as Preparation 26 from N-({6-[(2,2-diphenylethyl)amino]-9H-purin-2-yl}methyl)-2-methyl-1-propanesulphonamide hydrochloride (Preparation 8) and (2S,3R,4R, 5R)-3,4-bis(benzoyloxy)-5-(1-ethyl-1H-1,2,3-triazol-4-yl)tetrahydro-2-furanyl benzoate (Preparation 25).

$^1$H-NMR (400 MHz, CDCl$_3$) δ: 8.05 (1H, s), 8.00 (4H, m), 7.90 (1H, br s), 7.60–7.50 (2H, m), 7.35–7.20 (15H, m), 6.90 (1H, m), 6.50 (1H, m), 6.25 (1H, s), 6.20 (1H, br s), 5.80 (1H, br s), 5.75 (1H, d), 5.60 (1H, br s), 5.50–5.20 (5H, m); 3.00 (2H, m), 2.30 (1H, m), 1.50 (3H, t), 1.05 (6H, d).

Preparation 41
N-({6-[(2,2-Diphenylethyl)amino]-9-tetrahydro-2H-pyran-2-yl-9H-purin-2-yl}methyl)-N'-[2-(1-piperidinyl)ethyl]urea

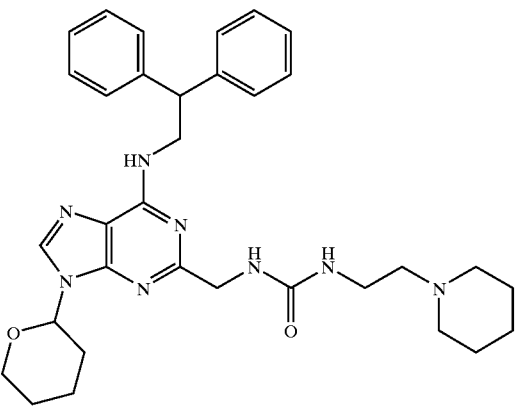

2-(1-Piperidinyl)ethanamine (0.35 ml, 2.46 mmol) was added to a solution of N,N'-carbonyldiimidazole (420 mg, 2.6 mmol) in dichloromethane (100 ml). The reaction mixture was stirred for ten minutes at room temperature and then 2-(aminomethyl)-N-(2,2-diphenylethyl)-9-tetrahydro-2H-pyran-2-yl-9H-purin-6-amine (1.0 g, 2.33 mmol) (Preparation 6) was added. The reaction mixture was stirred for 3 hours at room temperature. Dichloromethane (50 ml) was added and the resulting solution was washed with water (50 ml) and saturated aqueous sodium chloride solution (50 ml). The organic layer was dried (anhydrous MgSO$_4$) and the solvent was removed under reduced pressure. The residue was purified by column chromatography on silica gel eluting with dichloromethane:methanol:0.88 concentrated aqueous ammonia (93:71:1 by volume). This gave the title compound as an oil (300 mg).

$^1$H-NMR (400 MHz, CDCl$_3$) δ: 7.85 (1H, s), 7.55 (1H, s), 7.30–7.05 (10H, m), 5.70–5.60 (1H, m), 4.50–4.00 (6H, m), 3.75–3.60 (1H, m), 3.30–3.10 (2H, m), 2.45–2.20 (6H, m), 2.05–1.85 (2H, m), 1.85–1.25 (10H, m).

LRMS (thermospray): m/z [MH$^+$] 583.

Preparation 42
N-({6-[(2,2-Diphenylethyl)amino]-9H-purin-2-yl}methyl)-N'-[2-(1-piperidinyl)ethyl]urea

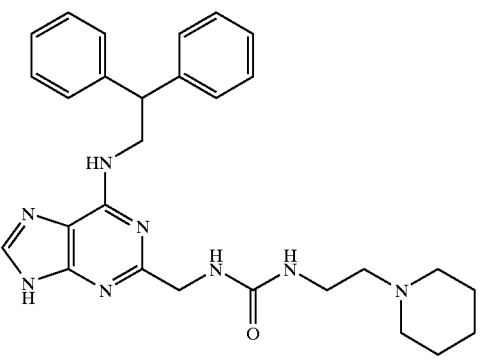

A solution of N-({6-[(2,2-diphenylethyl)amino]-9-tetrahydro-2H-pyran-2-yl-9H-purin-2-yl}methyl)-N'-[2-(1-piperidinyl)ethyl]urea (300 mg, 0.51 mmol) (Preparation 41) in methanol (150 ml) was treated with 2 molar aqueous hydrochloric acid (100 ml). The reaction mixture was stirred at room temperature for 2 hours. The solvent volume was then reduced to 100 ml by evaporation under reduced pressure. Saturated aqueous sodium hydrogen carbonate (50 ml) and ethyl acetate (200 ml) were added. The two phases were separated. The organic layer was washed with saturated aqueous sodium chloride solution (100 ml), dried (anhydrous MgSO$_4$) and evaporated to give the title compound as a white solid (255 mg).

$^1$H-NMR (400 MHz, CDCl$_3$) δ: 7.80 (1H, s), 7.35–7.10 (10H, m), 4.55–4.10 (5H, m), 3.40–3.20 (2H, m), 2.60–2.30 (6H, m), 1.60–1.25 (6H, m).

LRMS (thermospray): m/z [MH$^+$] 499.

Preparation 43

N-{2-[Cyclopentyl(isopropyl)amino]ethyl}-N'-({6-[(2,2-diphenylethyl)amino]-9-tetrahydro-2H-pyran-2-yl-9H-purin-2-yl}methyl)urea

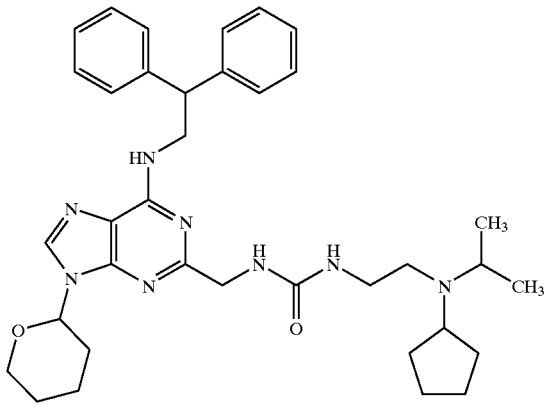

Prepared from N$^1$-Cyclopentyl-N$^1$-isopropyl-1,2-ethanediamine (Preparation 49) and 2-(aminomethyl)-N-(2,2-diphenylethyl)-9-tetrahydro-2H-pyran-2-yl-9H-purin-6-amine (Preparation 6) by a similar method to Preparation 41. The title compound was obtained as an oil.

$^1$H-NMR (400 MHz, CDCl$_3$) δ: 8.10 (1H, s), 7.30–7.10 (10H, m), 5.65 (1H, d), 4.50–4.20 (4H, m), 4.10–4.00 (2H, m), 3.75 (1H, m), 3.15–3.00 (4H, m), 2.55–2.45 (2H, m), 2.10–1.90 (2H, m), 1.80–1.10 (14H, m), 1.00 (6H, d).

LRMS (thermospray): m/z [MH$^+$] 626.

Preparation 44

N-{2-[Cyclopentyl(isopropyl)amino]ethyl}-N'-({6-[(2,2-diphenylethyl)amino]-9H-purin-2-yl}methyl)urea

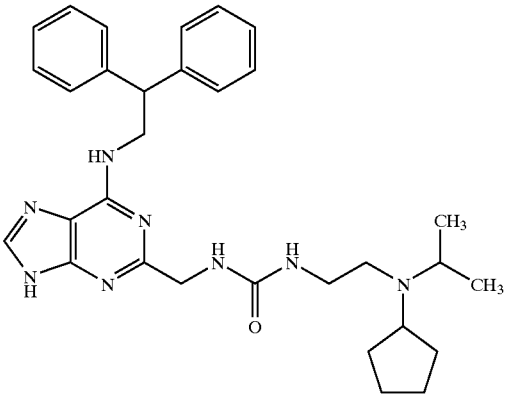

Prepared from N-{2-[cyclopentyl(isopropyl)amino]ethyl}-N'-({6-[(2,2-diphenyl-ethyl)amino]-9-tetrahydro-2H-pyran-2-yl-9H-purin-2-yl}methyl)urea (Preparation 43) by a similar method to Preparation 42. The title compound was obtained as a white solid.

$^1$H-NMR (400 MHz, CDCl$_3$) δ: 7.90 (1H, s), 7.30–7.25 (8H, m), 7.20–7.10 (2H, m), 4.45 (1H, m), 4.35 (2H, s), 4.25 (1H, m), 3.15 (2H, m), 2.60 (2H, m), 1.80 (2H, m), 1.60–1.35 (6H, m), 1.25 (2H, s), 1.00 (6H, d).

LRMS (thermospray): m/z [MH$^+$] 541.

Preparation 45

(2R,3R,4R,5R)-4-(Acetoxy)-2-{2-({[({2-[cyclopentyl(isopropyl)-amino]ethyl}amino)carbonyl]amino}methyl)-6-[(2,2-diphenylethyl)amino]-9H-purin-9-yl}-5-(2-ethyl-2H-tetrazol-5-yl)tetrahydro-3-furanyl acetate

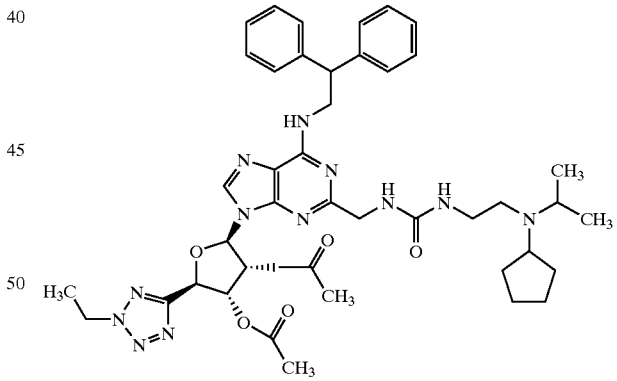

Prepared from N-{2-[cyclopentyl(isopropyl)amino]ethyl}-N'-({6-[(2,2-diphenyl-ethyl)amino]-9H-purin-2-yl}methyl)urea (Preparation 44) and (2R,3R,4R)-4,5-bis(acetoxy)-2-(2-ethyl-2H-tetrazol-5-yl)tetrahydro-3-furanyl acetate (WO 9967265) by a similar procedure to Preparation 26. The title compound was obtained as a white solid.

$^1$H-NMR (400 MHz, CDCl$_3$) δ: 8.05 (1H, s), 7.30–7.20 (10H, m), 6.25 (1H, m), 6.20 (1H, m), 5.90 (1H, m), 5.40 (1H, m), 5.25 (1H, m), 4.60 (2H, m), 4.40 (2H, m); 4.25 (2H, m), 3.30 (2H, m), 3.10–2.90 (2H, m), 2.15–2.00 (9H, m), 1.80–1.20 (9H, m), 0.90 (6H, m).

LRMS (thermospray): m/z [MH$^+$] 824.

Preparation 46

(2R,3R,4R,5R)-4-(Acetoxy)-2-(6-[(2,2-diphenylethyl)amino]-2-{[({[2-(1-piperidinyl)ethyl]amino}carbonyl)amino]methyl}-9H-purin-9-yl)-5-(2-ethyl-2H-tetrazol-5-yl)tetrahydro-3-furanyl acetate

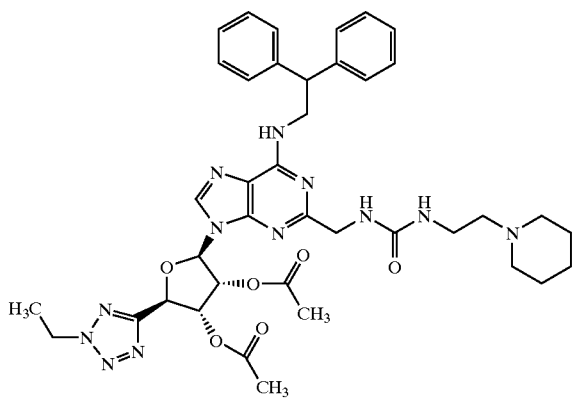

Prepared from N-({6-[(2,2-diphenylethyl)amino]-9H-purin-2-yl}methyl)-N'-[2-(1-piperidinyl)ethyl]urea (Preparation 42) and (2R,3R,4R)-4,5-bis(acetoxy)-2-(2-ethyl-2H-tetrazol-5-yl)tetrahydro-3-furanyl acetate (WO 9967265) by a similar procedure to Preparation 26. The title compound was obtained as a white solid.

$^1$H-NMR (400 MHz, CDCl$_3$) δ: 8.15 (1H, m), 7.30–7.05 (10H, m), 6.40 (1H, m), 6.30–6.15 (2H, m), 5.50 (1H, m), 4.60 (2H, m), 4.50–4.30 (3H, m), 4.20 (2H, m), 2.40 (6H, m), 2.15–2.00 (9H, m), 1.60–1.30 (10H, m).

LRMS (thermospray): m/z [MH$^+$] 782.

Preparation 47

N-Isopropylcyclopentanamine

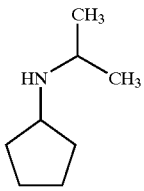

Pearlman's catalyst (20% w/w palladium hydroxide-on-carbon) (1.5 g) was added to a solution of cyclopentylamine (15 ml, 0.21 mol) in acetone (200 ml). The reaction mixture was stirred under an atmosphere of hydrogen gas at 414 kPa (60 psi). After stirring for 16 hours the reaction mixture was filtered through Arbocel (trade mark) and the solvent was removed under reduced pressure to give the title compound (15 ml) as a thin oil.

$^1$H-NMR (400 MHz, CDCl$_3$) δ: 3.20–3.10 (1H, m), 2.90–2.80 (1H, m), 1.95–1.85 (2H, m), 1.75–1.45 (4H, m), 1.35–1.20 (2H, m), 1.10–1.00 (6H, m).

Preparation 48

[Cyclopentyl(isopropyl)amino]acetonitrile

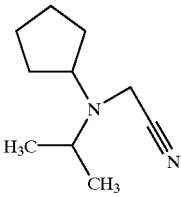

Hydroxyacetonitrile (8.2 ml of a 70% w/w solution in water, 0.1 mol) was added to a solution of N-isopropylcyclopentanamine (11.43 g, 0.09 mol) (Preparation 47) in ethanol (60 ml). The reaction mixture was heated under reflux for 3 hours, allowed to cool and evaporated under reduced pressure. The residue was purified by chromatography on silica gel eluting with dichloromethane:methanol (98:2, by volume) to give the title compound (14.1 g) as a clear oil.

$^1$H-NMR (400 MHz, CDCl$_3$) δ: 3.60–3.50 (2H, s), 3.30–3.20 (2H, m), 2.00–1.85 (2H, m), 1.80–1.55 (4H, m), 1.45–1.30 (2H, m), 1.15–1.05 (6H, m).

Preparation 49

N$^1$-Cyclopentyl-N$^1$-isopropyl-1,2-ethanediamine

Lithium aluminium hydride (66 ml of a 1 molar solution in tetrahydrofuran, 0.066 mol) was added to a stirred solution of [cyclopentyl(isopropyl)amino]-acetonitrile (10 g, 0.66 mol) (Preparation 48) in tetrahydrofuran (100 ml) at 0° C. The reaction mixture was stirred at 0° C. for 20 minutes and then heated under reflux for 2 hours. The reaction mixture was allowed to cool to room temperature and left to stand overnight. The reaction mixture was cooled in an icebath and treated dropwise with 4.8 ml of a 7.5% w/w aqueous sodium hydroxide solution and then 7.4 ml of water. The solvent was removed under reduced pressure and the residue was slurried with diethyl ether (200 ml) for 30 minutes and then filtered. The filtrate was evaporated under reduced pressure to give the title compound as a colourless oil (10.30 g).

$^1$H-NMR (400 MHz, CDCl$_3$) δ: 3.10–2.95 (2H, m), 2.70–2.60 (2H, m), 2.50–2.40 (2H, m), 1.80–1.45 (10H, m), 1.05–0.95 (6H, m).

LRMS (thermospray): m/z [MH$^+$] 171.

Pharmacological Activity

All the compounds of the Examples were tested for anti-inflammatory activity by their ability to inhibit neutrophil function (which indicates A2a receptor agonist activity) by the method described on page 52 and all had an IC$_{50}$ of less than 250 nanomolar.

What is claimed is:
1. A compound of the formula

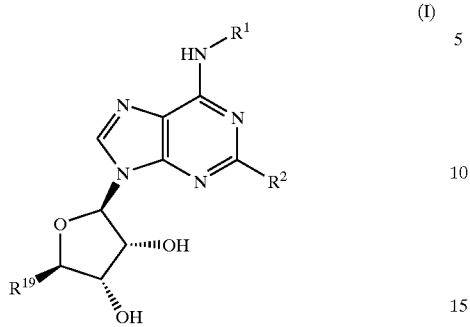

or a pharmaceutically acceptable salt thereof, wherein
$R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;
$R^2$ is either
(a) —$CH_2NHSO_2$—A—$R_3$ wherein
A is a bond or $C_1$–$C_3$ alkylene; and
$R_3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, $NR^4R^4$, —$SO_2NR^4R^4$, —$CONR^4R^4$, —$NR^4COR^5$ or —$NR^4SO_2R^5$, with the proviso that $R^3$ is not H when A is a bond, or (ii) when A is $C_2$–$C_3$ alkylene, —$NR^8R^9$, —$OR^4$, —$COOR^4$, —$OCOR^5$, —$SO_2R^5$, —CN, —$SO_2NR^4R^4$, —$NR^4COR^5$ or —$CONR^4R^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^6$, —$SO_2R^7$, —$SO_2NR^6R^6$ or —$CONR^6R^6$; or
(b) —$CONR^{10}$—$A^1$—$R^{11}$ wherein
$A^1$ is a bond or $C_1$–$C_6$ alkylene;
$R^{10}$ is H or $C_1$–$C_6$ alkyl; and
$R^{11}$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^{11}$ is not H when $A^1$ is a bond, or (ii) when $A^1$ is $C_2$–$C_6$ alkylene, —$NR^4R^4$, —$OR^4$, —$OCOR^5$, —$SO_2R^5$, —$SO_2NR^4R^4$, —$NR^4SO_2R^5$ or —$NR^4COR^5$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^7$, —$SO_2R^7$, —$SO_2NR^6R^6$ or —$CONR^6R^6$, or (iv) when $A^1$ is $C_2$–$C_6$ alkylene, N-linked azetidinyl, pyrrolidinyl, piperidinyl, morpholinyl, piperazinyl, homopiperazinyl, homopiperidinyl or tetrahydroquinolinyl, each being optionally C-substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$ and said piperazinyl and homopiperazinyl being optionally substituted on the nitrogen not attached to $A^1$ by $C_1$–$C_6$ alkyl, phenyl, $C_1$–$C_6$ alkoxy-($C_2$–$C_6$)-alkyl, $R^4R^4N$—($C_2$–$C_6$)-alkyl, halo-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or (v) when $A^1$ is $C_1$–$C_6$ alkylene, —$COOR^4$, —CN or —$CONR^4R^4$; or
(c) —X—$NR^{12a}$—Y—$NR^{13}R^{14}$ wherein
X is —$CH_2$— or —$CH_2CH_2$—; and
$R^{12a}$ is H or $C_1$–$C_6$ alkyl; or
(d) —CO—$NR^{18}$—$X^1$—$NR^{12}$—Y—$NR^{13}R^{14}$ wherein
(i) $X^1$ is (1) unbranched $C_2$–$C_3$ alkylene optionally substituted by $C_1$–$C_6$ alkyl or $C_3$–$C_8$ cycloalkyl or (2) a group of the formula —$(CH_2)_n$—W—$(CH_2)_p$— wherein W is $C_5$–$C_7$ cycloalkylene, n is 0 or 1 and p is 0 or 1;
$R^{18}$ is H or $C_1$–$C_6$ alkyl; and
$R^{12}$ is H or $C_1$–$C_6$ alkyl; or
(ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and
$R^{18}$ is H or $C_1$–$C_6$ alkyl; or
(iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and
$R^{12}$ is H or $C_1$–$C_6$ alkyl;
Y is CO, CS, $SO_2$ or C=N(CN);
$R^4$ is H, $C_1$–$C_6$ alkyl, $C_3$–$C_8$ cycloalkyl or phenyl;
$R^5$ is $C_1$–$C_6$ alkyl, $C_3$–$C_8$ cycloalkyl or phenyl;
$R^6$ is H, $C_1$–$C_6$ alkyl, $C_3$–$C_8$ cycloalkyl, phenyl, naphthyl or het;
$R^7$ is $C_1$–$C_6$ alkyl, $C_3$–$C_8$ cycloalkyl, phenyl, naphthyl or het;
either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^{15}R^{16}$ or —$OR^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het$^1$, or (2) —($C_2$–$C_6$ alkylene)-$NR^8R^9$, or (3) —($C_1$–$C_6$ alkylene)-$R^{17}$, or (4) $C_1$–$C_6$ alkyl or $C_3$–$C_8$ cycloalkyl;

$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^{17}$ is (i) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{24}R^{24}$, —$CONR^{24}R^{24}$ or —($C_1$—$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het$^1$;

m is 0, 1 or 2;

het, used in the definitions of $R^6$ and $R^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

het$^1$, used in the definition of $R^{14}$ and $R^{17}$, is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$;

$R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and $R^{24}$ is H or $C_1$–$C_6$ alkyl optionally substituted by cyclopropyl.

2. A method of treating adult respiratory distress syndrome (ARDS), bronchitis, chronic bronchitis, chronic obstructive pulmonary disease (COPD), cystic fibrosis, asthma, emphysema, bronchiectasis, chronic sinusitis or rhinitis in a mammal, said method comprising administering to said mammal in need of such treatment an effective amount of a compound of claim 1 or a pharmaceutically acceptable salt thereof.

3. A method of claim 2 wherein said disease is asthma.

4. A method of claim 2 wherein said disease is chronic obstructive pulmonary disease.

5. A method of claim 2 wherein said disease is bronchitis or chronic bronchitis.

6. A method of claim 2 wherein said disease is bronchiectasis.

7. A method of claim 2 wherein said disease is rhinitis.

8. A method of claim 2 wherein said mammal is a human.

9. A process for preparing a compound of the formula (I), as defined in claim 1, wherein $R^2$ is —X—$NR^{12a}$—Y—$NR^{13}R^{14}$ is —($C_1$–$C_6$ alkylene)-$NR^8R^9$, and $R^9$ is —$CONR^4R^4$, —$COOR^5$, $COR^5$, $SO_2R^5$ or —$SO_2NR^4R^4$, or a pharmaceutically acceptable salt thereof, comprising reacting a compound of the formula (LXXXIV)

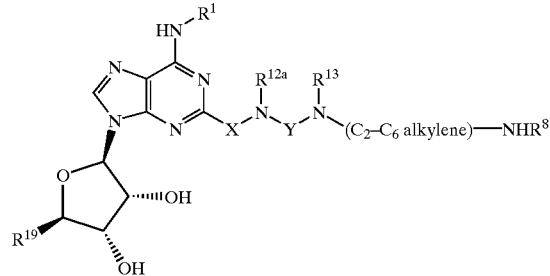

wherein:

$R^1$ is (i) H, (ii) $C_2$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

X is —$CH_2$— or —$CH_2CH_2$—; and $R^{12a}$ is H or $C_1$–$C_6$ alkyl;

Y is CO, CS, $SO_2$ or C=N(CN);

$R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl;

$R^8$ is H, $C_1$–$C_6$ alkyl, $C_3$–$C_8$ cycloalkyl, phenyl or benzyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

with a suitable acylating or sulphonylating agent;

said process being optionally followed by the conversion of the compound of the formula (I) to a pharmaceutically acceptable salt thereof.

10. A process for preparing a compound of the formula (I), as defined in claim 1, wherein $R^2$ is —CO—$NR^{18}$—$X^1$—$NR^{12}$—Y—$NR^{13}R^{14}$, $R^{14}$ is —($C_2$–$C_6$ alkylene)-$NR^8R^9$, and $R^9$ is —$CONR^4R^4$, —$COOR^5$, $COR^5$, $SO_2R^5$ or —$SO_2NR^4R^4$, or a pharmaceutically acceptable salt thereof, comprising reacting a compound of the formula (LXXXV)

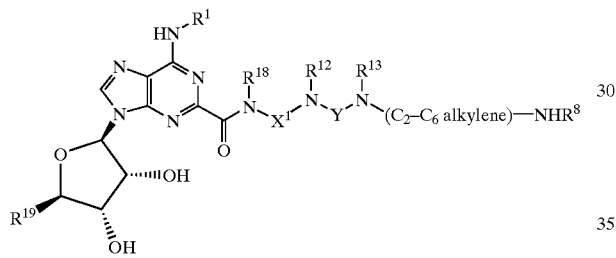

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

(i) $X^1$ is (1) unbranched $C_2$–$C_3$ alkylene optionally substituted $C_1$–$C_6$ alkyl or $C_3$–$C_8$ cycloalkyl or (2) a group of the formula —($CH_2$)$_n$—W—($CH_2$)$_p$— wherein W is $C_5$–$C_7$ cycloalkylene, n is 0 or 1 and p is 0 or 1;

$R^{18}$ is H or $C_1$–$C_6$ alkyl; and $R^{12}$ is H or $C_1$–$C_6$ alkyl; or (ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{18}$ is H or $C_1$–$C_6$ alkyl; or (iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{12}$ is H or $C_1$–$C_6$ alkyl;

Y is CO, CS, $SO_2$ or C=N(CN);

$R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl;

$R^8$ is H, $C_1$–$C_6$ alkyl, $C_3$–$C_8$ cycloalkyl, phenyl or benzyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

with a suitable acylating or sulphonylating agent; said process being optionally followed by the conversion of the compound of the formula (I) to a pharmaceutically acceptable salt thereof.

11. A compound of the formula (II)

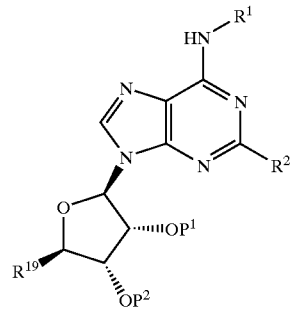

wherein either $P^1$ and $P^2$ when taken separately, are protecting groups or, $P^1$ and $P^2$, when taken together are a protecting group; or (XXXII)

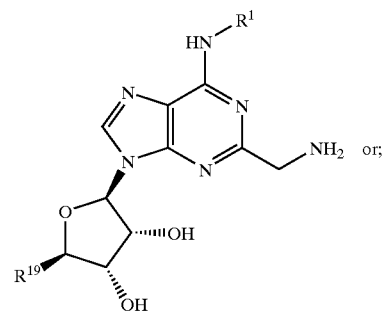

(XXXIIA)

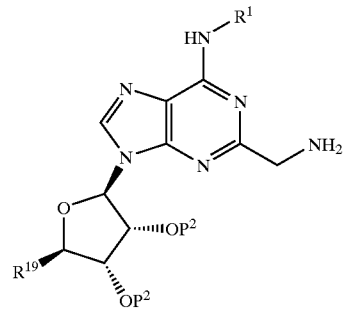

wherein either P¹ and P², when taken separately, are protecting groups or, P¹ and P², when taken together are a protecting group; or

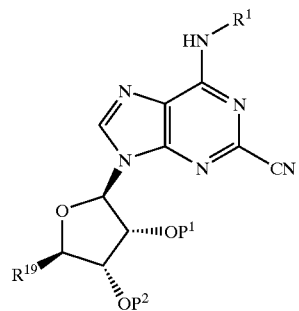
(XXXIII)

wherein either P¹ and P², when taken separately, are protecting groups or, P¹ and P², when taken together are a protecting group; or

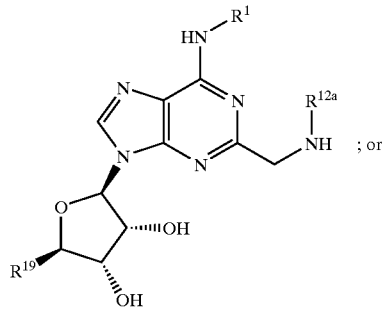
(XXXV)

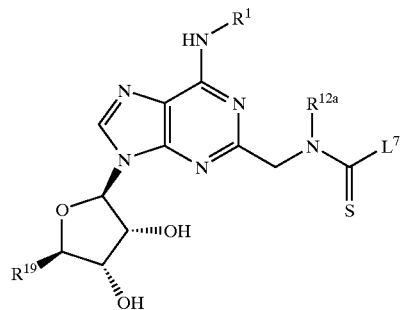
(XXXVI)

wherein $L^7$ is a suitable leaving group; or

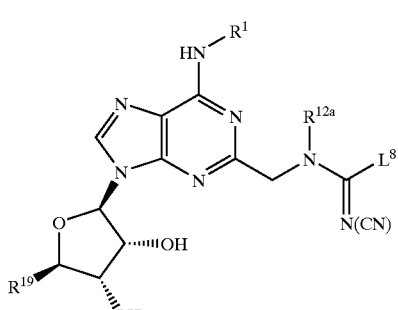
(XXXVII)

wherein $L^8$ is a suitable leaving group; or

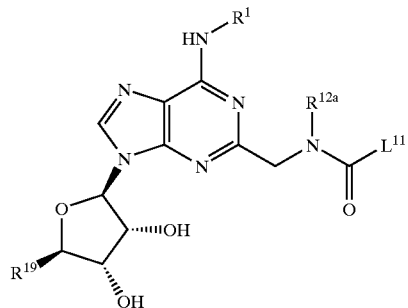
(XXXIX)

wherein $L^{11}$ is a suitable leaving group; or

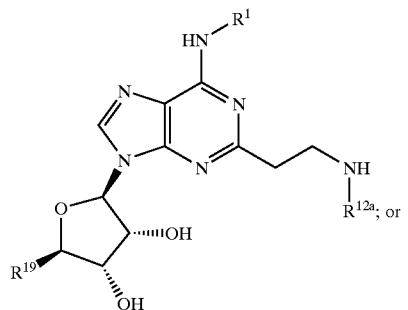
(XXXXII)

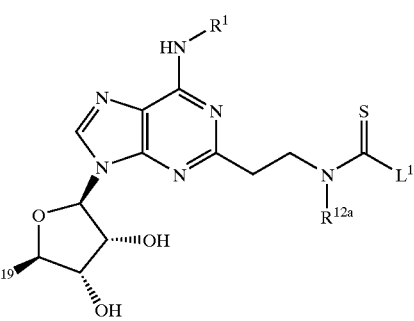
(XXXXIII)

wherein $L^{14}$ is a suitable leaving group; or

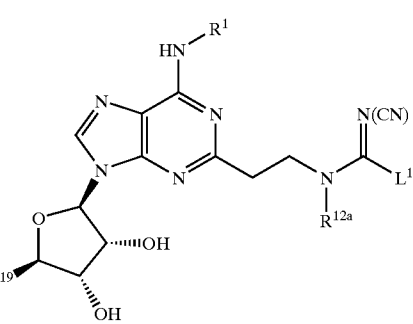
(XXXXIV)

wherein $L^{15}$ is a suitable leaving group; or

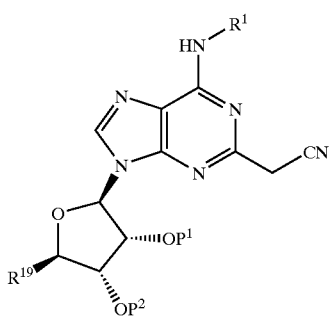

(XXXXVI)

wherein either $P^1$ and $P^2$, when taken separately, are protecting groups or, $P^1$ and $P^2$, when taken together are a protecting group; or

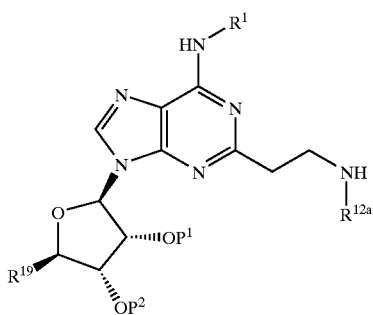

(XXXXV)

wherein either $P^1$ and $P^2$, when taken separately, are protecting groups or, $P^1$ and $P^2$, when taken together are a protecting group; or

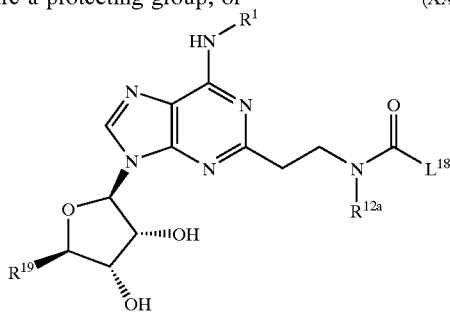

(XXXXVIII)

wherein $L^{18}$ is a suitable leaving group; or

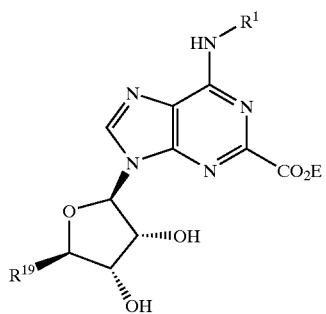

(LI)

wherein E is $C_1$–$C_6$ alkyl; or

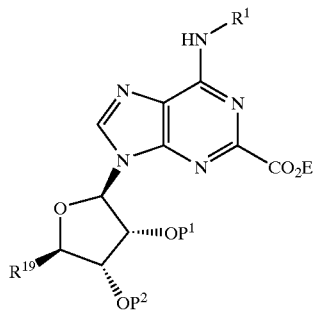

(LII)

wherein either $P^1$ and $P^2$ are protecting groups or, $P^1$ and $P^2$, when taken together are a protecting group, and E is $C_1$–$C_6$ alkyl; or

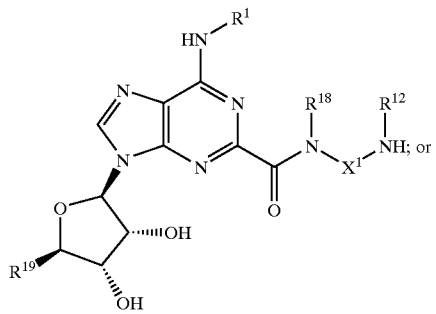

(LIX)

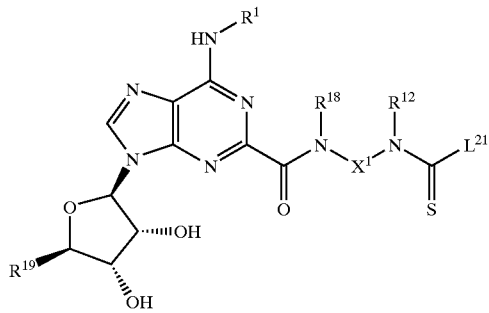

(LX)

wherein $L^{21}$ is a suitable leaving group; or

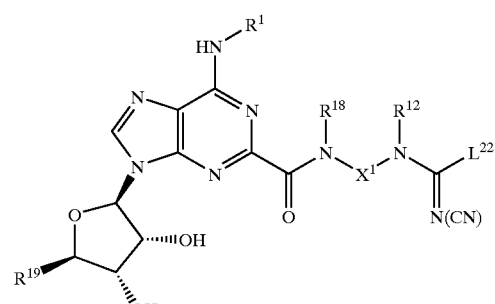

(LXI)

wherein $L^{22}$ is a suitable leaving group; or

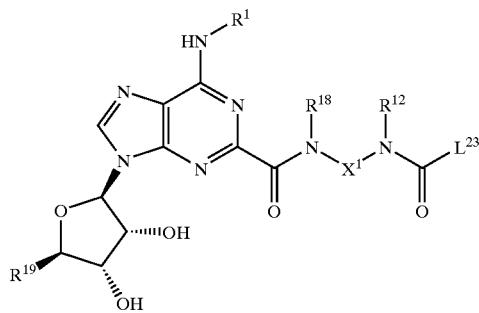

(LXII)

wherein $L^{23}$ is a suitable leaving group; or

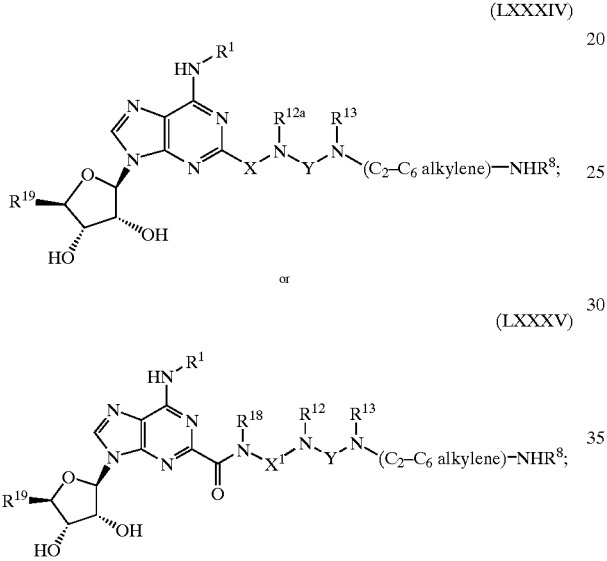

(LXXXIV)

or (LXXXV)

wherein:
- $R^1$ is independently (i) H, (ii) $C_1$–$C_6$ alkyl optionally substituted by 1 or 2 substituents each independently selected from fluorenyl, phenyl, and naphthyl, said phenyl, naphthyl and fluorenyl being optionally substituted by $C_1$–$C_6$ alkyl, $C_1$–$C_6$ alkoxy, halo or cyano, or (iii) fluorenyl;
- $R^2$ is either
  (a) —CH$_2$NHSO$_2$—A—$R^3$ wherein
  A is a bond or $C_1$–$C_3$ alkylene; and
  $R^3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4$N—($C_1$–$C_6$)-alkyl, halo-($C_1$–$C_6$)-alkyl, fluoro-($C_1$–$C_6$)-alkoxy, $C_2$–$C_5$ alkanoyl, halo, —OR$^4$, cyano, —COOR$^4$, $C_3$–$C_8$ cycloalkyl, —S(O)$_m$R$^5$, —NR$^4$R$^4$, —SO$_2$NR$^4$R$^4$, —CONR$^4$R$^4$, —NR$^4$COR$^5$ or —NR$^4$SO$_2$R$^5$, with the proviso that $R^3$ is not H when A is a bond, or (ii) when A is $C_2$–$C_3$ alkylene, —NR$^8$R$^9$, —OR$^4$, —COOR$^4$, —OCOR$^5$, —SO$_2$R$^5$, —CN, —SO$_2$NR$^4$R$^4$, —NR$^4$COR$^5$ or —CONR$^4$R$^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6$N—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —OR$^6$, $R^7$, —COR$^6$, —NR$^6$R$^6$, —COOR$^6$, —S(O)$_m$R$^7$, —SO$_2$NR$^6$R$^6$, —CONR$^6$R$^6$, —NR$^6$SO$_2$R$^7$, —NR$^6$COR$^7$ or —NR$^6$COR$^7$ and optionally N-substituted by $C_1$–$C_6$ alkoxy-($C_1$–$C_6$)-alkyl, $R^6R^6$N—($C_2$–$C_6$)-alkyl, halo-($C_1$–$C_6$)-alkyl, fluoro-($C_2$–$C_5$)-alkanoyl, $R^7$, —COR$^6$, —COOR$^6$, —S(O)$_m$R$^7$, —SO$_2$NR$^6$R$^6$ or —CONR$^6$R$^6$; or
  (b) —CONR$^{10}$—A$^1$—R$^{11}$ wherein
  $A^1$ is a bond or $C_1$–$C_6$ alkylene;
  $R^{10}$ is H or $C_1$–$C_6$ alkyl; and
  $R^{11}$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_5$)-alkyl, $R^4R^4$N—($C_1$–$C_6$)-alkyl, halo-($C_1$–$C_6$)-alkyl, fluoro-($C_1$–$C_6$)-alkoxy, $C_2$–$C_5$ alkanoyl, halo, —OR$^4$, cyano —COOR$^4$, $C_3$–$C_8$ cycloalkyl, —S(O)$_m$R$^5$, —NR$^4$R$^4$, —SO$_2$NR$^4$R$^4$, —CONR$^4$R$^4$, —NR$^4$COR$^5$ or —NR$^4$SO$_2$R$^5$, with the proviso that $R^{11}$ is not H when $A^1$ is a bond, or (ii) when $A^1$ is $C_2$–$C_6$ alkylene, —NR$^4$R$^4$, —OR$^4$, —OCOR$^5$, —SO$_2$R$^5$, —SO$_2$NR$^4$R$^4$, —NR$^4$SO$_2$R$^5$ or —NR$^4$COR$^5$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6$N—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —OR$^6$, $R^7$, —COR$^6$, —NR$^6$R$^6$, —COOR$^6$, —S(O)$_m$R$^7$, —SO$_2$NR$^6$R$^6$, —CONR$^6$R$^6$, —NR$^6$SO$_2$R$^7$ or —NR$^6$COR$^7$ and optionally N-substituted by $C_1$–$C_6$ alkoxy-($C_1$–$C_6$)-alkyl, $R^6R^6$N—($C_2$–$C_6$)-alkyl, halo-($C_1$–$C_6$)-alkyl, fluoro-($C_2$–$C_5$)-alkanoyl, $R^7$, —COR$^6$, —COOR$^7$, —SO$_2$R$^7$, —SO$_2$NR$^6$R$^6$ or —CONR$^6$R$^6$, or (iv) when $A^1$ is $C_2$–$C_6$ alkylene, N-linked azetidinyl, pyrrolidinyl, piperidinyl, morpholinyl, piperazinyl, homopiperazinyl, homopiperidinyl or tetrahydroquinolinyl, each being optionally C-substituted by $C_1$–$C_6$ alkyl, phenyl, $C_1$–$C_6$ alkoxy-($C_1$–$C_6$)-alkyl, $R^4R^4$N—($C_1$–$C_6$)-alkyl, halo-($C_1$–$C_6$)-alkyl, fluoro-($C_1$–$C_6$)-alkoxy, $C_2$–$C_5$ alkanoyl, halo, —OR$^4$, cyano, —COOR$^4$, $C_3$–$C_8$ cycloalkyl, —S(O)$_m$R$^5$, —NR$^4$R$^4$, —SO$_2$NR$^4$R$^4$, —CONR$^4$R$^4$, —NR$^4$COR$^5$ or —NR$^4$SO$_2$R$^5$ and said piperazinyl and homopiperazinyl being optionally substituted on the nitrogen not attached to $A^1$ by $C_1$–$C_6$ alkyl, phenyl, $C_1$–$C_6$ alkoxy-($C_2$–$C_6$)-alkyl, $R^4R^4$N—($C_2$–$C_6$)-alkyl, halo-($C_1$–$C_6$)-alkyl, $C_2$–$C_5$ alkanoyl, —COOR$^5$, $C_3$–$C_8$ cycloalkyl, —SO$_2$R$^5$, —SO$_2$NR$^4$R$^4$ or —CONR$^4$R$^4$, or (v) when $A^1$ is $C_1$–$C_6$ alkylene, —COOR$^4$, —CN or —CONR$^4$R$^4$; or
  (c) —X—NR$^{12a}$—Y—NR$^{13}$R$^{14}$ wherein
  X is —CH$_2$— or —CH$_2$CH$_2$—; and
  $R^{12a}$ is H or $C_1$–$C_6$ alkyl; or
  (d) —CO—NR$^{18}$—X$^1$—NR$^{12}$—Y—NR$^{13}$R$^{14}$ wherein
  (i) $X^1$ is (1) unbranched $C_2$–$C_3$ alkylene optionally substituted by $C_1$–$C_6$ alkyl or $C_3$–$C_8$ cycloalkyl or (2) a group of the formula —(CH$_2$)$_n$—W—(CH$_2$)$_p$— wherein W is $C_5$–$C_7$ cycloalkylene, n is 0 or 1 and p is 0 or 1;
  $R^{18}$ is H or $C_1$–$C_6$ alkyl; and
  $R^{12}$ is H or $C_1$–$C_6$ alkyl; or (ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{18}$ is H or $C_1$–$C_6$ alkyl; or (iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{12}$ is H or $C_1$–$C_6$ alkyl;

Y is CO, CS, $SO_2$ or C=N(CN);

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het; either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by flouro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, flouro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^{15}R^{16}$ or —$OR^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het$^1$, or (2) —($C_2$–$C_6$ alkylene)-$NR^8R^9$, or (3) —($C_1$–$C_6$ alkylene)-$R^{17}$, or (4) $C_1$–$C_6$ alkyl or $C_3$–$C_8$ cycloalkyl;

$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^{17}$ is (i) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2(C_1$–$C_6$ alkyl), —($C_1$–$C_3$ alkylene)-$CO_2(C_1$–$C_6$ alkyl), —($C_1$–$C_3$ alkylene)-$NR^{24}R^{24}$, —$CONR^{24}R^{24}$ or —($C_1$–$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het$^1$;

m is 0, 1 or 2;

het, used in the definitions of $R^6$ and $R^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

het$^1$, used in the definition of $R^{14}$ and $R^{17}$, is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$;

$R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and $R^{24}$ is H or $C_1$–$C_6$ alkyl optionally substituted by cyclopropyl.

12. A process for preparing a compound of the formula (I), as defined in claim 1, wherein $R^2$ is —$CH2CH_2$—$NR12a$—$CS$—$NR^{13}R^{14}$, —$CH_2CH_2$—$NR^{12a}$—CO—$NR^{13}R^{14}$ or —$CH_2CH_2$—$NR^{12a}$—C=N(CN)—$NR^{13}R^{14}$, or a pharmaceutically acceptable salt thereof, comprising (a) reacting a compound of the formula (XXXXIII)

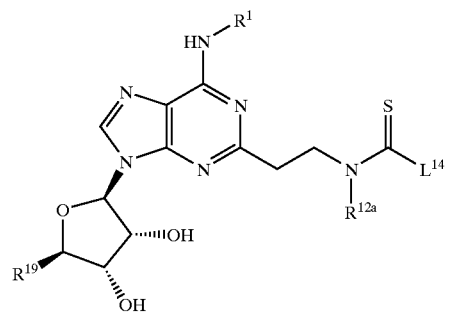

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^{12a}$ is H or $C_1$–$C_6$ alkyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl and $L^{14}$ is a suitable leaving group; or (b) reacting a compound of the formula

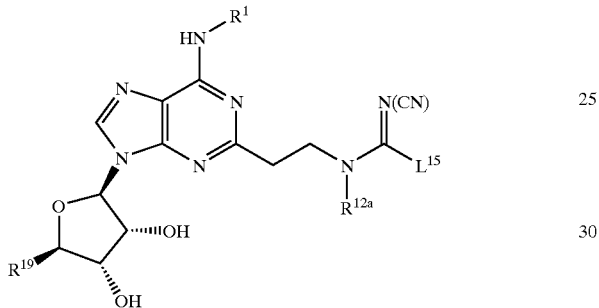

(XXXXIV)

wherein $R^1$, $R^{12a}$ and $R^{19}$ are as defined hereinabove and $L^{15}$ is a suitable leaving group; or (c) reacting a compound of the formula

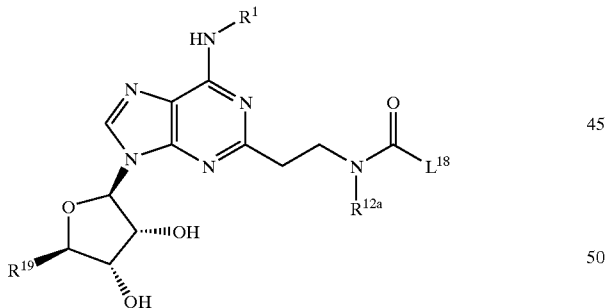

(XXXXVIII)

wherein $R^1$, $R^{12a}$ and $R^{19}$ are as defined hereinabove and $L^{18}$ is a suitable leaving group;

with a compound of the formula $R^3R^4NH$ (XI)

wherein $R^3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^3$ is not H when A is a bond, or (ii) when A is $C_2$–$C_3$ alkylene, —$NR^8R^9$, —$OR^4$, —$COOR^4$, —$OCOR^5$, —$SO_2R^5$, —CN, —$SO_2NR^4R^4$, —$NR^4COR^5$ or —$CONR^4R^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^6$, —$S(O)_m R^7$, —$SO_2NR^6R^6$ or —$CONR^6R^6$;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het; either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

m is 0, 1 or 2; and het means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

said process being optionally followed by the conversion of the compound of the formula (I) to a pharmaceutically acceptable salt thereof.

13. A process for preparing a compound of the formula (I), as defined in claim 1, wherein $R^2$ is —$CONR^{10}$—$A^1$—$R^{11}$, or a pharmaceutically acceptable salt thereof, comprising reacting a compound of the formula

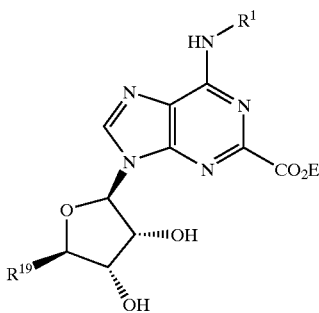

(LI)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl and E is $C_1$–$C_6$ alkyl;

with a compound of the formula

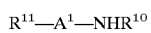   (XVII)

wherein $A^1$ is a bond or $C_1$–$C_6$ alkylene;

$R^{10}$ is H or $C_1$–$C_6$ alkyl; and $R^{11}$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^{11}$ is not H when $A^1$ is a bond, or (ii) when $A^1$ is $C_2$–$C_6$ alkylene, —$NR^4R^4$, —$OR^4$, —$OCOR^5$, —$SO_2R^5$, —$SO_2NR^4R^4$, —$NR^4SO_2R^5$ or —$NR^4COR^5$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR_6SO^2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^7$, —$SO_2R^7$, —$SO_2NR^6R^6$ or —$CONR^6R^6$, or (iv) when $A^1$ is $C_2$–$C_6$ alkylene, N-linked azetidinyl, pyrrolidinyl, piperidinyl, morpholinyl, piperazinyl, homopiperazinyl, homopiperidinyl or tetrahydroquinolinyl, each being optionally C-substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$ and said piperazinyl and homopiperazinyl being optionally substituted on the nitrogen not attached to $A^1$ by $C_1$–$C_6$ alkyl, phenyl, $C_1$–$C_6$ alkoxy-($C_2$–$C_6$)-alkyl, $R^4R^4N$—($C_2$–$C_6$)-alkyl, halo-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or (v) when $A^1$ is $C_1$–$C_6$ alkylene, —$COOR^4$, —CN or —$CONR^4R^4$;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het;

m is 0, 1 or 2; and het means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo, said process being optionally followed by the conversion of the compound of the formula (I) to a pharmaceutically acceptable salt thereof.

14. A process for preparing a compound of the formula (I), as defined in claim 1, wherein $R^2$ is —$CONR^{10}$—$A^1$—$R^{11}$, or a pharmaceutically acceptable salt thereof, comprising reacting a compound of the formula

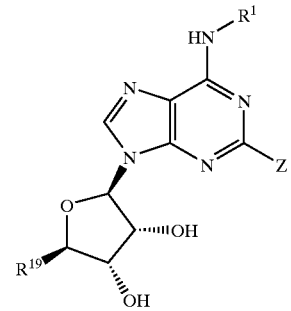

(LIV)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl and Z is a suitable leaving group;

with a compound of the formula $$R^{11}\text{—}A^1\text{—}NHR^{10} \qquad\qquad (XVII)$$

wherein $A^1$ is a bond or $C_1$–$C_6$ alkylene;

$R^{10}$ is H or $C_1$–$C_6$ alkyl; and $R^{11}$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^{11}$ is not H when $A^1$ is a bond, or (ii) when $A^1$ is $C_2$–$C_6$ alkylene, —$NR^4R^4$, —$OR^4$, —$OCOR^5$, —$SO^2R^5$, —$SO_2NR^4R^4$, —$NR^4SO_2R^5$ or —$NR^4COR^5$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^7$, —$SO_2R^7$, —$SO_2NR^6R^6$ or —$CONR^6R^6$, or (iv) when $A^1$ is $C_2$–$C_6$ alkylene, N-linked azetidinyl, pyrrolidinyl, piperidinyl, morpholinyl, piperazinyl, homopiperazinyl, homopiperidinyl or tetrahydroquinolinyl, each being optionally C-substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$ and said piperazinyl and homopiperazinyl being optionally substituted on the nitrogen not attached to $A^1$ by $C_1$–$C_6$ alkyl, phenyl, $C_1$–$C_6$ alkoxy-($C_2$–$C_6$)-alkyl, $R^4R^4N$—($C_2$–$C_6$)-alkyl, halo-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or (v) when $A^1$ is $C_1$–$C_6$ alkylene, —$COOR^4$, —$CN$ or —$CONR^4R^4$;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het;

m is 0, 1 or 2; and het means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo; in the presence of carbon monoxide and a suitable catalyst;

said process being optionally followed by the conversion of the compound of the formula (I) to a pharmaceutically acceptable salt thereof.

15. A process for preparing a compound of the formula (I), as defined in claim 1, wherein $R^2$ is —$CONR^{18}$—$X^1$—$NR^{12}$—$Y$—$NR^{13}R^{14}$, or a pharmaceutically acceptable salt thereof, comprising reacting a compound of the formula

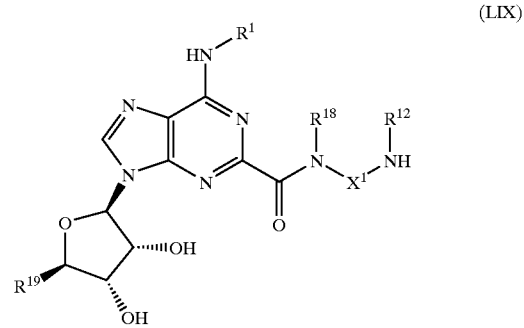

(LIX)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

(i) $X^1$ is (1) unbranched $C_2$–$C_3$ alkylene optionally substituted by $C_1$–$C_6$ alkyl or $C_3$–$C_8$ cycloalkyl or (2) a group of the formula —$(CH_2)_n$—$W$—$(CH_2)_p$— wherein W is $C_5$–$C_7$ cycloalkylene, n is 0 or 1 and p is 0 or 1;

$R^{18}$ is H or $C_1$–$C_6$ alkyl; and $R^{12}$ is H or $C_1$–$C_6$ alkyl; or (ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{18}$ is H or $C_1$–$C_6$ alkyl; or (iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{12}$ is H or $C_1$–$C_6$ alkyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl with (a) a compound of the formula

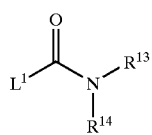

(XIX)

wherein either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^{15}R^{16}$ or —$OR^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het$^1$, or (2) —($C_2$–$C_6$ alkylene)-$NR^8R^9$, or (3) —($C_1$–$C_6$ alkylene)-$R^{17}$, or (4) $C_1$–$C_6$ alkyl or $C_3$–$C_8$ cycloalkyl;

$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^{17}$ is (i) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2(C_1$–$C_6$ alkyl), —($C_1$–$C_3$ alkylene)-$CO_2(C_1$–$C_6$ alkyl), —($C_1$–$C_3$ alkylene)-$NR^{24}R^{24}$, —$CONR^{24}R^{24}$ or —($C_1$–$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het$^1$; either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

m is 0, 1 or 2;

het$^1$ is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl; and $R^{24}$ is H or $C_1$–$C_6$ alkyl optionally substituted by cyclopropyl and $L^1$ is a suitable leaving group; or (b) a compound of the formula $R^{13}R^{14}NSO_2L^4$   (XXII)

wherein $R^{13}$ and $R^{14}$ are as defined hereinabove and $L^4$ is a suitable leaving group; or (c) a compound of the formula $R^{14}R^{13}N$—CS—$L^{12}$   (XXXX)

wherein $R^{13}$ and $R^{14}$ are as defined hereinabove and $L^{12}$ is a suitable leaving group; or (d) a compound of the formula $R^{14}R^{13}N$—C=N(CN)—$L^{13}$   (XXXXI)

wherein $R^{13}$ and $R^{14}$ are as defined hereinabove and $L^{13}$ is a suitable leaving group;

said process being optionally followed by the conversion of the compound of the formula (I) to a pharmaceutically acceptable salt thereof.

16. A compound of the formula (I), as claimed in claim 15, wherein $R^1$ is $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano.

17. A compound of the formula (I), as claimed in claim 16, wherein $R^1$ is 2,2-diphenylethyl.

18. A compound of the formula (I), as claimed in claim 15, wherein $R^2$ is —$CH_2NHSO_2$—A—$R^3$, —$CONR^{10}$—$A^1$—$R^{11}$, or —X—$NR^{12a}$—Y—$NR^{13}R^{14}$.

19. A compound of the formula (I), as claimed in claim 15, wherein $R^{19}$ is C-linked tetrazolyl, oxadiazolyl, oxazolyl, or triazolyl each optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$.

20. A compound of the formula (I), as claimed in claim 19, wherein $R^{19}$ is 2-ethyl-1,2,3,4-tetrazol-5-yl, 3-ethyl-1,2,4-oxadiazol-5-yl, 5-ethyl-1,2,4-oxadiazol-3-yl, 3-ethyl-1,2-oxazol-5-yl, 1-ethyl-1,2,4-triazol-3-yl or 1-ethyl-1,2,3-triazol-4-yl.

21. A compound of the formula (I), as claimed in claim 15, wherein A is a bond, methylene or 1,2-propylene.

22. A compound of the formula (I), as claimed in claim 15, wherein $R^3$ is $C_1$–$C_6$ alkyl.

23. A compound of the formula (I), as claimed in claim 22, wherein $R^3$ is methyl, prop-2-yl or 2-methylprop-1-yl.

24. A compound of the formula (I), as claimed in claim 15, wherein —A—$R^3$ is $C_1$–$C_6$ alkyl.

25. A compound of the formula (I), as claimed in claim 24, wherein —A—$R^3$ is 2-methylprop-1-yl.

26. A compound of the formula (I), as claimed in claim 15, wherein $R^{10}$ is H.

27. A compound of the formula (I), as claimed in claim 15, wherein $A^1$ is $C_1$–$C_6$ alkylene.

28. A compound of the formula (I), as claimed in claim 27, wherein $A^1$ is 1,2-ethylene.

29. A compound of the formula (I), as claimed in claim 15, wherein $R^{11}$ is (i) phenyl optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$ or (ii) piperidin-1-yl optionally C-substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$.

30. A compound of the formula (I), as claimed in claim 29, wherein $R^{11}$ is phenyl or piperidin-1-yl.

31. A compound of the formula (I), as claimed in claim 15, wherein X is —$CH_2$—.

32. A compound of the formula (I), as claimed in claim 15, wherein $R^{12a}$ is H.

33. A compound of the formula (I), as claimed in claim 15, wherein Y is CO.

34. A compound of the formula (I), as claimed in claim 15, wherein $R^{13}$ is H.

35. A compound of the formula (I), as claimed in claim 15, wherein $R^{14}$ is —($C_2$–$C_6$ alkylene)-$NR^8R^9$.

36. A compound of the formula (I), as claimed in claim 35, wherein $R^{14}$ is —$CH_2CH_2NR^8R^9$.

37. A compound of the formula (I), as claimed in claim 15, wherein either (i) $R^8$ and $R^9$, taken together with the nitrogen atom to which they are attached, represent piperidinyl, said piperidinyl being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, $OR^4$, cyano, $S(O)_mR^5$, $NR^4R^4$, —$SO_2NR^4R^4$, —$NR^4COR^5$, or —$NR^4SO_2R^5$ or (ii) $R^8$ is $C_1$–$C_6$ alkyl and $R^9$ is $C_3$–$C_8$ cycloalkyl.

38. A compound of the formula (I), as claimed in claim 37, wherein either $R^8$ and $R^9$, taken together with the nitrogen atom to which they are attached, represent piperidinyl, or $R^8$ is prop-2-yl and $R^9$ is cyclopentyl.

39. A compound of the formula (I), as claimed in claim 18, wherein $R^2$ is
—$CH_2NHSO_2CH_2CH(CH_3)_2$, —$CONHCH_2CH_2Ph$,
—$CH_2NHCONHCH_2CH_2N[CH(CH_3)2][cyclopentyl]$,
—$CH_2NHCONHCH_2CH_2(piperidin-1-yl)$ or
—$CONHCH_2CH_2(-piperidin-1-yl)$.

40. A compound of the formula (I), as claimed in claim 15, which is selected from:

N-({6-[(2,2-diphenylethyl)amino]-9-[(2R,3R,4S,5R)-5-(2-ethyl-2H-tetrazol-5-yl)-3,4-dihydroxytetrahydro-2-furanyl]-9H-purin-2-yl}methyl)-2-methyl-1-propanesulphonamide;

6-[(2,2-diphenylethyl)amino]-9-[(2R,3R,4S,5R)-5-(2-ethyl-2H-tetrazol-5-yl)-3,4-dihydroxytetrahydro-2-furanyl]-N-[2-(1-piperidinyl)ethyl]-9H-purine-2-carboxamide;

6-[(2,2-diphenylethyl)amino]-9-[(2R,3R,4S,5R)-5-(2-ethyl-2H-tetrazol-5-yl)-3,4-dihydroxytetrahydro-2-furanyl]-N-(2-phenylethyl)-9H-purine-2-carboxamide;

N-({6-[(2,2-diphenylethyl)amino]-9-[(2R,3R,4S,5S)-5-(3-ethyl-1,2,4-oxadiazol-5-yl)-3,4-dihydroxytetrahydro-2-furanyl]-9H-purin-2-yl}methyl)-2-methyl-1-propanesulphonamide;

6-[(2,2-diphenylethyl)amino]-9-[(2R,3R,4S,5S)-5-(3ethyl-5-isoxazolyl)-3,4-dihydroxytetrahydro-2-furanyl]-N-[2-(1-piperidinyl)ethyl]-9H-purine-2-carboxamide;

N-({6-[(2,2-diphenylethyl)amino]-9-[(2R,3R,4S,5R)-5-(1-ethyl-1H-1,2,4-triazol-3-yl)-3,4-dihydroxytetrahydro-2-furanyl]-9H-purin-2-yl}methyl)-2-methyl-1-propanesulphonamide;

6-[(2,2-diphenylethyl)amino]-9-[(2R,3R,4S,5R)-5-(1-ethyl-1H-1,2,4-triazol-3-yl)-3,4-dihydroxytetrahydro-2-furanyl]-N-[2-(1-piperidinyl)ethyl]-9H-purine-2-carboxamide;

N-({6-[(2,2-diphenylethyl)amino]-9-[(2R,3R,4S,5R)-5-(5-ethyl-1,2,4-oxadiazol-3-yl)-3,4-dihydroxytetrahydro-2-furanyl]-9H-purin-2-yl}methyl)-2-methyl-1-propanesulphonamide;

N-({6-[(2,2-diphenylethyl)amino]-9-[(2R,3R,4S,5R)-5-(1-ethyl-1H-1,2,3-triazol-4-yl)-3,4-dihydroxytetrahydro-2-furanyl]-9H-purin-2-yl}methyl)-2-methyl-1-propanesulphonamide;

N-{2-[cyclopentyl(isopropyl)amino]ethyl}-N-({6-[(2,2-diphenylethyl)amino]-9-[(2R,3R,4S,5R)-5-(2-ethyl-2H-tetrazol-5-yl)-3,4-dihydroxytetrahydro-2-furanyl]-9H-purin-2-yl}methyl)urea; and N-({6-[(2,2-diphenylethyl)amino]-9-[(2R,3R,4S,5R)-5-(2-ethyl-2H-tetrazol-5-yl)-3,4-dihydroxytetrahydro-2-furanyl]-9H-purin-2-yl}methyl)-N'-[2-(1-piperidinyl)ethyl]urea;

and the pharmaceutically acceptable salts thereof.

41. A pharmaceutical composition comprising a compound of claim 15 or a pharmaceutically acceptable salt thereof and a pharmaceutically acceptable excipient, diluent or carrier.

42. A process for preparing a compound of the formula (I), as defined in claim 1, wherein $R^2$ is —$CONR^{18}$—$X^1$—$NR^{12}$—$CS$—$NR^{13}R^{14}$, —$CONR^{18}$—$X^1$—$NR^{12}$—$CO$—$NR^{13}R^{14}$ or —$CONR^{18}$—$X^1$—$NR^{12}$—$C$=$N(CN)$—$NR^{13}R^{14}$, or a pharmaceutically acceptable salt thereof, comprising (a) reacting a compound of the formula

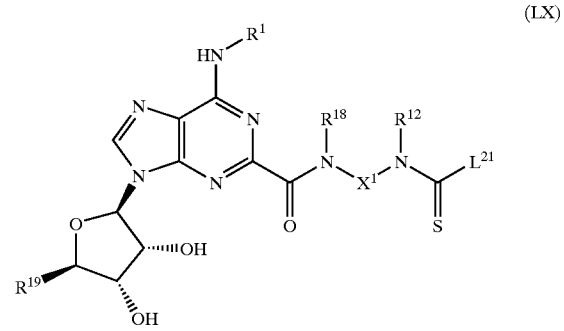

(LX)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

(i) $X^1$ is (1) unbranched $C_2$–$C_3$ alkylene optionally substituted by $C_1$–$C_6$ alkyl or $C_3$–$C_8$ cycloalkyl or (2) a group of the formula —$(CH_2)_n$—W—$(CH_2)_p$— wherein W is $C_5$–$C_7$ cycloalkylene, n is 0 or 1 and p is 0 or 1;

$R^{18}$ is H or $C_1$–$C_6$ alkyl; and $R^{12}$ is H or $C_1$–$C_6$ alkyl; or (ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{18}$ is H or $C_1$–$C_6$ alkyl; or (iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{12}$ is H or $C_1$–$C_6$ alkyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and $L^{21}$ is a suitable leaving group; or (b) reacting a compound of the formula

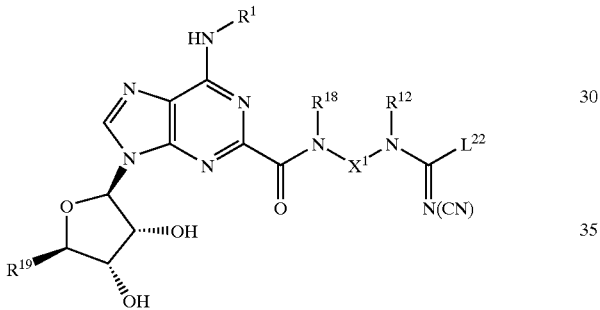

(LXI)

wherein $R^1$, $R^{18}$, $X^1$, $R^{12}$ and $R^{19}$ are as defined hereinabove and $L^{22}$ is a suitable leaving group; or (c) reacting a compound of the formula

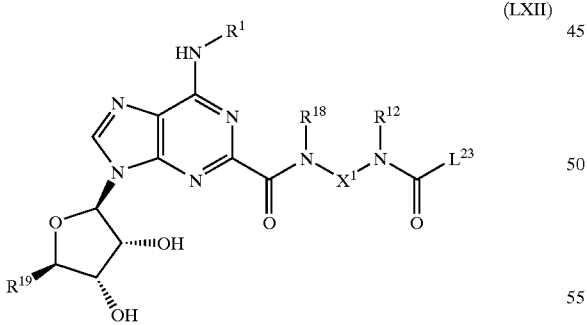

(LXII)

wherein $R^1$, $R^{18}$, $X^1$, $R^{12}$ and $R^{19}$ are as defined hereinabove and $L^{23}$ is a suitable leaving group; with a compound of the formula $R^3R^4NH$  (XI)

wherein $R^3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$— ($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^3$ is not H when A is a bond, or (ii) when A is $C_2$–$C_3$ alkylene, —$NR^8R^9$, —$OR^4$, —$COOR^4$, —$OCOR^5$, —$SO_2R^5$, —$CN$, —$SO_2NR^4R^4$, —$NR^4COR^5$ or —$CONR^4R^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^6$, —$S(O)_m R^7$, —$SO_2NR^6R^6$ or —$CONR^6R^6$;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het;

either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

m is 0, 1 or 2; and het means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

said process being optionally followed by the conversion of the compound of the formula (I) to a pharmaceutically acceptable salt thereof.

43. A process for preparing a compound of the formula (I), as defined in claim 1, wherein $R^2$ is —$CONR^{18}$—$X^1$—

$NR^{12}$—Y—$NR^{13}R^{14}$, or a pharmaceutically acceptable salt thereof, comprising reacting a compound of the formula

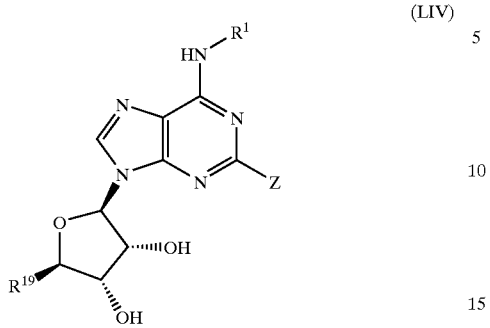

(LIV)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl; $R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and Z is a suitable leaving group;

with a compound of the formula

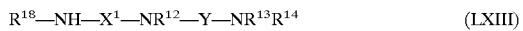

$R^{18}$—NH—$X^1$—$NR^{12}$—Y—$NR^{13}R^{14}$ (LXIII)

wherein (i) $X^1$ is (1) unbranched $C_2$–$C_3$ alkylene optionally substituted by $C_1$–$C_6$ alkyl or $C_3$–$C_8$ cycloalkyl or (2) a group of the formula —$(CH_2)_n$—W—$(CH_2)_p$— wherein W is $C_5$–$C_7$ cycloalkylene, n is 0 or 1 and p is 0 or 1;

$R^{18}$ is H or $C_1$–$C_6$ alkyl; and $R^{12}$ is H or $C_1$–$C_6$ alkyl; or (ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{18}$ is H or $C_1$–$C_6$ alkyl; or (iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{12}$ is H or $C_1$–$C_6$ alkyl;

Y is CO, CS, $SO_2$ or C=N(CN);

either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^{15}R^{16}$ or —$OR^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het$^1$, or (2) —($C_2$–$C_6$ alkylene)-$NR^8R^9$, or (3) —($C_1$–$C_6$ alkylene)-$R^{17}$, or (4) $C_1$–$C_6$ alkyl or $C_3$–$C_8$ cycloalkyl;

$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and $R^4$ is H, $C_1$–$C_6$ alkyl, $C_3$–$C_8$ cycloalkyl or phenyl;

either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

$R^{17}$ is (i) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{24}R^{24}$, —$CONR^{24}R^{24}$ or —($C_1$–$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het$^1$;

$R^5$ is $C_1$–$C_6$ alkyl, $C_3$–$C_8$ cycloalkyl or phenyl;

m is 0, 1 or 2;

het$^1$ is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo; and $R^{24}$ is H or $C_1$–$C_6$ alkyl optionally substituted by cyclopropyl; in the presence of carbon monoxide and a suitable catalyst; said process being optionally followed by the conversion of the compound of the formula (I) to a pharmaceutically acceptable salt thereof.

44. A process for preparing a compound of the formula (I), as defined in claim 1, wherein $R^2$ is —CONR$^{18}$—X$^1$—NR$^{12}$—Y—NR$^{13}$R$^{14}$, or a pharmaceutically acceptable salt thereof, comprising reacting a compound of the formula (LI)

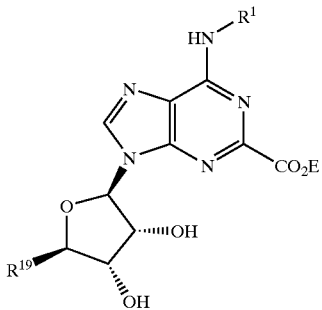

wherein: $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl; $R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —NR$^{20}$R$^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and E is $C_1$–$C_6$ alkyl;
with a compound of the formula

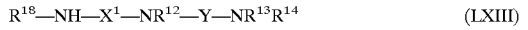

wherein
- (i) $X^1$ is (1) unbranched $C_2$–$C_3$ alkylene optionally substituted by $C_1$–$C_6$ alkyl or $C_3$–$C_8$ cycloalkyl or (2) a group of the formula —(CH$_2$)$_n$—W—(CH$_2$)$_p$— wherein W is $C_5$–$C_7$ cycloalkylene, n is 0 or 1 and p is 0 or 1;
  $R^{18}$ is H or $C_1$–$C_6$ alkyl; and
  $R^{12}$ is H or $C_1$–$C_6$ alkyl; or
- (ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and
  $R^{18}$ is H or $C_1$–$C_6$ alkyl; or
- (iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and
  $R^{12}$ is H or $C_1$–$C_6$ alkyl;
Y is CO, CS, SO$_2$ or C=N(CN);
either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —NR$^{15}$R$^{16}$ or —OR$^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het$^1$, or (2) —(C$_2$–$C_6$ alkylene)-NR$^8$R$^9$, or (3) —(C$_1$–$C_6$ alkylene)-R$^{17}$, or (4) $C_1$–$C_6$ alkyl or $C_3$–$C_8$ cycloalkyl;
$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and
$R^4$ is H, $C_1$–$C_6$ alkyl, $C_3$–$C_8$ cycloalkyl or phenyl;
either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —CONR$^4$R$^4$, —COOR$^4$ or $C_2$–$C_5$ alkanoyl, and optionally substituted on a ring carbon atom not adjacent to a ring nitrogen atom by fluoro-($C_1$–$C_6$)-alkoxy, halo, —OR$^4$, cyano, —S(O)$_m$R$^5$, —NR$^4$R$^4$, —SO$_2$NR$^4$R$^4$, —NR$^4$COR$^5$ or —NR$^4$SO$_2$R$^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —COOR$^5$, $C_3$–$C_8$ cycloalkyl, —SO$_2$R$^5$, —SO$_2$NR$^4$R$^4$ or —CONR$^4$R$^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —CONR$^4$R$^4$, —COOR$^5$, —COR$^5$, —SO$_2$R$^5$ or —SO$_2$NR$^4$R$^4$, said $C_1$–$C_6$ alkyl being optionally substituted by phenyl;
$R^{17}$ is (i) phenyl, pyridin-2-yl, pyridin-3-yl or pyridin-4-yl, each being optionally substituted be $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —CO$_2$H, —($C_1$–$C_3$ alkylene)-CO$_2$H, —CO$_2$($C_1$–$C_6$ alkyl), —($C_1$–$C_3$ alkylene)-CO$_2$($C_1$–$C_6$ alkyl), —($C_1$–$C_3$ alkylene)-NR$^{24}$R$^{24}$, —CONR$^{24}$R$^{24}$ or —($C_1$–$C_3$ alkylene)-CONR$^{24}$R$^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het$^1$;
$R^5$ is $C_1$–$C_6$ alkyl, $C_3$–$C_8$ cycloalkyl or phenyl;
m is 0, 1 or 2;
het$^1$ is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo; and
$R^{24}$ is H or $C_1$–$C_6$ alkyl optionally substituted by cyclopropyl;
said process being optionally followed by the conversion of the compound of the formula (I) to a pharmaceutically acceptable salt thereof.

45. A process for preparing a compound of the formula (I), as defined in claim 1, wherein $R^2$ is —$CH_2CH_2$—$NR^{12a}$—Y—$NR^{13}R^{14}$, or a pharmaceutically acceptable salt thereof, comprising reacting a compound of the formula

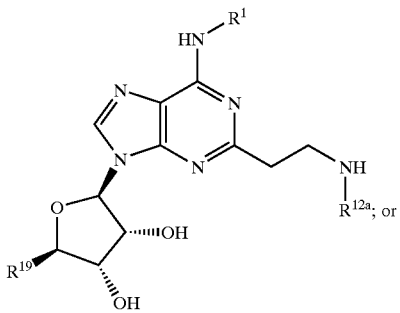

(XXXXII)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^{12a}$ is H or $C_1$–$C_6$ alkyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl with (a) a compound of the formula

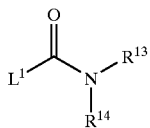

(XIX)

wherein either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^{15}R^{16}$ or —$OR^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het$^1$, or (2) —($C_2$–$C_6$ alkylene)-$NR^8R^9$, or (3) —($C_1$–$C_6$ alkylene)-$R^{17}$, or (4) $C_1$–$C_6$ alkyl or $C_3$–$C_8$ cycloalkyl;

$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^{17}$ is (i) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{24}R^{24}$, —$CONR^{24}R^{24}$ or —($C_1$–$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het$^1$; either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

m is 0, 1 or 2;

het$^1$ is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl; and $R^{24}$ is H or $C_1$–$C_6$ alkyl optionally substituted by cyclopropyl and $L^1$ is a suitable leaving group; or (b) a compound of the formula

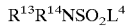

$R^{13}R^{14}NSO_2L^4$ (XXII)

wherein $R^{13}$ and $R^{14}$ are as defined hereinabove and $L^4$ is a suitable leaving group; or (c) a compound of the formula

$R^{14}R^{13}N$—CS—$L^{12}$ (XXXX)

wherein $R^{13}$ and $R^{14}$ are as defined hereinabove and $L^{12}$ is a suitable leaving group; or (d) a compound of the formula

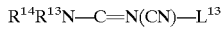

$R^{14}R^{13}N$—C═N(CN)—$L^{13}$ (XXXXI)

wherein $R^{13}$ and $R^{14}$ are as defined hereinabove and $L^{13}$ is a suitable leaving group;

said process being optionally followed by the conversion of the compound of the formula (I) to a pharmaceutically acceptable salt thereof.

46. A process for preparing a compound of the formula (I), as defined in claim 15, wherein $R^2$ is —$CH_2NR^{12a}$—CS—$NR^{13}R^{14}$, —$CH_2$—$NR^{12a}$—CO—$NR^{13}R^{14}$ or —$CH_2$—$NR^{12a}$—C=N(CN)—$NR^{13}R^{14}$, or a pharmaceutically acceptable salt thereof, comprising (a) reacting a compound of the formula

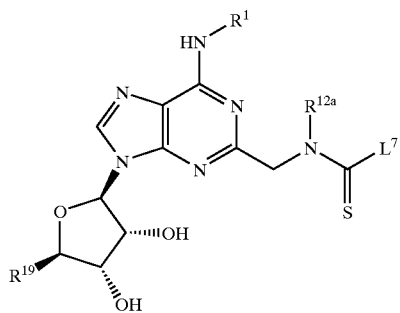

(XXXVI)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^{12a}$ is H or $C_1$–$C_6$ alkyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl and $L^7$ is a suitable leaving group; or (b) reacting the reaction of a compound of the formula

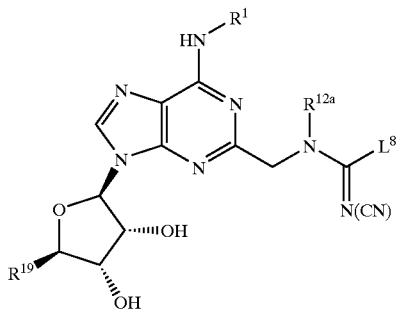

(XXXVII)

wherein $R^1$, $R^{12a}$ and $R^{19}$ are as defined hereinabove and $L^8$ is a suitable leaving group; or (c) reacting a compound of the formula

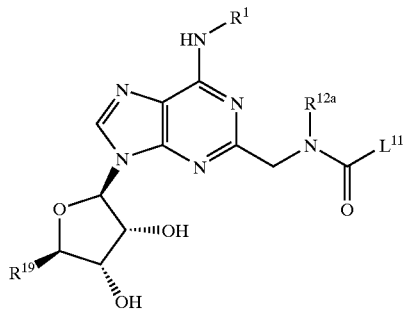

(XXXIX)

wherein $R^1$, $R^{12a}$ and $R^{19}$ are as defined hereinabove and $L^{11}$ is a suitable leaving group;

with a compound of the formula $R^3R^4NH$ (XI)

wherein $R^3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^3$ is not H when A is a bond, or (ii) when A is $C_2$–$C_3$ alkylene, —$NR^8R^9$, —$OR^4$, —$COOR^4$, —$OCOR^5$, —$SO_2R^5$, —CN, —$SO_2NR^4R^4$, —$NR^4COR^5$ or —$CONR^4R^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-$C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^6$, —$S(O)_mR^7$, —$SO^2NR^6R^6$ or —$CONR^6R^6$;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het;

either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

m is 0, 1 or 2; and het means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

said process being optionally followed by the conversion of the compound of the formula (I) to a pharmaceutically acceptable salt thereof.

47. A process for preparing a compound of the formula (I), as defined in claim 15, or a pharmaceutically acceptable salt thereof, comprising deprotecting a compound of the formula

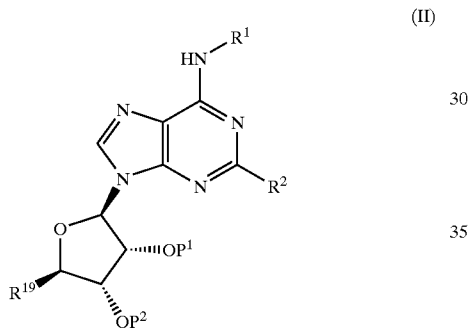

(II)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^2$ is either (a) —$CH_2NHSO_2$—A—$R^3$ wherein

A is a bond or $C_1$–$C_3$ alkylene; and $R^3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^3$ is not H when A is a bond, or (ii) when A is $C_2$–$C_3$ alkylene, —$NR^8R^9$, —$OR^4$, —$COOR^4$, —$OCOR^5$, —$SO_2R^5$, —CN, —$SO_2NR^4R^4$, —$NR^4COR^5$ or —$CONR^4R^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^6$, —$S(O)_mR^7$, —$SO_2NR^6R^6$ or —$CONR^6R^6$; or (b) —$CONR^{10}$—$A^1$—$R^{11}$ wherein $A^1$ is a bond or $C_1$–$C_6$ alkylene;

$R^{10}$ is H or $C_1$–$C_6$ alkyl; and $R^{11}$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^{11}$ is not H when $A^1$ is a bond, or (ii) when $A^1$ is $C_2$–$C_6$ alkylene, —$NR^4R^4$, —$OR^4$, —$OCOR^5$, —$SO_2R^5$, —$SO_2NR^4R^4$, —$NR^4SO_2R^5$ or —$NR^4COR^5$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^7$, —$SO_2R^7$, —$SO_2NR^6R^6$ or —$CONR^6R^6$, or (iv) when $A^1$ is $C_2$–$C_6$ alkylene, N-linked azetidinyl, pyrrolidinyl, piperidinyl, morpholinyl, piperazinyl, homopiperazinyl, homopiperidinyl or tetrahydroquinolinyl, each being optionally C-substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$ and said piperazinyl and homopiperazinyl being optionally substituted on the nitrogen not attached to $A^1$ by $C_1$–$C_6$ alkyl, phenyl, $C_1$–$C_6$ alkoxy-($C_2$–$C_6$)-alkyl, $R^4R^4N$—($C_2$–$C_6$)-alkyl, halo-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or (v) when $A^1$ is $C_1$–$C_6$ alkylene, —$COOR^4$, —CN or —$CONR^4R^4$; or (c) —X—$NR^{12a}$—Y—$NR^{13}R^{14}$ wherein X is —$CH_2$— or —$CH_2CH_2$—; and $R^{12a}$ is H or $C_1$–$C_6$ alkyl; or (d) —CO—$NR^{18}$—$X^1$—$NR^{12}$—Y—$NR^{13}R^{14}$ wherein (i) $X^1$ is (1) unbranched $C_2$–$C_3$ alkylene optionally substituted by $C_1$–$C_6$ alkyl or $C_3$–$C_8$ cycloalkyl or (2) a group of the formula —$(CH_2)_n$—W—$(CH_2)_p$— wherein W is $C_5$–$C_7$ cycloalkylene, n is 0 or 1 and p is 0 or 1;

$R^{18}$ is H or $C_1$–$C_6$ alkyl; and $R^{12}$ is H or $C_1$–$C_6$ alkyl; or (ii) $X^1$ and $R^{12}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{18}$ is H or $C_1$–$C_6$ alkyl; or (iii) $X^1$ and $R^{18}$, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; and $R^{12}$ is H or $C_1$–$C_6$ alkyl;

Y is CO, CS, $SO_2$ or C=N(CN);

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het;

either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^{15}R^{16}$ or —$OR^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het¹, or (2) —($C_2$–$C_6$ alkylene)-$NR^8R^9$, or (3) —($C_1$–$C_6$ alkylene)-$R^{17}$, or (4) $C_1$–$C_6$ alkyl or $C_3$–$C_8$ cycloalkyl;

$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^{17}$ is (i) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2(C_1$–$C_6$ alkyl), —($C_1$–$C_3$ alkylene)-$CO_2(C_1$–$C_6$ alkyl), —($C_1$–$C_3$ alkylene)-$NR^{24}R^{24}$, —$CONR^{24}R^{24}$ or —($C_1$–$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het¹;

m is 0, 1 or 2;

het means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

het¹ is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$;

$R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl; and $R^{24}$ is H or $C_1$–$C_6$ alkyl optionally substituted by cyclopropyl; and either $P^1$ and $P^2$ when taken separately, are protecting groups or, $P^1$ and $P^2$, when taken together are a protecting group; in the case where $P^1$ and $P^2$ are taken separately, the protecting groups being removed together or sequentially;

said process being optionally followed by the conversion of the compound of the formula (I) to a pharmaceutically acceptable salt thereof.

48. A process for preparing a compound of the formula (I), as defined in claim 15, wherein $R^2$ is —$CH_2NHSO_2$—A—$R^3$, or a pharmaceutically acceptable salt thereof, comprising reacting a compound of the formula

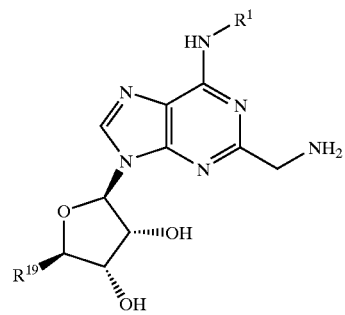

(XXXII)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl with a compound of the formula $$R^3\text{—}A\text{—}SO_2L^x \qquad (VII)$$

in which $L^x$ is a suitable leaving group; A is a bond or $C_1$–$C_3$ alkylene; and $R^3$ is (i) H, $C_1$–$C_6$ alkyl, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy-($C_1$–$C_6$)-alkyl, $R^4R^4N$—($C_1$–$C_6$)-alkyl, halo-($C_1$–$C_6$)-alkyl, fluoro-($C_1$–$C_6$)-alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, with the proviso that $R^3$ is not H when A is a bond, or (ii) when A is $C_2$–$C_3$ alkylene, —$NR^8R^9$, —$OR^4$, —$COOR^4$, —$OCOR^5$, —$SO_2R^5$, —CN, —$SO_2NR^4R^4$, —$NR^4COR^5$ or —$CONR^4R^4$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^6R^6N$—($C_1$–$C_6$)-alkyl, halo-($C_1$–$C_6$)-alkyl, fluoro-($C_1$–$C_6$)-alkoxy, fluoro-($C_2$–$C_5$)-alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy-($C_1$–$C_6$)-alkyl, $R^6R^6N$—($C_2$–$C_6$)-alkyl, halo-($C_1$–$C_6$)-alkyl, fluoro-($C_2$–$C_5$)-alkanoyl, $R^7$, —$COR^6$, —$COOR^6$, —$S(O)_mR^7$, —$SO_2NR^6R^6$ or —$CONR^6R^6$;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het;

either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

m is 0, 1 or 2; and het means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

said process being optionally followed by the conversion of the compound of the formula (I) to a pharmaceutically acceptable salt thereof.

49. A process for preparing a compound of the formula (I), as defined in claim 15, wherein $R^2$ is —$CH_2$—$NR^{12a}$—Y—$NR^{13}R^{14}$, or a pharmaceutically acceptable salt thereof, comprising reacting a compound of the formula

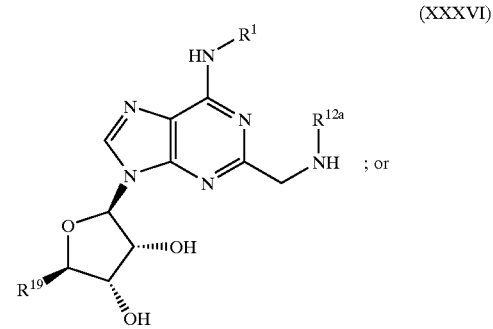

(XXXVI)

wherein $R^1$ is (i) H, (ii) $C_1$–$C_6$ alkyl optionally substituted by 1 or 2 substituents each independently selected from fluorenyl, phenyl and naphthyl, said phenyl, naphthyl and fluorenyl being optionally substituted by $C_1$–$C_6$ alkyl, $C_1$–$C_6$ alkoxy, halo or cyano, or (iii) fluorenyl;

$R^{12a}$ is H or $C_1$–$C_6$ alkyl;

$R^{19}$ is a C-linked, 5-membered aromatic heterocycle containing either (i) from 1 to 4 ring nitrogen atoms or (ii) 1 or 2 ring nitrogen atoms and 1 oxygen or 1 sulphur ring atom, said heterocycle being optionally substituted by $C_1$–$C_6$ alkyl, said $C_1$–$C_6$ alkyl being optionally substituted by phenyl, —OH, $C_1$–$C_6$ alkoxy or —$NR^{20}R^{21}$; and $R^{20}$ and $R^{21}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl with (a) a compound of the formula

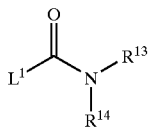
(XIX)

wherein either, $R^{13}$ and $R^{14}$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^{15}R^{16}$ or —$OR^4$, or, $R^{13}$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^{14}$ is (1) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het$^1$, or (2) —($C_2$–$C_6$ alkylene)-$NR^8R^9$, or (3) —($C_1$–$C_6$ alkylene)-$R^{17}$, or (4) $C_1$–$C_6$ alkyl or $C_3$–$C_8$ cycloalkyl;

$R^{15}$ and $R^{16}$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^{17}$ is (i) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{24}R^{24}$, —$CONR^{24}R^{24}$ or —($C_1$–$C_3$ alkylene)-$CONR^{24}R^{24}$, or (ii) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het$^1$;

either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^4R^4N$—($C_1$–$C_6$)-alkyl, fluoro-($C_1$–$C_6$)-alkyl, —$CONR^4R^4$, —$COOR^4$ or $C_2$–$C_5$ alkanoyl, and optionally substituted on a ring carbon atom not adjacent to a ring nitrogen atom by fluoro-($C_1$–$C_6$)-alkoxy, halo, —$OR^4$, cyano, —$S(O)_mR^5$, —$NR^4R^4$, —$SO_2NR^4R^4$, —$NR^4COR^5$ or —$NR^4SO_2R^5$, and said piperazin-1-yl and homopiperazin-1-yl being optionally substituted on the ring nitrogen atom not attached to A or the $C_2$–$C_6$ alkylene group, as the case may be, by $C_1$–$C_6$ alkyl, phenyl, $C_1$–$C_6$ alkoxy-($C_2$–$C_6$)-alkyl, $R^4R^4N$—($C_2$–$C_6$)-alkyl, fluoro-($C_1$–$C_6$)-alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^4R^4$, —$COOR^5$, —$COR^5$, —$SO_2R^5$ or —$SO_2NR^4R^4$, said $C_1$–$C_6$ alkyl being optionally substituted by phenyl;

m is 0, 1 or 2;

het$^1$ is a C-linked, 4- to 6-membered ring heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

$R^4$ is H, $C_1$–$C_6$ alkyl, $C_3$–$C_8$ cycloalkyl or phenyl;

$R^5$ is $C_1$–$C_6$ alkyl, $C_3$–$C_8$ cycloalkyl or phenyl; and $R^{24}$ is H or $C_1$–$C_6$ alkyl optionally substituted by cyclopropyl and $L^1$ is a suitable leaving group; or (b) a compound of the formula

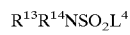
(XXII)

wherein $R^{13}$ and $R^{14}$ are as defined hereinabove and $L^4$ is a suitable leaving group; or (c) a compound of the formula

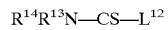
(XXXX)

wherein $R^{13}$ and $R^{14}$ are as defined hereinabove and $L^{12}$ is a suitable leaving group; or (d) a compound of the formula

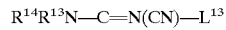
(XXXXI)

wherein $R^{13}$ and $R^{14}$ are as defined hereinabove and $L^{13}$ is a suitable leaving group;

said process being optionally followed by the conversion of the compound of the formula (I) to a pharmaceutically acceptable salt thereof.

50. A process of claim 45 or 15 wherein $L^1$ is imidazol-yl; $L^4$ is chloro; $L^{12}$ is methylthio or imidazol-1-yl; and $L^{13}$ is methylthio.

51. A process of claim 46 wherein $L^7$ is methylthio or imidazol-1-yl; $L^8$ is methylthio; and $L^{11}$ is imidazol-1-yl.

52. A process of claim 12 wherein $L^{14}$ is methylthio or imidazol-1-yl; $L^{15}$ is methylthio; and $L^{18}$ is imidazol-1-yl.

53. A process of claim 14 or 43 wherein Z is iodo.

54. A process of claim 42 wherein $L^{21}$ is methylthio or imidazol-1-yl; $L^{22}$ is methylthio; and $L^{23}$ is imidazol-1-yl.

* * * * *